US012714534B2

(12) United States Patent
Schuele

(10) Patent No.: US 12,714,534 B2
(45) Date of Patent: Aug. 25, 2026

(54) HEAD STABILIZATION SYSTEM WITH ADJUSTABLE-FILL PADS AND METHOD OF USE

(71) Applicant: Black Forest Medical GmbH, Freiburg im Breisgau (DE)

(72) Inventor: Matthias E. Schuele, Freiburg (DE)

(73) Assignee: Black Forest Medical GmbH, Freiburg im Breisgau (DE)

( * ) Notice: Subject to any disclaimer, the term of this patent is extended or adjusted under 35 U.S.C. 154(b) by 0 days.

(21) Appl. No.: 16/395,909

(22) Filed: Apr. 26, 2019

(65) Prior Publication Data

US 2019/0328478 A1 Oct. 31, 2019

Related U.S. Application Data

(60) Provisional application No. 62/662,874, filed on Apr. 26, 2018, provisional application No. 62/662,855, filed on Apr. 26, 2018.

(51) Int. Cl.
*A61B 90/14* (2016.01)
*A61B 90/00* (2016.01)
(Continued)

(52) U.S. Cl.
CPC .............. *A61B 90/14* (2016.02); *A61B 90/06* (2016.02); *A61B 90/57* (2016.02); *A61G 13/121* (2013.01);
(Continued)

(58) Field of Classification Search
CPC .............. A61B 90/14; A61B 2090/065; A61B 2090/0811; A61B 4/0421; A61G 13/12;
(Continued)

(56) References Cited

U.S. PATENT DOCUMENTS 4,354,284 A 10/1982 Gooding
5,009,318 A * 4/1991 Lepinoy .................. B29C 65/18 53/472

(Continued)

FOREIGN PATENT DOCUMENTS

CN 103517730 A 1/2014
CN 204562489 U 8/2015

(Continued)

OTHER PUBLICATIONS

International Search Report and Written Opinion dated Jan. 3, 2019 for Application No. PCT/IB2018/001027, 11 pgs.

(Continued)

*Primary Examiner* — Alireza Nia
*Assistant Examiner* — Robin Han
(74) *Attorney, Agent, or Firm* — FBT Gibbons LLP

(57) ABSTRACT

Exemplary head stabilization devices or head fixation devices (HFDs) include lateral head supports for providing lateral support to the head of the patient. The lateral head supports include a pad with a fillable chamber where the fill amount of the material within the chamber can be adjusted or changed. This allows the pressure the lateral head supports apply to the head of the patient to be changed as desired. The material used within the pad chamber can be of any suitable type, including a gel, a liquid, a gas, a solid, and combinations of these materials.

16 Claims, 31 Drawing Sheets

(51) Int. Cl.
*A61B 90/57* (2016.01)
*A61G 13/12* (2006.01)

(52) U.S. Cl.
CPC ....... *A61G 13/1265* (2013.01); *A61G 13/127* (2013.01); *A61B 2090/065* (2016.02); *A61B 2090/0811* (2016.02); *A61G 2203/32* (2013.01); *A61G 2203/34* (2013.01)

(58) Field of Classification Search
CPC .............. A61G 13/121; A61G 13/0054; A61G 13/1295; A61G 13/1265; A61G 13/127; A61G 13/1285; A61G 2200/325; A61G 7/07; A61G 15/125; A61G 7/05776; A61G 13/1275; A61G 7/072; A61H 2201/0134; A47G 2009/008; A47G 2009/1018; A47G 9/1027; A47G 9/1081; A61F 5/34
USPC ........................ 297/400; 5/640, 637; 128/865
See application file for complete search history.

(56) References Cited

U.S. PATENT DOCUMENTS

| | | | | |
|---|---|---|---|---|
| 5,311,882 | A * | 5/1994 | Gagne | A61F 5/34 128/DIG. 20 |
| 5,577,998 | A | 11/1996 | Johnson, Jr. et al. | |
| 5,676,509 | A | 10/1997 | Enzu | |
| 6,139,106 | A | 10/2000 | Aldridge | |
| 6,355,049 | B1 * | 3/2002 | Gill | A61B 90/14 5/622 |
| 6,557,195 | B2 | 5/2003 | Dinkler | |
| 6,594,839 | B1 | 7/2003 | Papay | |
| 7,117,551 | B1 * | 10/2006 | Dinkler | A61G 13/12 5/643 |
| 7,213,883 | B2 | 5/2007 | Chamitski | |
| 7,730,563 | B1 | 6/2010 | Sklar et al. | |
| 7,797,773 | B1 * | 9/2010 | Wilk | A47C 7/383 5/640 |
| 2002/0032927 | A1 | 3/2002 | Dinkler | |
| 2002/0042618 | A1 | 4/2002 | Tweardy | |
| 2002/0151907 | A1 | 10/2002 | Day et al. | |
| 2003/0051293 | A1 | 3/2003 | Chapman et al. | |
| 2004/0260311 | A1 | 12/2004 | Bourel et al. | |
| 2006/0123548 | A1 * | 6/2006 | Heath | A47G 9/10 5/655.5 |
| 2006/0267392 | A1 * | 11/2006 | Charnitski | A47C 7/383 297/393 |
| 2008/0077151 | A1 | 3/2008 | Kring | |
| 2009/0306662 | A1 | 12/2009 | Dinkler | |
| 2010/0078034 | A1 | 4/2010 | Fischer et al. | |
| 2014/0135765 | A1 | 5/2014 | Schuele et al. | |
| 2014/0275987 | A1 | 9/2014 | Bzostek et al. | |
| 2015/0052685 | A1 | 2/2015 | Bhat et al. | |
| 2015/0327937 | A1 | 11/2015 | Schuele | |
| 2015/0328035 | A1 | 11/2015 | Idowu et al. | |
| 2016/0028796 | A1 | 1/2016 | Garcia et al. | |
| 2016/0106508 | A1 | 4/2016 | Lathrop et al. | |
| 2016/0151224 | A1 | 6/2016 | Ferro et al. | |
| 2016/0175178 | A1 | 6/2016 | Charles | |
| 2016/0324592 | A1 | 11/2016 | Schuele | |
| 2017/0014201 | A1 | 1/2017 | Grotenhuis | |
| 2019/0053871 | A1 | 2/2019 | Moosmann et al. | |
| 2019/0053967 | A1 | 2/2019 | Moosmann et al. | |
| 2019/0328478 | A1 | 10/2019 | Schuele | |

FOREIGN PATENT DOCUMENTS

| | | | |
|---|---|---|---|
| CN | 105125286 | A | 12/2015 |
| CN | 103857433 | A | 4/2016 |
| CN | 107223027 | A | 9/2017 |
| EP | 1 009 284 | B1 | 6/2000 |
| EP | 2014251 | A1 | 1/2009 |
| GB | 2 262 435 | A | 6/1993 |
| JP | S52-125388 | U | 10/1977 |
| JP | 2002-536119 | A | 10/2002 |
| JP | 2004-509703 | A | 4/2004 |
| JP | 2010-523269 | A | 7/2010 |
| JP | 2013-517915 | A | 5/2013 |
| JP | 2013-526970 | A | 6/2013 |
| WO | WO 1999/029252 | A1 | 6/1999 |
| WO | WO 2016/028796 | A1 | 2/2016 |
| WO | WO 2019/034933 | A2 | 2/2019 |
| WO | WO 2019/034935 | A1 | 2/2019 |
| WO | WO 2020/065399 | A1 | 4/2020 |

OTHER PUBLICATIONS

International Invitation to Pay Additional Fees; Communication Relating to the Results of the Partial International Search; and Provisional Opinion Accompanying the Partial Search Result, dated Jan. 3, 2019 for Application No. PCT/IB2018/001018, 13 pgs.
International Search Report and Written Opinion dated Apr. 9, 2019 for Application No. PCT/IB2018/001018, 19 pgs.
International Search Report and Written Opinion dated Oct. 11, 2019 for Application No. PCT/IB2019/000497, 16 pgs.
Brazilian Office Action dated Jun. 5, 2023 for Application No. BR112021005339-5, 4 pages.
European Search Report dated Nov. 19, 2021 for Application No. 21189160.1, 12 pages.
European Extended Search Report dated Feb. 18, 2022 for Application No. 21189160.1, 13 pages.
Chinese Second Office Action dated Feb. 8, 2022 for Application No. 201880067229.3, 7 pages.
Japanese Office Action dated Aug. 10, 2021 for Application No. 2020-509446, 2 pages.
Japanese Office Acton dated May 24, 2022 for Application No. 2020-509449, 4 pages.
Japanese Office Action dated May 23, 2023 for Application No. 2021-149014, 2 pages.

* cited by examiner

HEAD STABILIZATION SYSTEM WITH ADJUSTABLE-FILL PADS AND METHOD OF USE

PRIORITY

This application claims priority to U.S. Provisional Patent Application No. 62/662,874, entitled "Head Stabilization System and Method with Arc Features," filed Apr. 26, 2018, and U.S. Provisional Patent Application No. 62/662,855, entitled "Head Stabilization System and Method with Cassette Features," filed Apr. 26, 2018, the disclosures of which are incorporated by reference herein.

BACKGROUND

The systems and methods disclosed pertain to the field of patient stabilization, and in particular head and neck stabilization using stabilization devices known as head stabilization devices which are also referred to as head fixation devices (hereinafter referred to as "HFDs" or "HFD" in singular). HFDs are sometimes used during a variety of surgical and other medical procedures, for example during head or neck surgery or testing where it would be desirable to securely support a patient's head in a certain position. Because a patient may need to be positioned in a certain way for procedure or preference reasons, not all HFDs may be best-suited to provide the necessary patient stabilization. While a variety of stabilization devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
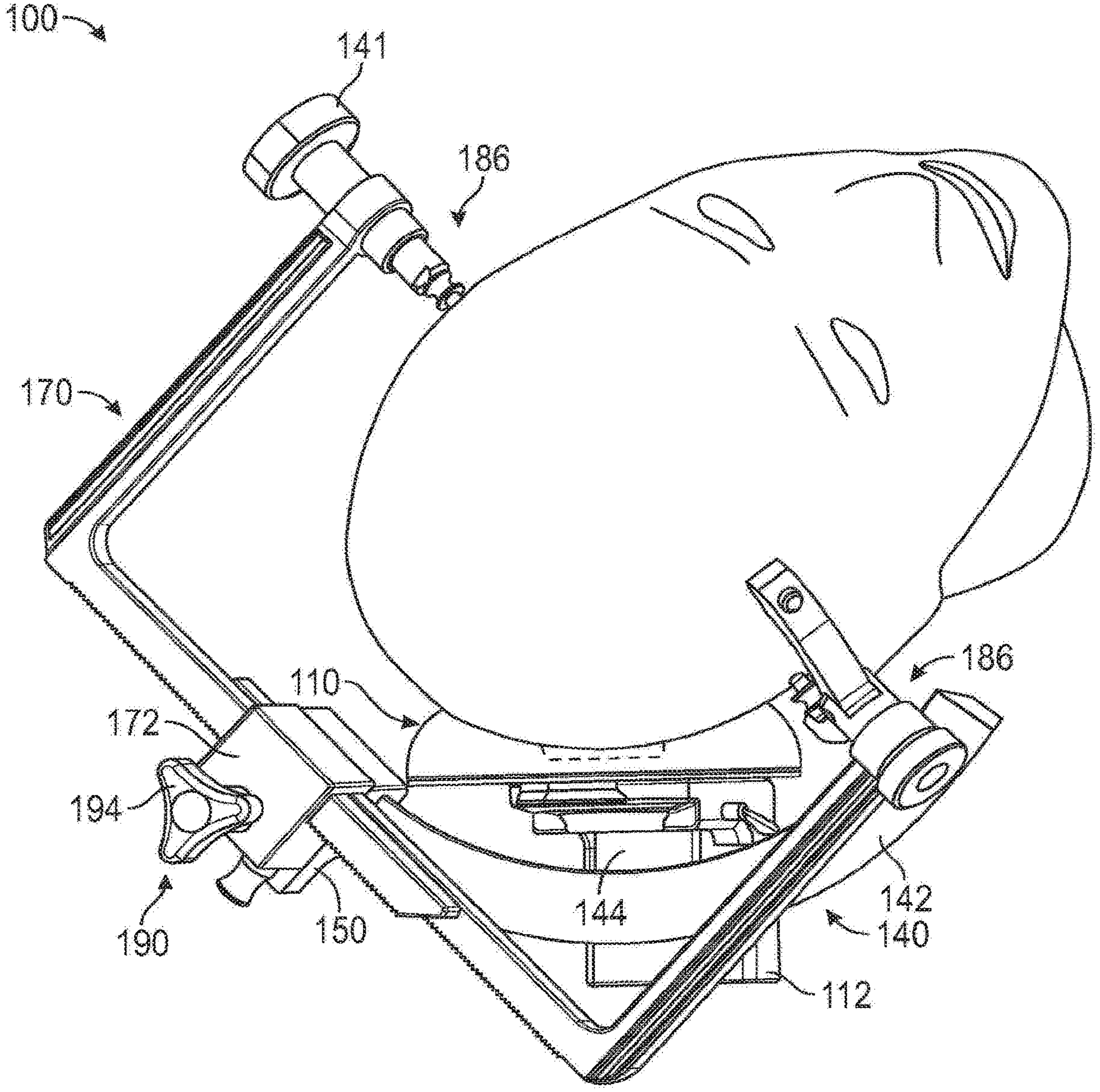
FIG. 1 depicts a perspective view of an exemplary HFD having an arc feature.
Figure 2:
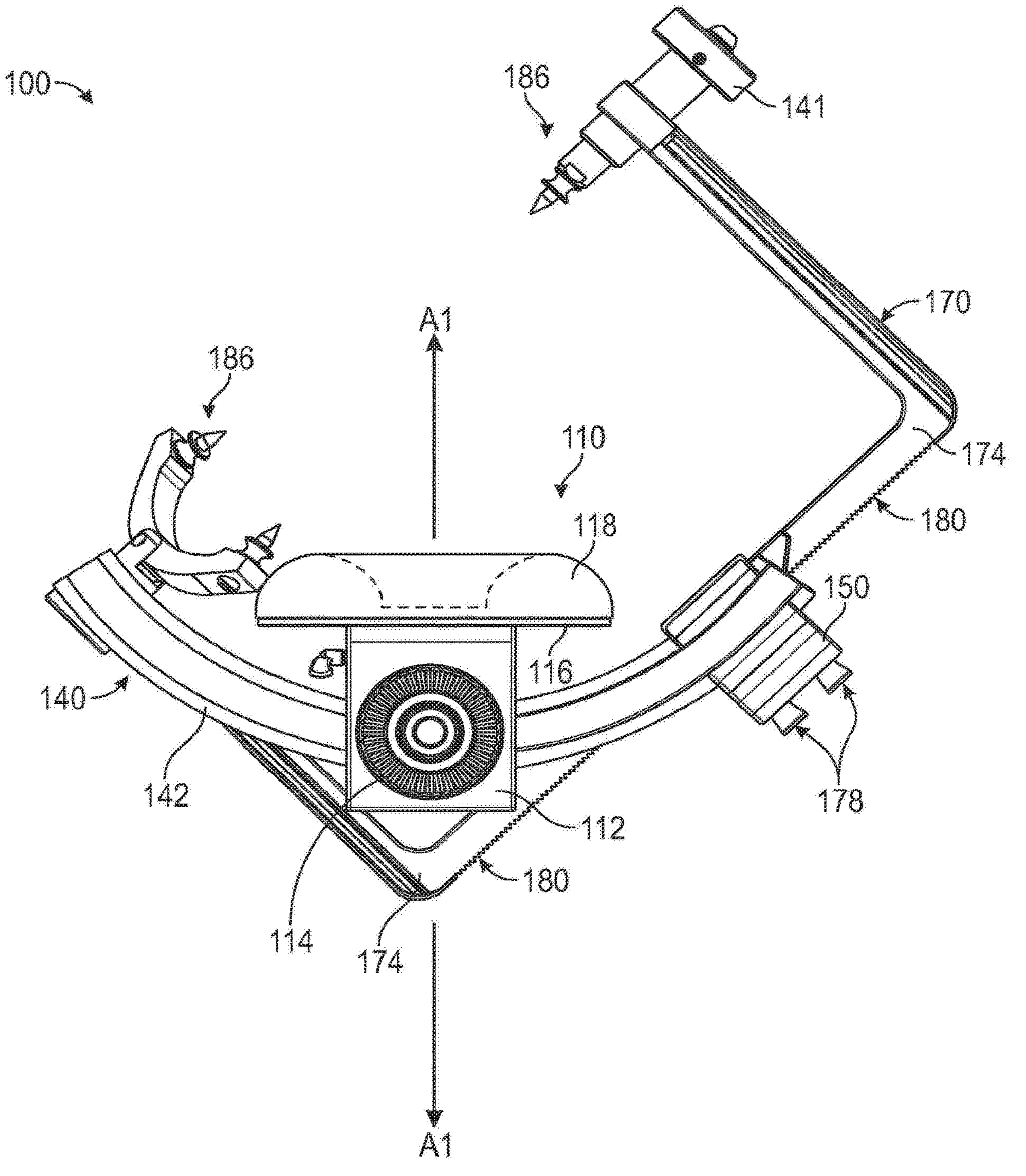
FIG. 2 depicts a front view of the HFD of FIG. 1.
Figure 3:
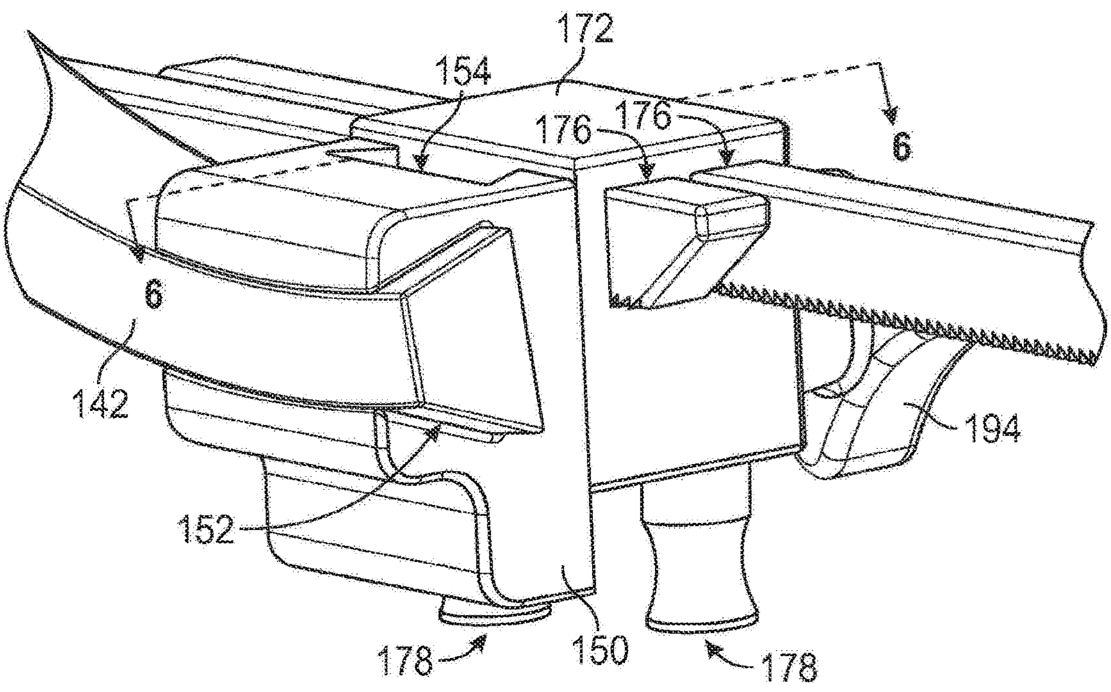
FIG. 3 depicts a top partial perspective view of the HFD of FIG. 1.
Figure 4:
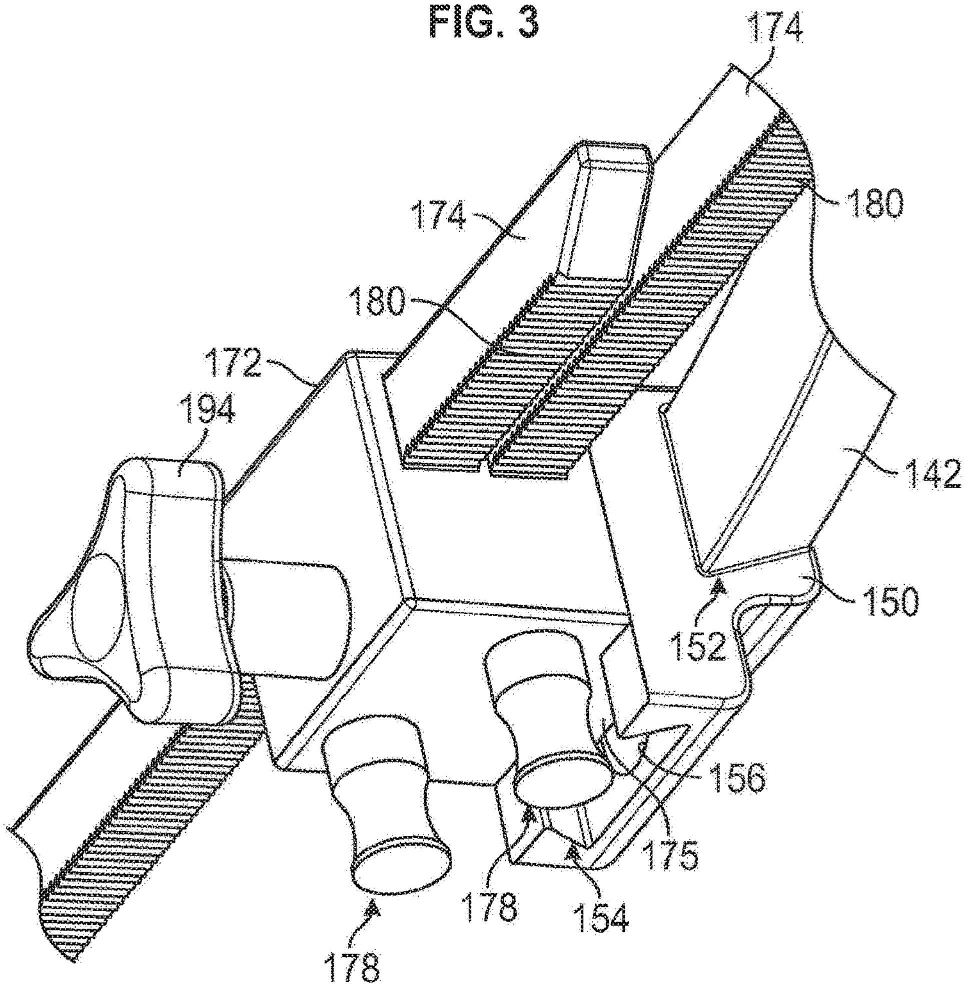
FIG. 4 depicts bottom partial perspective view of the HFD of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

I. Exemplary Head Fixation Device with Arc Feature

During certain medical procedures, it may be necessary or desirable to stabilize a patient's head using a HFD. It can be desirable to position the patient in a manner to provide the best access to the medical team and their equipment. This may involve the patient being in a prone position, in a supine position, or in an intermediate position where the patient's head is rotated left or right from the sagittal plane that defines a left side and a right side of the patient. When accommodating these and other positions for stabilizing a patient's head, adjustability of the HFD itself is a factor in stabilizing the patient securely so that movement or slippage of the patient's head is avoided. Referring now to the figures, FIGS. 1-5 illustrate an exemplary HFD (100) configured for use in supporting and stabilizing a head of a patient during a medical procedure. The HFD (100) comprises a central head support (110), an arc member (140), a skull clamp (170), and an actuator (190).

The central head support (110) comprises a body (112) and an attachment feature (114) on the body (112), where the attachment feature (114) is in the form of a starburst configured to connect with an operating table or other structure directly or indirectly via one or more intermediate structures. For example, in some instances a base unit, such as those available from pro med instruments GmbH, attaches to an operating table and the attachment feature (114) connects with the base unit. In some instances an adapter, such as a swivel adapter or other adapter available from pro med instruments GmbH, may connect with the base unit, and the attachment feature (114) of the central head support (110) connects with the adapter. In view of the teachings herein, various ways to connect the central head support (110) with a stable structure such as an operating table, etc. will be apparent to those of ordinary skill in the art.

The central head support (110) also comprises a base (116) that connects with the body (112) and that holds or retains a cushion (118). The cushion (118) may connect with the base (116) by way of an adhesive, mechanical fasteners such as screws or hook and loop, or other ways that will be apparent to those of ordinary skill in the art. In some versions, the cushion (118) is selectively connected with the base (116) such that the cushion (118) may be disposable or may be removed for cleaning and sterilization after use. The cushion (118) is configured to contact the head of the patient when the HFD (100) is used to support and stabilize the patient. In the present example of FIG. 7, the base (116) connects with the body (112) by way of a disc (120), which is connected with the base (116) using fasteners such as screws or bolts, etc. The disc (120) is received within a slot (122) defined in the body (112). In some versions, the disc (120) is configurable to be rotatable within the slot (122) such that the attached base (116) and cushion (118) are rotatably adjustable.

In use, the central head support (110) is configured to provide subjacent support to the head of the patient. In this manner, the central head support (110) defines a plane that extends subjacent to the head of the patient when the head of the patient is supported by the central head support. In the present example, the central head support (110) is positioned such that the plane defined by the central head support (110) is parallel to a floor, or orthogonal to a direction of gravitational force on the central head support (110). Furthermore, the central head support (110) defines a central axis (Al) that extends through the center of the cushion (118) and parallel with the direction of gravitation force on the central head support (110).

The arc member (140) of the HFD (100) connects with the central head support (110). In the present example the arc member (140) comprises a curved elongated member (142) and a connector (144) that is formed unitarily with the curved elongated member (142). In some other versions, the connector (144) connects with the elongated member (142) by removable fasteners such as screws, bolts, etc. In view of the teachings herein, other ways to connect the arc member (140) with the central head support (110) will be apparent to those of ordinary skill in the art. The connector (144) connects the arc member (140) with the body (112) of the central head support (110) as will be described in further detail below.

The elongated member (142) of the arc member (140) defines a curved shape having an arc length. With this configuration, the arc member (140) further defines a radius of curvature that represents the distance along the central axis (A1) from a center point of a patient's head when positioned on the cushion (118) to a point at the middle of the cross section of the elongated member (142). In the present example, the arc length is sufficient to allow positioning the skull clamp (170) in either direction along the arc member (140) up to about forty-five degrees offset from the central axis (A1) defined by the central head support (110). This positioning of the skull clamp (170) will be described in greater detail below. By way of example only, and not limitation, in some examples the arc member (140) can have an arc length between about 200 and about 350 millimeters and define a radius of curvature between about 120 and about 200 millimeters. For instance, in one example the arc member (140) defines a radius of curvature of about 152 millimeters with an arc length of about 293 millimeters. Of course these specific dimensions are not required in all versions and other suitable dimensions will be apparent to those of ordinary skill in the art in view of the teachings herein.

The curved elongated member (142) of the arc member (140) is configured with a trapezoidal shaped profile in the present example. This shape of the arc member (140) permits the arc member (140) to engage with a position adapter (150) that has a complementary shaped slot (152) configured to receive the arc member (140). In the present example, the slot (152) of the position adapter (150) and the profile of the elongated member (142) of the arc member (140) form a curved dovetail shaped interface. In view of the teachings herein, other complementary shapes for slot (152) and the arc member (140) profile that may be used will be apparent to those of ordinary skill in the art.

The skull clamp (170) is connectable with the arc member (140) such that the skull clamp (170) is selectively moveable or adjustable along the arc member (140). In the present example, the skull clamp (170) connects indirectly with the arc member (140) via the position adapter (150), however, in other versions the HFD (100) may be modified such that the skull clamp (170) directly connects with the arc member (140). By moving or adjusting the skull clamp (170) along the arc member (140), the position of the skull clamp (170) is adjustable relative to the central head support (110). Furthermore, when a patient's head is supported by the central head support (110), in at least some examples, movement of the skull clamp (170) along the arc member (140) alters a position of the skull clamp (170) concentrically, or substantially concentrically, about the head of the patient. In similar terms, a patient defines a sagittal plane that divides the patient into left and right sides, and an axis that extends longitudinally along the sagittal plane is considered a longitudinal axis defined by the patient. Generally this longitudinal axis extends from the head of the patient to the foot of the patient. In at least some examples, movement of the skull clamp (170) along the arc member (140) alters a position of the skull clamp (170) about this longitudinal axis defined by the patient. As mentioned above, in some instances the skull clamp (170) is adjustable in either direction relative to the central head support (110) and the patient's longitudinal axis up to about forty-five degrees from the central axis (A1) defined by the central head support (110). In this manner, the HFD (100) permits semi-lateral positioning of the skull clamp (170) on either side of the head of the patient supported by the central head support (110) up to about forty-five degrees. In view of the teachings herein, those of ordinary skill in the art will appreciate that the arc length of the arc member (140) could be lengthened such that position adjustments for the skull clamp (170) of greater than about forty-five degrees may be achieved.

The skull clamp (170) comprises a locking member (172), and a pair of extension bars (174). The locking member (172) comprises a pair of openings (176) configured to receive the extension bars (174). The extension bars (174) are independently moveable relative to the locking member (172) and each other. Furthermore, the locking member (172) comprises a pair of locks (178) that are configured to engage a respective extension bar (174) to either secure the extension bar (174) in position or permit adjustment of the extension bar (174). In this manner, each extension bar (174) comprises a toothed rack (180) and each lock (178) comprises a complementary shaped toothed portion residing within the locking member (172) that is moveable to engage or disengage the toothed rack (180) with which it is associated. For instance, the locks (178) are initially biased by a spring or other structure such that the toothed portion will engage with the toothed rack (180) and thus lock or secure the position of the extension bar (174) relative to the locking member (172). Each lock (178) may be pulled downward or away from the locking member (172) to disengage the toothed portion of the lock (178) from the toothed rack (180) and thereby permit lateral movement of the extension bar (174) relative to the locking member (172) and the other extension bar (174).

In the present example, the extension bars (174) are interchangeable such that one may replace the other in terms of its position within the locking member (172). Each extension bar (174) further comprises an upper end portion (182) having a bore (184) configured to receive a stabilizing assembly (186). The stabilizing assemblies (186) are configured to contact the head of the patient and provide lateral support and stabilization to the head of the patient. In the present example, the stabilizing assembly (186) may take the form of a single pin or a dual pin assembly. Furthermore, the stabilizing assembly (186) may include a torque screw (141) for adjusting the pressure applied to the patient's head by the stabilizing assemblies (186). In other versions, stabilizing assemblies (186) may take the form of a single or multi-chamber pad. Returning to the present example, each extension bar (174) comprises an upright portion (188) and a base (189) with the upright portion (188) defining a longitudinal axis. In the present example, each respective bore (184) is offset from the longitudinal axis defined by the upright portion (188) of each respective extension bar (174). Furthermore, when the extension bars (174) are positioned within the locking member (172) the bores (184) are offset in opposite directions such that they align and share a common axis (A2) that extends through each bore (184). Additionally, each of the extension bars (174) defines a rail configured to receive one or more accessories positionable along at least a portion of the extension bar (174).

As mentioned above, the skull clamp (170) connects with the arc member (140). In the present example, the locking member (172) of the skull clamp (170) connects with the position adapter (150), which then connects with the arc member (140) as described above. The connection between the position adapter (150) and the locking member (172) uses a dovetail connection in the present example. In this manner, the position adapter (150) comprises a slot (154) configured to receive a protrusion (175) of the locking member (172). In the present example, the protrusion has a trapezoidal shaped profile and the slot (154) has a complementary profile shape such that the protrusion (175) is receivable within the slot (154).

The connection between the position adapter (150) and the locking member (172) is selectively adjustable. More specifically, the locking member (172) can be adjusted vertically or longitudinally relative to the position adapter (150). This adjustment allows the distance between the stabilizing assemblies (186) of the skull clamp (170) and the central head support (110) to be adjusted. For instance, depending on the orientation of the patient, the head size of the patient, or other parameters, the skull clamp (170) and its associated stabilizing assemblies (186) may need moved closer or further from the central head support (110).

In further terms describing the adjustment between the position adapter (150) and the locking member (172), a sidewall (158) of the position adapter (150) defines a plane, and the locking member (172) is adjustable in a translating fashion along this plane. This movement or adjustment of the locking member (172) relative to the position adapter (150) changes the spacing of the locking member (172) and its connected components relative to the central head support (110) as mentioned above.

The actuator (190) of the HFD (100) is configured to selectively secure the position of the skull clamp (170) along the arc member (140). The actuator (190) is also configured to selectively secure the position of the skull clamp (170) relative to the central head support (110) by selectively securing the position of the skull clamp (170) relative to the position adapter (150). In the present example, this dual securing feature of the HFD (100) provides for selectively securing both the position of the skull clamp (170) along the arc member (140) and relative to the central head support (110) substantially simultaneously.

Figure 6:
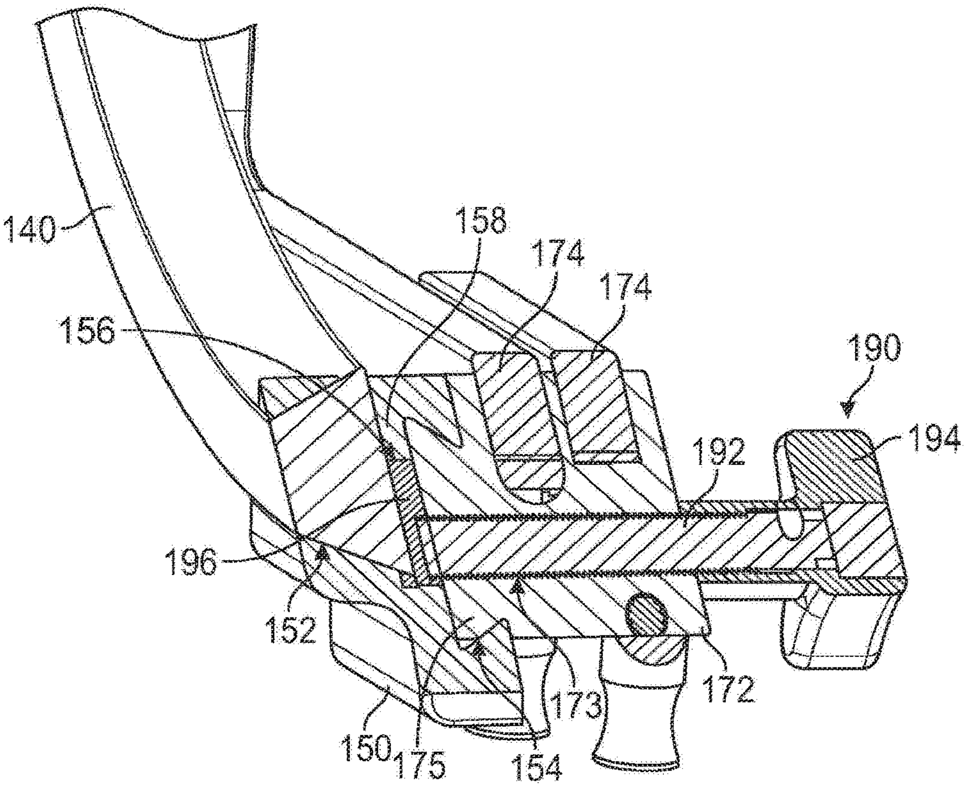
FIG. 6 depicts a partial section view of the HFD of FIG. 1 taken along line 6-6 of FIG. 3.

Referring to FIG. 6, the actuator (190) comprises a threaded rod (192) connected with a knob (194). The locking member (172) comprises a threaded bore (173) configured to receive the threaded rod (192) of the actuator (190). The threaded bore (173) extends all the way through the locking member (172) from one side to the other. In the present example, the threaded bore (173) extends through the protrusion (175). The actuator (190) further comprises a compression plate (196) that is positionable within a cut-out (156) of a sidewall (158) of the position adapter (150). On one side, the sidewall (158) containing the cut-out (156) defines a portion of the slot (154) that receives the protrusion (175) of the locking member (172). On the opposite side, the sidewall (158) containing the cut-out (156) defines a portion of slot (152) that receives the arc member (140). In this manner, the cut-out (156) connects the slots (152, 154) of the position adapter (150).

In use, rotating the knob (194) of the actuator (190) translates the locking member (172) toward or away from the position adapter (150) depending on the direction the knob (194) is rotated based on the threaded engagement between the threaded rod (192) and the threaded bore (173). By translating the locking member (172) away from the position adapter (150), the end of the threaded rod (192) contacts the compression plate (196) residing within the cut-out (156) and drives the compression plate (196) toward the arc member (140) residing within the slot (152) of the position adapter (150). The compression plate (196) is keyed to the cut-out (156), or dimensioned to match the cut-out (156), such that with sufficient rotation of the actuator (190), the compression plate (196) binds against the arc member (140) to secure the position adapter (150) relative to the arc member (140).

In this same manner, with the movement of the protrusion (175) of the locking member (172) away from the position adapter (150), the protrusion (175) binds against the sidewall of the slot (154) to secure the locking member (172) relative to the position adapter (150). With this locking and unlocking arrangement, the skull clamp (170) can be adjusted relative to the arc member (140) and relative to the central head support (110) with minimal rotation of the knob (194) of the actuator (190). For instance, by way of example only, and not limitation, in one version the HFD (100) can be moved from an adjustable to a fixed state with as little as one quarter rotation of the knob (194) of the actuator (190). Of course in other versions, the HFD (100) may be configured such that greater or less rotation of the actuator (190) may be used to move the HFD (100) from an adjustable to a fixed state.

Figure 7:
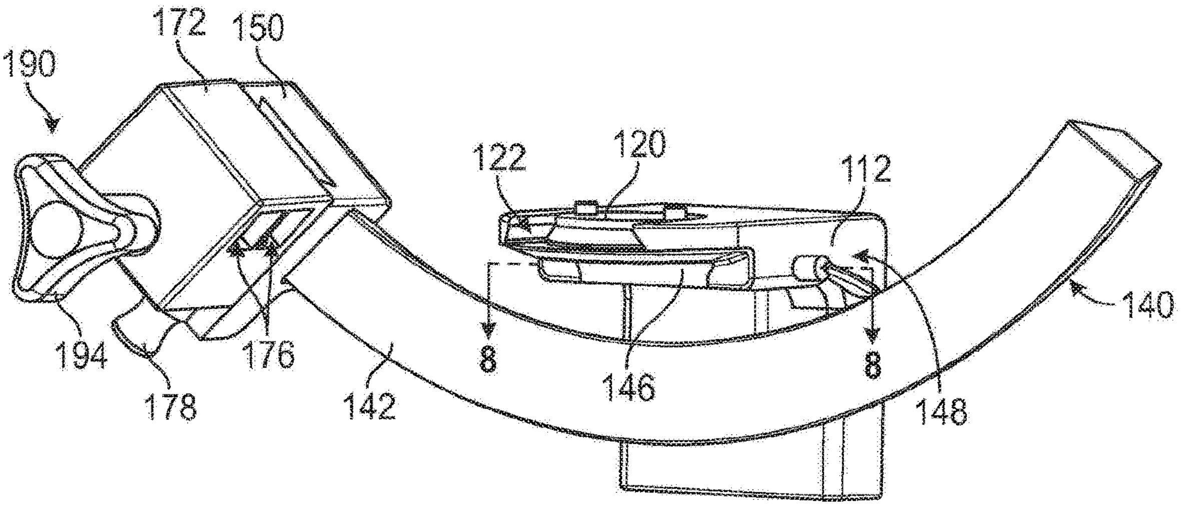
FIG. 7 depicts a partial perspective view of the HFD of FIG. 1, shown with certain components removed to better illustrate portions of a central head support.
Figure 8:
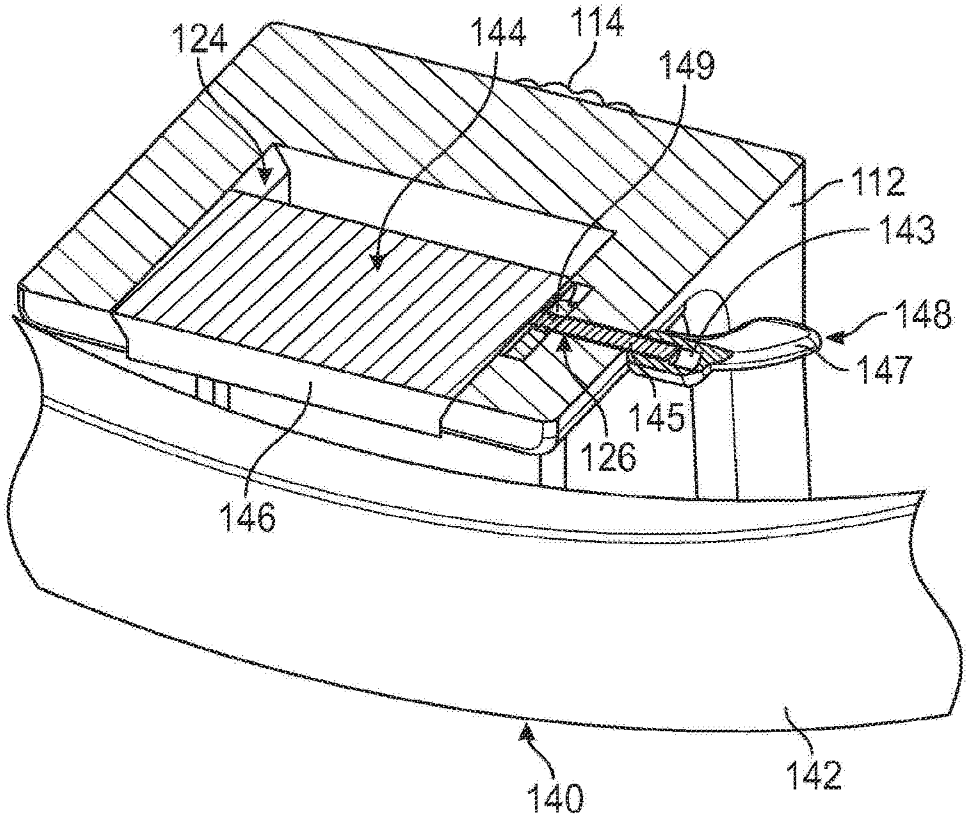
FIG. 8 depicts a partial section view of the HFD of FIG. 1 taken along line 8-8 of FIG. 7.

Referring to FIGS. 7 and 8, the central head support (110) is configured to adjust a spacing between the central head support (110) and the arc member (140). As mentioned above, the arc member (140) comprises the connector (144). The connector (144) adjustably connects with the body (112) of the central head support (110). As illustrated, within the body (112) is a slot (124). In the present example the slot (124) is positioned beneath the slot (122) that receives the disc (120). The slot (124) receives a portion of the connector (144). As shown, the connector (144) comprises an upper beam portion (146) that is configured to be received within the slot (124). The profile of the beam portion (146) has a complementary shape to the slot (124). In the present example the beam portion (146) and slot (124) together form a dovetail interface. In this manner the connector (144) is translatable along the slot (124), which adjusts the spacing between the arc member (140) and the central head support (110).

To control the adjustability of the connector (144) within the slot (124), the central head support (110) comprises an actuator (148) that includes a lock feature (149) that contacts the beam portion (146) to either secure its position relative to the body (112) via a compression engagement, or permit slidable adjustment of the connector (144) relative to the body (112) by the lock feature (149) disengaging from contacting the beam portion (146) at least sufficiently to permit translational movement of the connector (144). To control the contact of the lock feature (149) with the beam portion (146), the actuator (148) includes a lever (147) that is rotated. Rotation of the lever (147) causes the lock feature (149) to move toward or away from the beam portion (146) depending on the direction the lever (147) is rotated. The actuator (148) includes a threaded rod (145) that extends through a threaded bore (126) in the body (112) of the central head support (110). The lever (147) includes a bore (143) connected to the threaded rod (145) in a fixed manner such that the lever (147) and the threaded rod (145) rotate in unison. Rotating the lever (147) rotates the threaded rod (145), which causes the threaded rod (145) to translate toward or away from the beam portion (146) based on the direction of rotation. The translation of the threaded rod (145) toward the beam portion (146) drives the lock feature (149) into contact with the beam portion (146) of the connector (144) to thereby secure the position of the connector (144) and thus the arc member (140) relative to the central head support (110). Similarly, the translation of the threaded rod (145) away from the beam portion (146) causes the lock feature (149) to disengage with the beam portion (146) of the connector (144) to thereby allow adjustment of the position of the connector (144) and thus the arc member (140) relative to the central head support (110). In the configuration described above, the connector (144) is adjustable along or parallel to the plane defined by the central head support (110) to change a position of the arc member (140) relative to the central head support (110).

II. Exemplary Head Fixation Device with Unidirectional Arc

Figure 9:
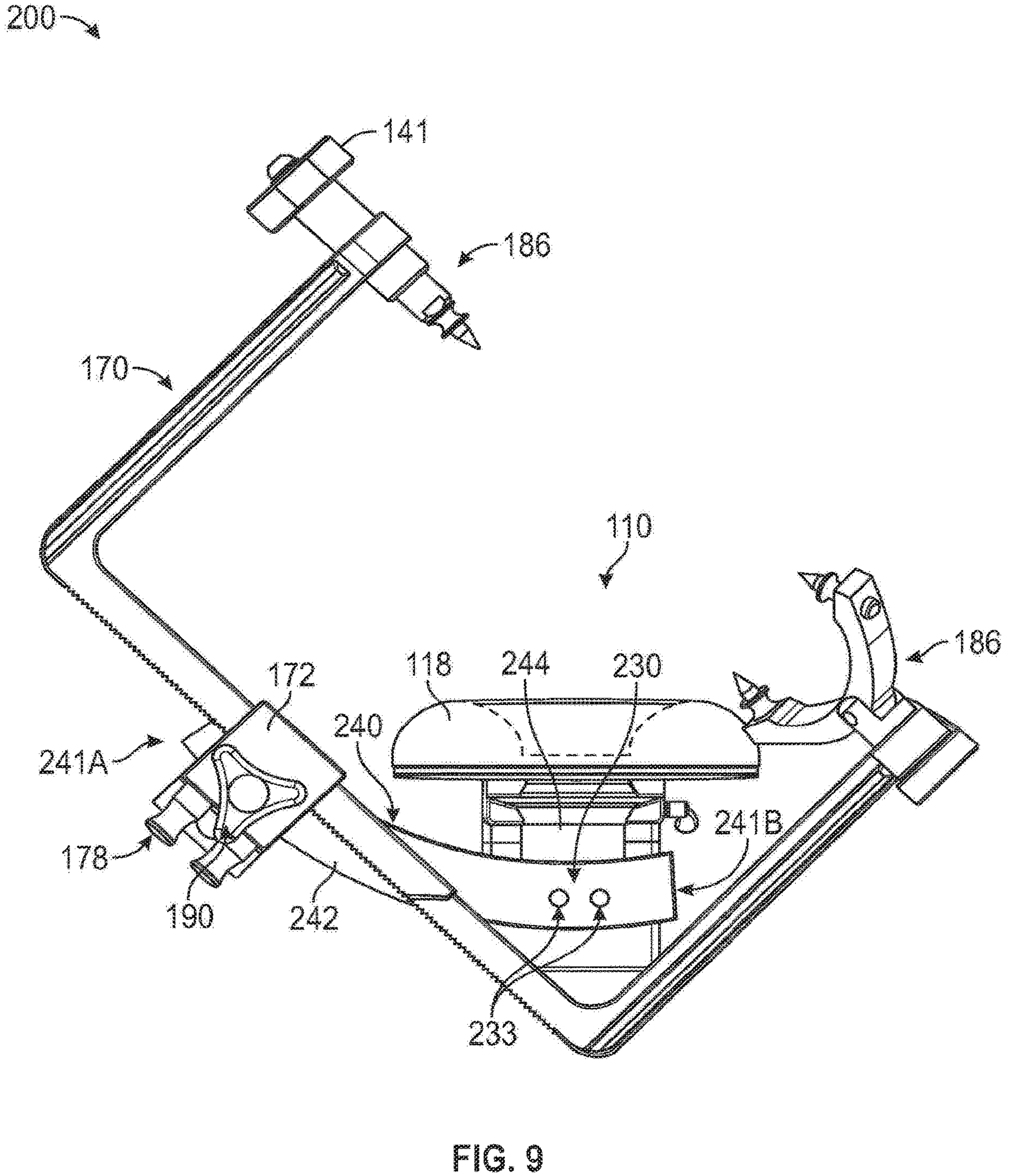
FIG. 9 depicts a rear view of another exemplary HFD having a unidirectional arc feature.
Figure 10:
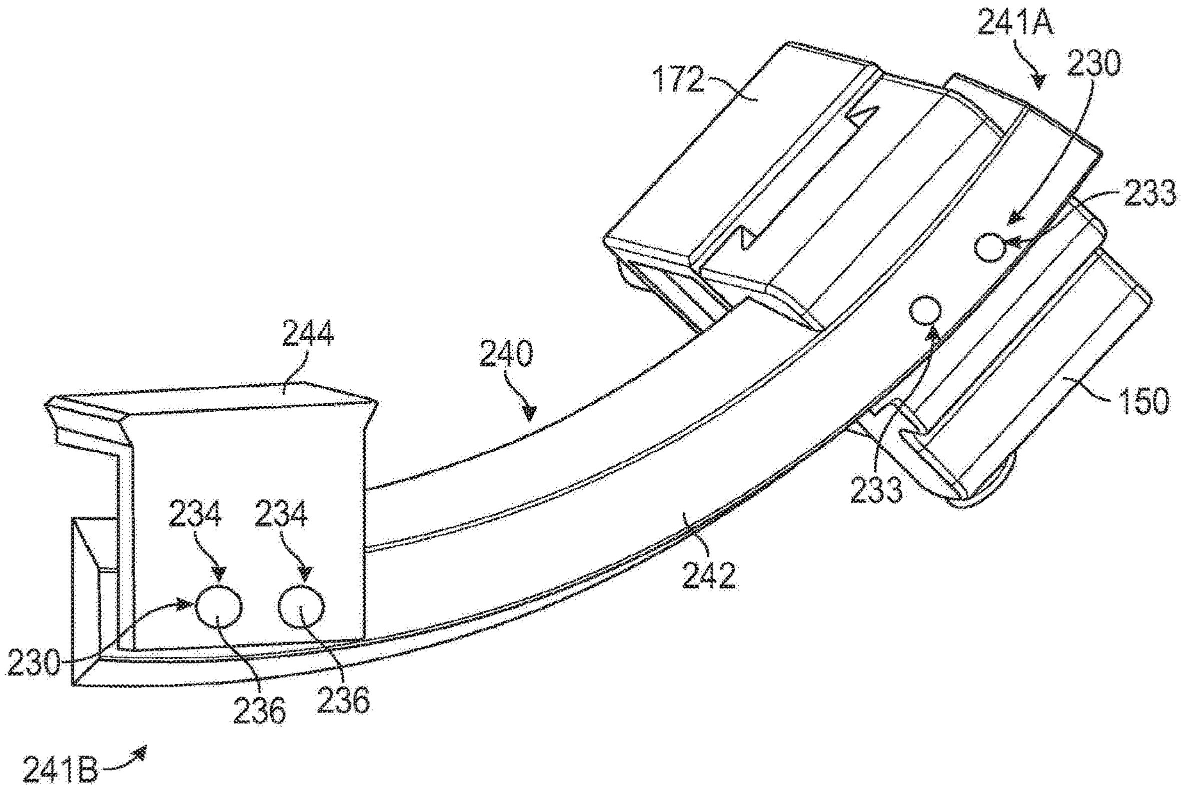
FIG. 10 depicts a partial perspective view of the arc member, position adapter, and locking member of the HFD of FIG. 9.

With certain medical procedures involving stabilization of a patient's head, especially those procedures where imaging is used through the procedure, it can be desirable to use HFDs with space saving designs. This can be based on the small spaces available within some imaging equipment, and/or this can be based on reducing the amount of material that may contribute to artifact in the imaging output. Referring to FIGS. 9 and 10, another exemplary HFD (200) is shown that is similar in many respects to the HFD (100), but that uses a shorter arc member thereby reducing the overall size and mass of the HFD (200). The features of the HFD (200) are the same as those described above with respect to the HFD (100) except as described below. Therefore, for the sake of brevity, the features of the HFD (100) described above apply equally to the HFD (200) with the exception of the below described differences.

The HFD (200) comprises the central head support (110), the skull clamp (170), and the actuator (190) as described above. However, with the HFD (200), an arc member (240) replaces the above-described arc member (140). The arc member (240) is configured as a unidirectional arc member. In other words, with the HFD (200), the arc member (240) extends from beneath the central head support (110) and outward in one direction along an arcuate path. In this manner, the connection between the central head support (110) and the arc member (240) is such that the central head support (110) connects with one end of the arc member (240), leaving the arc member (240) to extend away from the central head support (110) in a single direction.

In more specific terms, the arc member (240) comprises a curved elongated member (242) and a connector (244). In the present example, the curved elongated member (242) comprises a first end (241A) and a second end (241B). Proximate to each of the first end (214A) and the second end (241B) are a pair of attachment zones (230) with a pair of threaded bores (233) at each of the attachment zones (230). The connector (244) comprises a pair of threaded bores (234) as well, and a pair of fasteners (236) that extend through the pair of threaded bores (234) and that are configured to be received by one of the pair of threaded bores (233) in the curved elongated member (242). In this manner, the connector (244) is configured to attach with the elongated member (242) at either one of the attachment zones (230). As described above, with respect to the connector (144), the connector (244) connects with the central head support (110) in the same manner as does the connector (144).

In some instances the arc member (240) can be described as a half-arc instead of or in addition to a unidirectional arc. With this configuration, the curved elongated member (242) of the arc member (240) defines an arc length and a radius of curvature. As mentioned above, the radius of curvature represents the distance along the central axis (A1) from a center point of a patient's head when positioned on the cushion (118) to a point at the middle of the cross section of the elongated member (242). In the present example, the arc length is sufficient to allow positioning the skull clamp (170) in one direction along the arc member (240) up to about forty-five degrees offset from the central axis (A1) defined by the central head support (110). By way of example only, and not limitation, in some examples the arc member (240) can have an arc length between about 120 and about 200 millimeters, and define a radius of curvature between about 120 and about 200 millimeters. For instance, in one example the arc member (240) defines a radius of curvature of about 152 millimeters with an arc length of about 170 millimeters. Of course these specific dimensions are not required in all versions and other suitable dimensions will be apparent to those of ordinary skill in the art in view of the teachings herein.

The curved elongated member (242) of the arc member (240) is configured with a trapezoidal shaped profile in the present example. This shape of the arc member (240) permits the arc member (240) to engage with the position adapter (150), which that has a complementary shaped slot (152) configured to receive the arc member (240). In the present example, the slot (152) of the position adapter (150) and the profile of the elongated member (242) of the arc member (240) form a curved dovetail shaped interface. In view of the teachings herein, other complementary shapes for slot (152) and the arc member (240) profile that may be used will be apparent to those of ordinary skill in the art.

Figure 11:
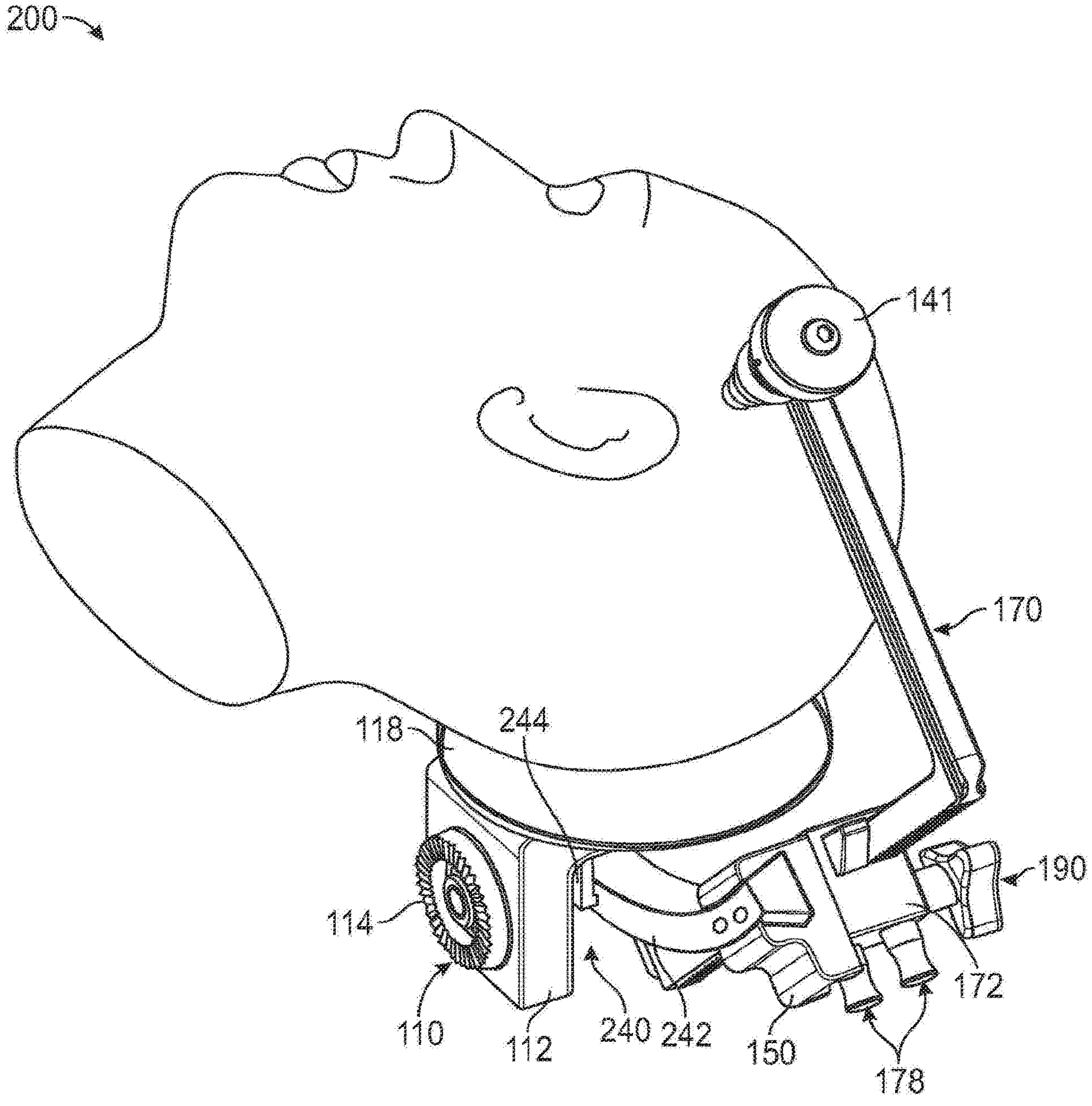
FIG. 11 depicts a perspective view of the HFD of FIG. 9 showing a patient's head stabilized with the skull clamp adjusted along the arc member.

When using the HFD (200), because of the unidirectional nature of the arc member (240), first the orientation of the patient is determined. For instance, will the patient's head rotate to one side or the other relative to the sagittal plane of the patient. Based on the direction of the patient's head rotation when supported by the central head support (110), the connector (244) of the arc member (240) will be attached with the curved elongated member (242) at either the attachment zone (230) near the first end (241A) or at the attachment zone (230) near the second end (241B). In one example, when the patient's head rotates in a first direction relative to the sagittal plane of the patient, the desired setup for the arc member (240) is such that the curved elongated member (242) extends opposite to the first direction. In this manner, the curved elongated member (242) extends away from the sagittal plane of the patient so that the curved elongated member (242) extends behind the head of the patient. By way of illustrative example only, and not limitation, FIG. 11 shows the HFD (200) used to stabilize a patient whose head is rotated in a first direction relative to the sagittal plane of the patient. The arc member (240) is configured such that the connector (244) attaches with the attachment zone (230) at the second end (241B) of the curved elongated member (242). In this manner, the curved elongated member (242) extends opposite to the first direction and away from the sagittal plane of the patient so that the curved elongated member (242) extends behind the head of the patient.

As described above, the skull clamp (170) connects with the arc member (240) in the same manner as the skull clamp (170) connects with the arc member (140). With the HFD (200), the skull clamp (170) is adjustable in one direction relative to the central head support (110) and the patient's longitudinal axis up to about forty-five degrees from the central axis (A1) defined by the central head support (110). In this manner, the HFD (200) permits semi-lateral positioning of the skull clamp (170) on one side of the head of the patient supported by the central head support (110) up to about forty-five degrees.

Additionally, because the connector (244) can connect to either end of the curved elongated member (242) of the arc member (240), the HFD (200) can be configured so that the arc member (240) extends away from the central head support (110) in either direction depending on the selected attachment location of the connector (244) with the curved elongated member (242). Consequently, the HFD (200) with the half arc or unidirectional arc member (240), can be configured for use with a patient that may be positioned with their head supported by the central head support (110) and rotated in either direction relative to the sagittal plane of the patient. Stated another way, with the HFD (200) the arc member (240) can be considered as connectable with the central head support (110) in a selected one of a first orientation and a second orientation. In the second orientation the arc member (240) extends outward from beneath the central head support (110) in a first direction, which is opposite to a second direction that the arc member (240) extends outward from beneath the central head support (110) when in the first orientation.

In some other versions of HFD (200) with the unidirectional arc or half arc, the HFD (200) may be modified such that the connection between the skull clamp and the arc member is configured to permit the skull clamp to attach with the arc member from either side of the skull clamp. In this manner, the attachment of the arc member and the skull clamp are considered symmetric. In view of the teachings herein, other ways to connect the skull clamp and the unidirectional arc member will be apparent to those of ordinary skill in the art.

III. Exemplary Head Fixation Device with Pressure Control Pivoting Cushion

Figure 12:
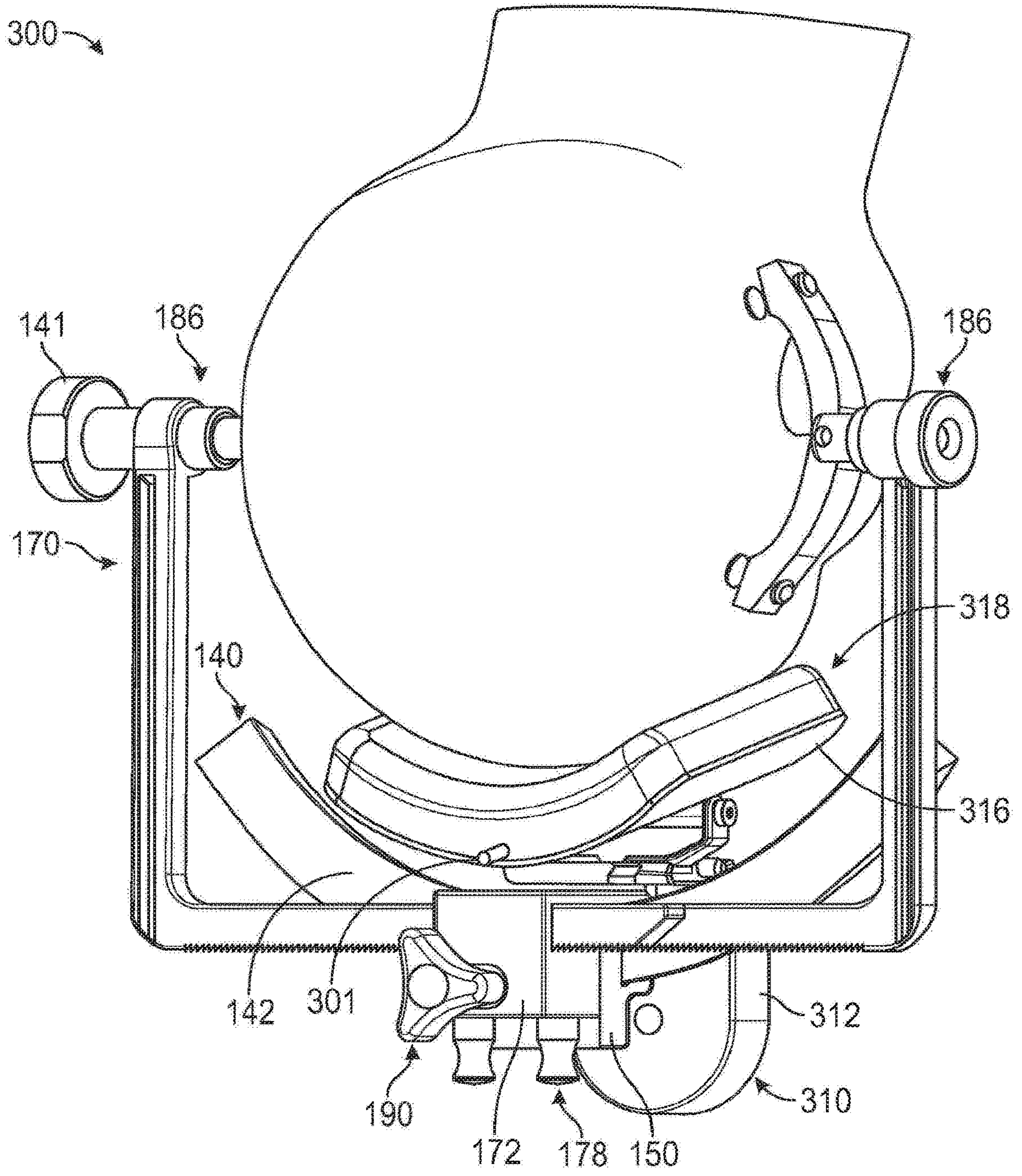
FIG. 12 depicts a perspective view of another exemplary HFD having a multi-chamber pivoting cushion.

In providing HFDs with ample adjustability to accommodate various patient positioning, another desirable feature can be to incorporate a selective pivot adjustment to the cushion of the HFD. Other features that can be incorporated into the cushion pertain to management or control of the contact pressure between the cushion and the patient. FIG. 12 depicts another HFD (300) that is similar in many respects to the HFD (100), but that incorporates features directed to a pivotable cushion and also incorporates features that aid in controlling contact pressure. The features of the HFD (300) are the same as those described above with respect to the HFD (100) except as described below. Therefore, for the sake of brevity, the features of the HFD (100) described above apply equally to the HFD (300) with the exception of the below described differences.

Figure 13:
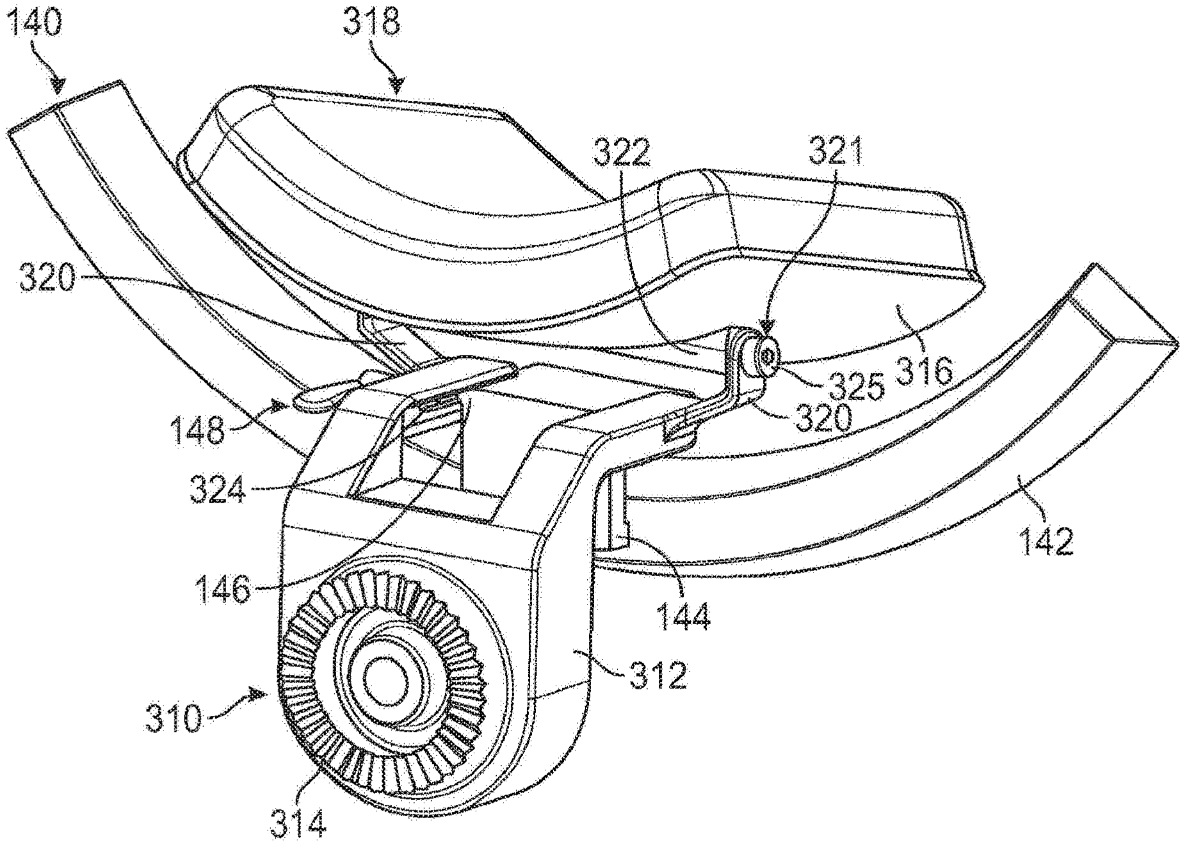
FIG. 13 depicts a partial perspective view of the HFD of FIG. 12, showing the central head support in greater detail.

The HFD (300) comprises the arc member (140), the skull clamp (170), and the actuator (190) as described above. However, with the HFD (300), a central head support (310) replaces the above-described central head support (110). Referring to FIGS. 12 and 13, the central head support (310) comprises a body (312) and an attachment feature (314) on the body (312), where the attachment feature (314) is in the form of a starburst configured to connect with an operating table or other structure directly or indirectly via one or more intermediate structures. For example, in some instances a base unit, such as those available from pro med instruments GmbH, attaches to an operating table and the attachment feature (314) connects with the base unit. In some instances an adapter, such as a swivel adapter or other adapter available from pro med instruments GmbH, may connect with the base unit, and the attachment feature (314) of the central head support (310) connects with the adapter. In view of the teachings herein, various ways to connect the central head support (310) with a stable structure such as an operating table, etc. will be apparent to those of ordinary skill in the art.

The central head support (310) also comprises a base (316) that connects with the body (312) and that holds or retains a cushion (318). The cushion (318) may connect with the base (316) by way of an adhesive, mechanical fasteners such as screws or hook and loop, or other ways that will be apparent to those of ordinary skill in the art. In some versions, the cushion (318) is selectively connected with the base (316) such that the cushion (318) may be disposable or may be removed for cleaning and sterilization after use. The cushion (318) is configured to contact the head of the patient when the HFD (300) is used to support and stabilize the patient. In the present example, the base (316) connects with the body (312) by way of a pair of arms (320) that extend from the body (312) outward and upward. The base (316) comprises a connection member (322) defining an axis extending transversely across the base (316). The connection member (322) comprises a pair of bores (323) and each bore (323) of the pair aligns with a respective bore (321) in each of the arms (320). The axis defined by the connection member (322) extends along the bores (323) of the connection member (322) such that the axis defines a pivoting axis about which the base (316) and connected cushion (318) are pivotable. A pair of fasteners (325) extend through the bores (321) of the arms (320) and engage the bores (323) of the connection member (322) to pivotably connect the base (316) with the body (312) of the central head support (310). The fasteners (325) may be tightened to secure the position of the base (316) and connected cushion (318), and conversely the fasteners (325) may be loosened to permit pivotable adjustment of the base (316) and connected cushion (318).

Figure 15:
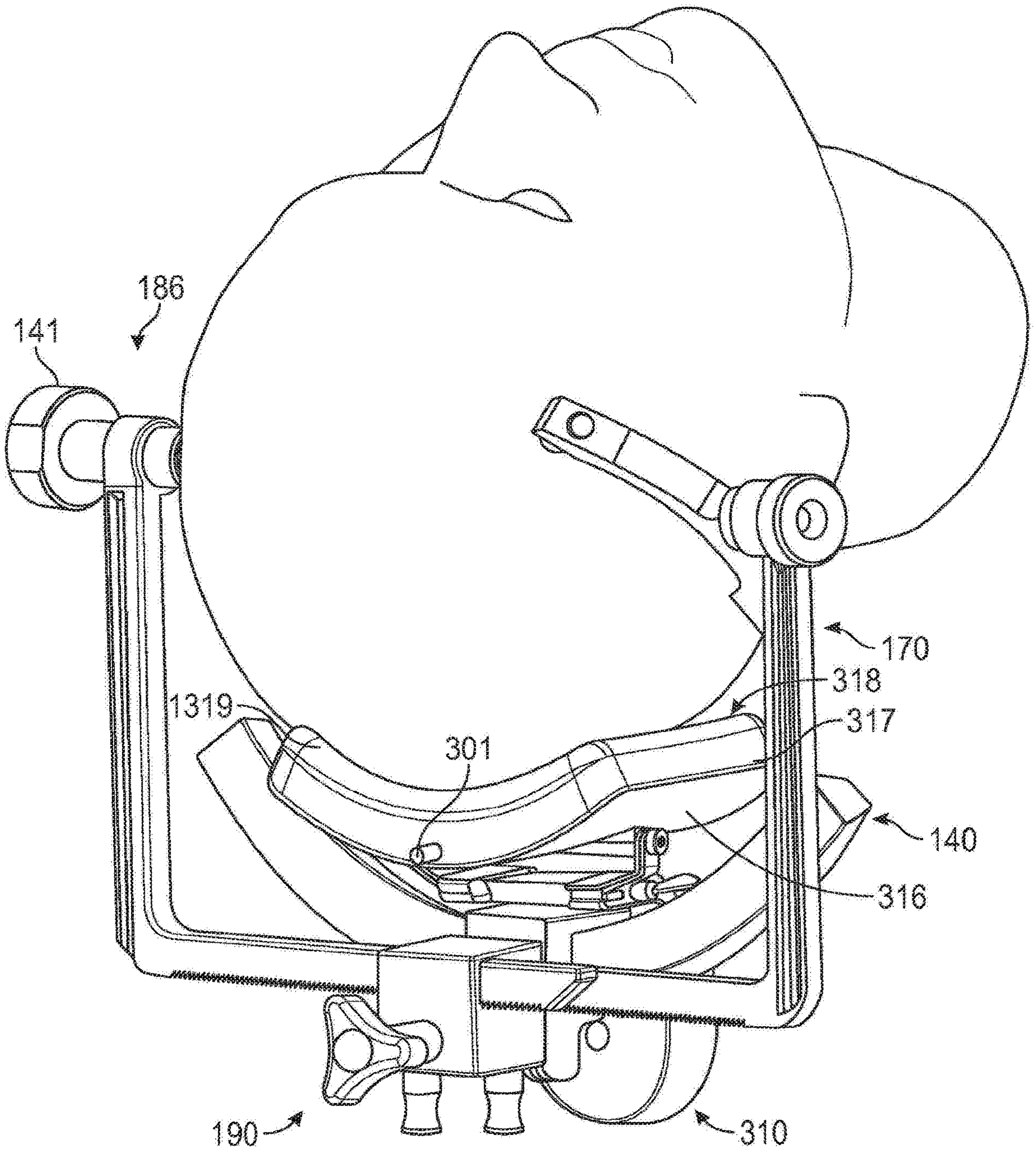
FIG. 15 depicts another perspective view of the HFD of FIG. 12, shown with the patient's head stabilized in a supine position.

In use, the central head support (310) is configured to provide subjacent support to the head of the patient. In this manner, the central head support (310) defines a plane that extends subjacent to the head of the patient when the head of the patient is supported by the central head support. In the present example, the central head support (310) is positioned such that the plane defined by the central head support (310) may be adjusted based on the pivoting action of the base (316) and connected cushion (318). Therefore, the plane defined by the central head support (310) is not limited to being parallel to a floor, or orthogonal to a direction of gravitational force on the central head support (310). Referring to FIGS. 12 and 15, the HFD (300) is shown with the base (316) pivoted to two different orientations to accommodate different position of a patient's head, i.e. a Concorde position like shown in FIG. 12 and a supine position like shown in FIG. 15.

Referring to FIG. 13, the central head support (310) is configured to adjust a spacing between the central head support (310) and the arc member (140). As mentioned above, the arc member (140) comprises the connector (144). The connector (144) adjustably connects with the body (312) of the central head support (310). As illustrated, within the body (312) is a slot (324). The slot (324) receives a portion of the connector (144). As shown, the connector (144) comprises an upper beam portion (146) that is configured to be received within the slot (324). The profile of the beam portion (146) has a complementary shape to the slot (324). In the present example the beam portion (146) and slot (324) together form a dovetail interface. In this manner the connector (144) is translatable along the slot (324), which adjusts the spacing between the arc member (140) and the central head support (310). To control the adjustability of the connector (144) within the slot (324), the central head support (310) comprises the actuator (148) and the lock feature (149) as described above with respect to the HFD (100). With the HFD (300), the actuator (148) and lock feature (149) are configured and operable in the same manner as described above with respect to the HFD (100). In this configuration, the connector (144) is adjustable along or parallel to the plane defined by the central head support (310) to change a position of the arc member (140) relative to the central head support (310).

Figure 14:
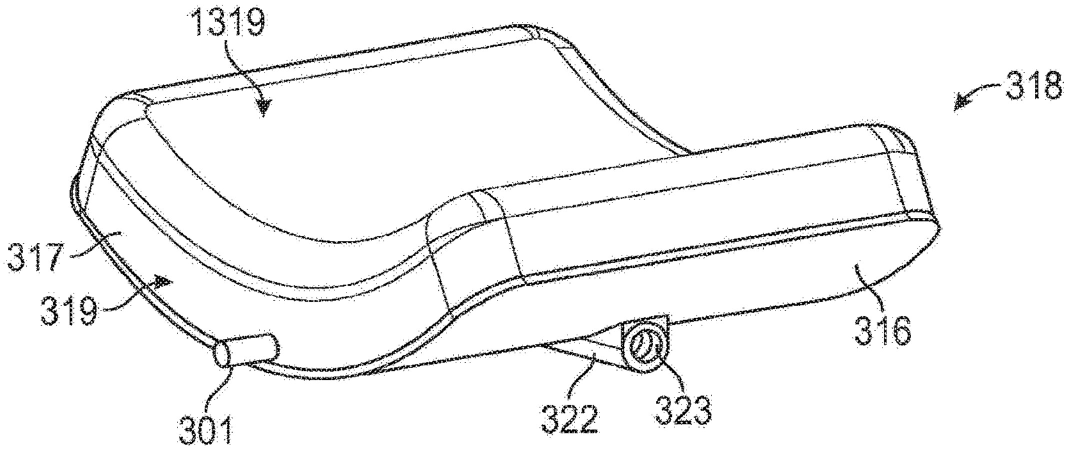
FIG. 14 depicts a perspective view of the base and the cushion of the central head support of the HFD of FIG. 12.

Referring to FIG. 14, the cushion (318) of the HFD (300) comprises a first chamber (319) having an internal space (317) that is configured to be filled with a fluid. The fluid may be a gas or a liquid. The first chamber (319) includes a port (301) that is configured to provide access to the internal space (317). The fluid may be directed to the internal space (317) within the first chamber (319) or extracted from or vented from the internal space (317) of the first chamber (319). When venting fluid from the first chamber (319), all or a portion of the fluid may be released or vented from the internal space (317).

The cushion (318) further comprises a second chamber (1319), which is configured to be filled with a shape-conforming material. In the present example, the first chamber (319) is positioned subjacent to the second chamber (1319). Furthermore, the second chamber (1319) is configured to contact the patient's head. In view of the teachings herein, it will be apparent to those of ordinary skill in the art that the relative positions of the first and second chambers (319, 1319) may be switched in other versions. In one version, the shape-conforming material is one of either a gel, a foam, or a granule material. In view of the teachings herein, other shape-conforming materials usable with the cushion (318) will be apparent to those of ordinary skill in the art.

With the configuration of the cushion (318) described above, the cushion (318) is configured to provide a uniform distribution of contact pressure with the head of the patient when the head is supported by the central head support (310). Moreover, the contact pressure can be increased by filling the first chamber (319) with fluid via the port (301). Conversely, the contact pressure can be decreased by venting the fluid from the first chamber (319) as mentioned above. By reducing the contact pressure, blood flow can be restored to the area of the patient's head in contact with the cushion (318). In some instances, but not required in all versions, substantial venting of the fluid from the first chamber (319) may cause the cushion (318) to deflate or reduce in height such that the cushion (318) no longer contact the head of the patient. Similar to above, by reducing the contact pressure to the extent that the contact between the cushion (318) and the patient is lacking, blood flow can be restored to the area of the patient's head that was in contact with the cushion (318). By reducing contact pressure and providing for restoration of blood flow, tissue trauma or injury can be avoided or the risk reduced. Additionally, stabilization can be maintained by the stabilization assemblies (186) when reducing contact pressure between the cushion (318) and the patient's head so as to not sacrifice stabilization of the patient when restoring blood flow to an area of tissue. In some instances, once sufficient time has elapsed to restore blood flow to the tissue area in contact with the cushion (318), the contact pressure can be increased again by filling the first chamber (319) with the fluid to provide or restore an enhanced or a greater degree of stabilization.

Figure 16:
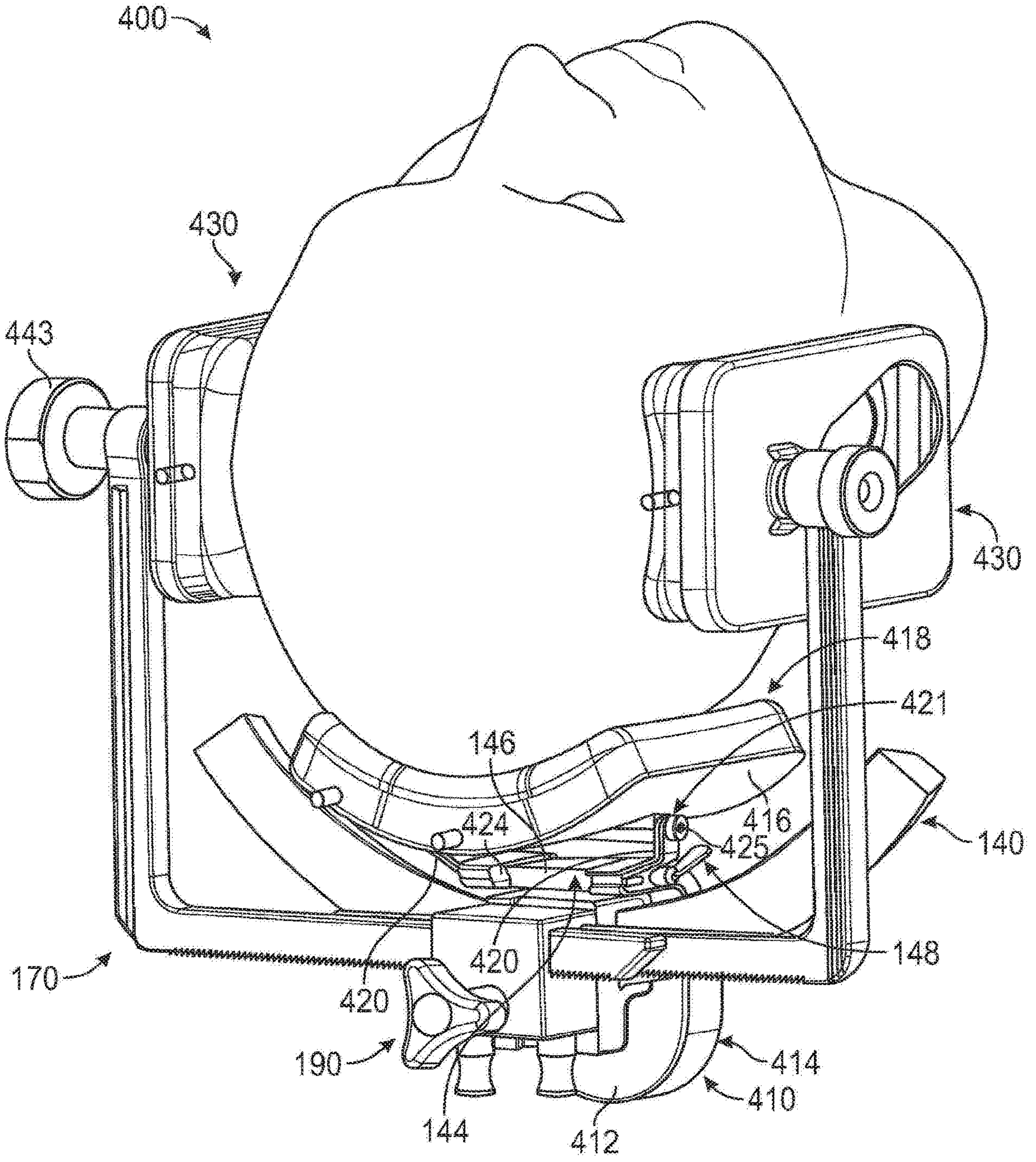
FIG. 16 depicts a perspective view of another exemplary HFD configured as a non-invasive HFD.

IV. Exemplary Non-Invasive Head Fixation Device with Lateral Pads and Multi-Chamber Cushion In some instances, a non-invasive HFD configuration may be desired where the stabilization assemblies have the form of pads instead of pins, where the pads provide the lateral stabilization. Additionally, the pads may be configured with certain contact pressure control features to help promote blood flow to certain tissue areas to avoid or reduce the risk of tissue injury or trauma. Referring to FIG. 16, an exemplary HFD (400) is shown that is similar in many respects to the HFD (100), but that incorporates pads (430) for the stabilization assemblies (186) to provide for a non-invasive stabilization. The HFD (400) also includes a pivotable cushion (418) similar in some respects to the cushion (318) as described with respect to the HFD (300). The HFD (400) further includes features that aid in controlling pressure at the stabilization contact areas where the pads (430) contact the patient's head and at the subjacent stabilization contact area where the cushion (418) contacts the patient's head. The features of the HFD (400) are the same as those described above with respect to the HFD (100) except as described below. Therefore, for the sake of brevity, the features of the HFD (100) described above apply equally to the HFD (400) with the exception of the below described differences.

The HFD (400) comprises the arc member (140), the skull clamp (170), and the actuator (190) as described above. The HFD (400) also comprises a central head support (410) that is similar to the central head support (310) as described above with respect to the HFD (300), however, the central head support (410) includes a cushion (418) instead of the cushion (318) described above. Referring to FIG. 16, the central head support (410) comprises a body (412) and an attachment feature (414) on the body (412), where the attachment feature (414) is in the form of a starburst configured to connect with an operating table or other structure directly or indirectly via one or more intermediate structures. For example, in some instances a base unit, such as those available from pro med instruments GmbH, attaches to an operating table and the attachment feature (414) connects with the base unit. In some instances an adapter, such as a swivel adapter or other adapter available from pro med instruments GmbH, may connect with the base unit, and the attachment feature (414) of the central head support (410) connects with the adapter. In view of the teachings herein, various ways to connect the central head support (410) with a stable structure such as an operating table, etc. will be apparent to those of ordinary skill in the art.

The central head support (410) also comprises a base (416) that connects with the body (412) and that holds or retains the cushion (418). The cushion (418) may connect with the base (416) by way of an adhesive, mechanical fasteners such as screws or hook and loop, or other ways that will be apparent to those of ordinary skill in the art. In some versions, the cushion (418) is selectively connected with the base (416) such that the cushion (418) may be disposable or may be removed for cleaning and sterilization after use. The cushion (418) is configured to contact the head of the patient when the HFD (400) is used to support and stabilize the patient. In the present example, the base (416) connects with the body (412) by way of a pair of arms (420) that extend from the body (412) outward and upward. The base (416) comprises a connection member (422) defining an axis extending transversely across the base (416). The connection member (422) comprises a pair of bores (423) on each side and each bore (423) of the pair aligns with a respective bore (421) in each of the arms (420). The axis defined by the connection member (422) extends along the bores (423) of the connection member (422) such that the axis defines a pivoting axis about which the base (416) and connected cushion (418) are pivotable. A pair of fasteners (425) extend through the bores (421) of the arms (420) and engage the bores (423) of the connection member (422) to pivotably connect the base (416) with the body (412) of the central head support (410). The fasteners (425) may be tightened to secure the position of the base (416) and connected cushion (418), and conversely the fasteners (425) may be loosened to permit pivotable adjustment of the base (416) and connected cushion (418).

In use, the central head support (410) is configured to provide subjacent support to the head of the patient. In this manner, the central head support (410) defines a plane that extends subjacent to the head of the patient when the head of the patient is supported by the central head support. In the present example, the central head support (410) is positioned such that the plane defined by the central head support (410) may be adjusted based on the pivoting action of the base (416) and connected cushion (418). Therefore, the plane defined by the central head support (410) is not limited to being parallel to a floor, or orthogonal to a direction of gravitational force on the central head support (410).

Referring to FIG. 16, the central head support (410) is configured to adjust a spacing between the central head support (410) and the arc member (140). As mentioned above, the arc member (140) comprises the connector (144). The connector (144) adjustably connects with the body (412) of the central head support (410). As illustrated, within the body (412) is a slot (424). The slot (424) receives a portion of the connector (144). As shown, the connector (144) comprises an upper beam portion (146) that is configured to be received within the slot (424). The profile of the beam portion (146) has a complementary shape to the slot (424). In the present example the beam portion (146) and slot (424) together form a dovetail interface. In this manner the connector (144) is translatable along the slot (424), which adjusts the spacing between the arc member (140) and the central head support (410). To control the adjustability of the connector (144) within the slot (424), the central head support (410) comprises the actuator (148) and the lock feature (149) as described above with respect to the HFD (100). With the HFD (400), the actuator (148) and lock feature (149) are configured and operable in the same manner as described above with respect to the HFD (100). In this configuration, the connector (144) is adjustable along or parallel to the plane defined by the central head support (410) to change a position of the arc member (140) relative to the central head support (410).

Referring to FIGS. 16-19, the HFD (400) comprises the pads (430) as mentioned above. The pads (430) comprise a housing (431), a first chamber (432), and a second chamber (433). A bore or cut-out (434) extends through the housing (431), the first chamber (432), and the second chamber (433). The bore (434) is located such that it is configured to receive a patient's ear during stabilization so as to protect the patient's ear from excessive compression and pressure, and instead direct such pressure and compressive force on the patient's skull. Located on the housing (431) is also an annular flange (435) that defines a slot (436) configured to connect with the remainder of the stabilizing assembly (186). In the present example, the stabilizing assembly includes a collar (437) having a flange (438) that fits within the slot (436). With this configuration, the pad (430) can be adjusted about an axis defined by and extending through the bore (184) as illustrated above in FIG. 5.

The first chamber (432) of the pad (430) defines an internal space (439) that is configured to be filled with a fluid, which may be a liquid or gas or combination. There is also a port (440) that can be opened and closed that connects with the first chamber (432) and provides access to the internal space (439) of the first chamber (432). In this manner, the fluid can be delivered to or vented or extracted from the internal space (439) of the first chamber (432) by way of the port (440).

Figure 18:
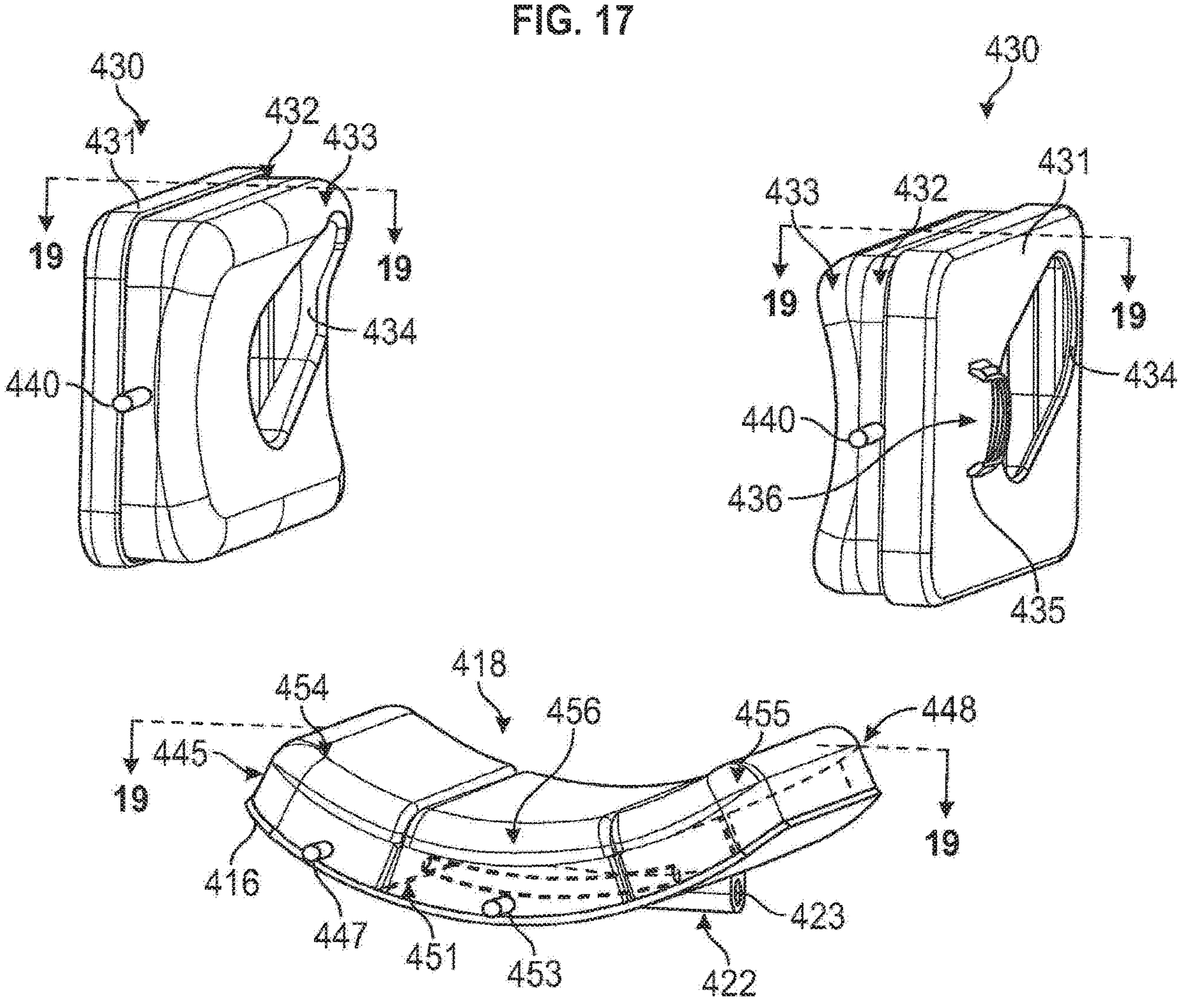
FIG. 18 depicts a rear perspective view of the cushion and pads used with the HFD of FIG. 16.
Figure 20:
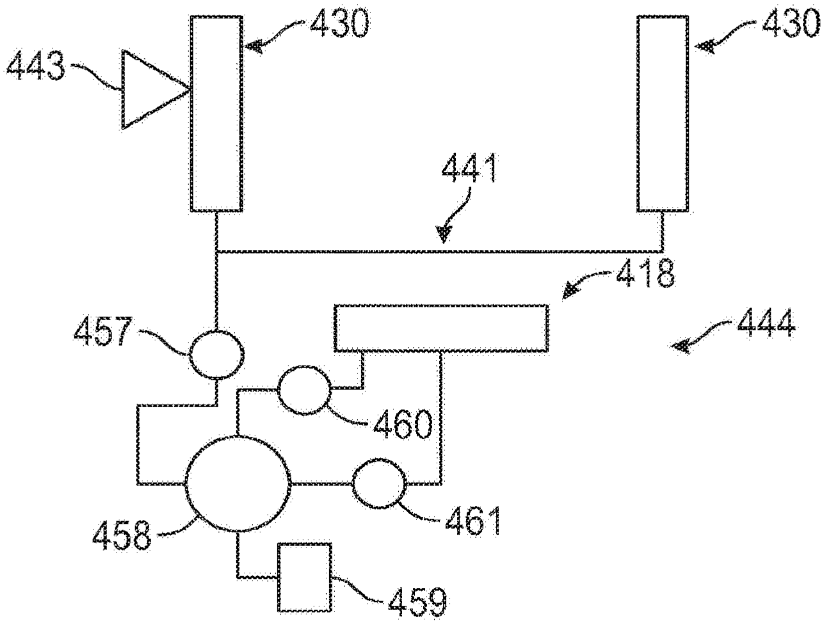
FIG. 20 depicts an exemplary schematic view of the HFD of FIG. 16 with a fluid control system.

Referring to FIGS. 18 and 20 when the pads (430) are used with each stabilizing assembly (186), in some versions the ports (440) are connected by a tube, hose, or conduit (441). The tube (441) may be connected to a valve (457) and further connected to a fluid reservoir (459) as described further below. In this configuration, by connecting the first chambers (432) of multiple pads (430), the pressure within the first chambers (432) is the same, and the pressure changes in the same fashion too as the first chambers (432) may be filled with more fluid to increase the pressure, or fluid vented from the first chambers (432) to decrease the pressure within.

As shown in the illustrated version, the first chamber (432) is located between the housing (431) and the second chamber (433). Of course in other versions, in view of the teachings herein, it will be apparent to those of ordinary skill in the art that the locations of the first chamber (432) and the second chamber (433) may be switched. The second chamber (433) of the pad (430) is configured to be filled with a shape-conforming material as described above with respect to cushion (318). In the present example, the second chamber (433) is positioned to be adjacent to and in contact with the head of the patient. In one version, the shape-conforming material within the second chamber (433) is one of either a gel, a foam, a granule material or a combination of such materials. In view of the teachings herein, other shape-conforming materials usable with the second chambers (433) of pads (430) will be apparent to those of ordinary skill in the art.

With the configuration of the pads (430) described above, the pads (430) are configured to provide a uniform distribution of contact pressure with the head of the patient when the head is supported by the stabilization assemblies (186) having the pads (430). Moreover, the contact pressure can be increased by filling the first chamber (432) with fluid via the port (440) or via the tube (441) connected with the ports (440) as shown in FIG. 20, which depicts a fluid control system (444). Conversely, the contact pressure can be decreased by venting the fluid from the first chamber (432) as mentioned above. By reducing the contact pressure, blood flow can be restored to the area of the patient's head in contact with the pads (430). In some instances, but not required in all versions, substantial venting of the fluid from the first chamber (432) may cause the pads (430) to deflate or reduce in size such that the pads (430) no longer applies contact pressure to the head of the patient sufficient for stabilization. In at least some instances, contact pressure sufficient to provide stabilization can be referred to as stabilizing pressure. By reducing the contact pressure to the extent that the stabilizing pressure between the pads (430) and the patient is lacking, blood flow can be restored to this area of the patient's head that was previously in contact with the pads (430) and under stabilizing pressure. By reducing contact pressure and providing for restoration of blood flow, tissue trauma or injury can be avoided or the risk reduced. Additionally, support of the patient's head can be maintained by the cushion (418) of the central head support (410) when reducing contact pressure between the pads (430) and the patient's head so as to not sacrifice support of the patient when restoring blood flow to an area of tissue. In some instances, once sufficient time has elapsed to restore blood flow to the tissue area in contact with the pads (430), the contact pressure can be increased again by filling the first chambers (432) with the fluid to provide or restore an enhanced or a greater degree of stabilization.

In some versions of the HFD (400), both of the laterally positioned pads (430) are connected via the tube (441) and the pads (430) are kept at the same pressure at all times within each of the pads (430). In some other versions, it is not required to connect both the laterally positioned pads (430) with the tube (441), and thus each of the pads (430) can be controlled independent from the other in terms of its pressure. Still yet, various valve placements may be incorporated with the tube (441) such that the pads (430), even if connected via the tube (441), may be configured to be controlled independently. In view of the teachings herein, other ways to configure the pads (430) and control the pressure within will be apparent to those of ordinary skill in the art. By way of example only, and not limitation, the pressure demands within the pads (430) may differ with patient positions where the skull clamp (170) is rotated about the patient's head by sliding the skull clamp (170) along the arc member (140) as described above.

Figure 17:
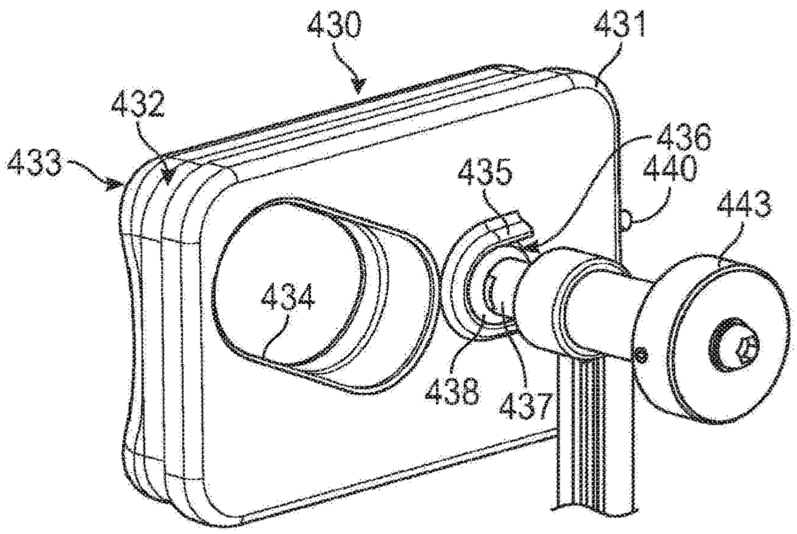
FIG. 17 depicts a partial perspective view of a stabilization assembly of the HFD of FIG. 16.

Referring to FIGS. 16 and 17, in some versions of the HFD (400), the pressure the pads (430) apply to the patient's head is adjustable using a torque screw (443). The torque screw (443) is a component of one of the stabilizing assemblies (186). Tightening the torque screw (443) increases the pressure applied by the pads (430) to the patient's head. In the illustrated version, the single torque screw (443) is on one side of the HFD (400), and the two pads (430) are connected by the tube (441) such actuation of the torque screw (443) changes the pressure in both the pads (430). In some other versions, multiple torque screws (443) could be used, one associated with each of the pads (430) such that the pads (430) may not be connected by the tube (441). In some versions using the HFD (400), the initial stabilization may be accomplished using the torque screw (443). After setting the torque screw (443) initially, subsequent pressure adjustments could be made by adjusting the amount of fluid within the first chambers (432) of the pads (430), e.g. by directing more fluid to the first chambers (432) to increase the pressure, or by venting fluid from the first chambers (432) to decrease the pressure. In other words, in some versions, whether or not the torque screw (443) is included, the contact pressure provided by each of the pads (430) can be controlled or adjusted separate and independent from the torque screw (443). In some versions, the torque screw (443) can be omitted altogether, and replaced with a conventional skull pin assembly. In view of the teachings herein, other ways to use either the torque screw (443), a fluid control system (444) as shown in FIG. 20, or both in combination will be apparent to those of ordinary skill in the art.

Figure 19:
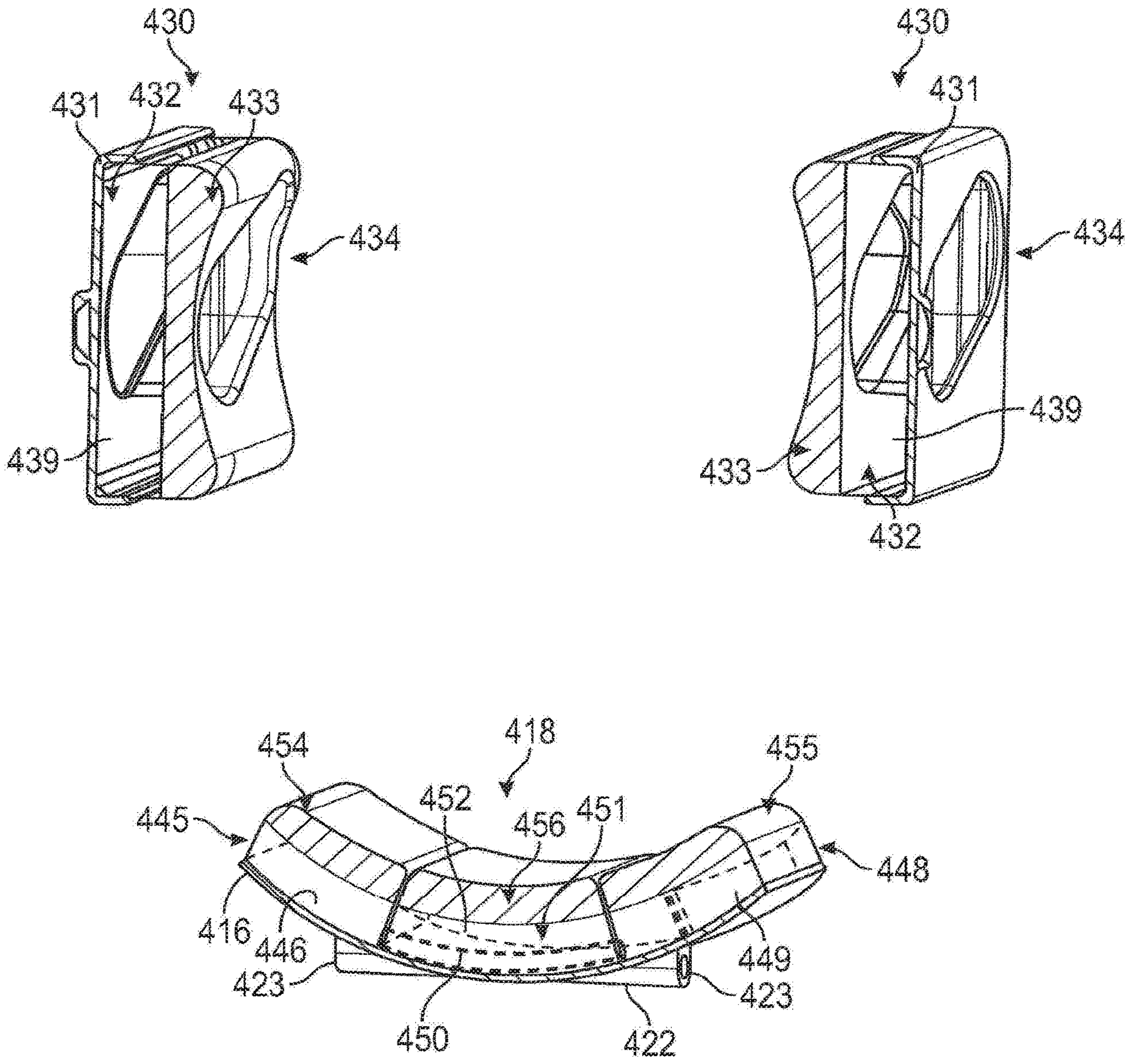
FIG. 19 depicts cross section view of the cushion and pads of FIG. 18.

Referring to FIGS. 18 and 19, the HFD (400) comprises the cushion (418) that connects with the base (416) of the central head support (410) as mentioned above. The cushion (418) of the HFD (400) comprises a multi-chamber structure with a first chamber (445) having an internal space (446) that is configured to be filled with a fluid. The fluid may be a gas or a liquid. The first chamber (445) includes a port (447) that is configured to provide access to the internal space (446). The fluid may be directed to the internal space (446) within the first chamber (445) or extracted from or vented from the internal space (446) of the first chamber (445). When venting fluid from the first chamber (445), all or a portion of the fluid may be released or vented from the internal space (446). The cushion further comprises a second chamber (448) having an internal space (449) that is configured to be filled with the fluid, or fluid may be extracted from or vented from the internal space (449) of the second chamber (448). When venting fluid from the second chamber (448), all or a portion of the fluid may be released or vented from the internal space (449). In the present example, the internal space (446) of the first chamber (445) and the internal space (449) of the second chamber (448) are in fluid communication by way of a connection tube (450) that extends between the internal spaces (446, 449) of the first and second chambers (445, 448).

The cushion (418) further comprises a third chamber (451) positioned between the first and second chambers (445, 448). In this configuration, the first and second chambers (445, 448) collectively define a pair of outer chambers while the third chamber (451) defines a middle chamber. The third chamber (451) also comprises an internal space (452), and the connection tube (450) extends through the internal space (452) of the third chamber (451). The internal space (452) of the third chamber is configured to be filled with the fluid similar to the first and second chambers (445, 448). The fluid may be added to or removed from the internal space (452), which can change the pressure within this area of the cushion (418). The third chamber (451) comprises a port (453) similar to the first chamber (445). The port (453) provides access to the internal space (452) and is used to direct fluid to the internal space (452) or vent fluid from the internal space (452).

The cushion (418) further comprises a fourth chamber (454), a fifth chamber (455), and a sixth chamber (456), each configured be filled with a shape-conforming material. The first chamber (445) is positioned subjacent to the fourth chamber (454), and the fourth chamber (454) is configured to contact the head of the patient. The second chamber (448) is positioned subjacent to the fifth chamber (455), and the fifth chamber (455) is configured to contact the head of the patient. The third chamber (451) is positioned subjacent to the sixth chamber (456), and the sixth chamber (456) is configured to contact the head of the patient. In view of the teachings herein, it will be apparent to those of ordinary skill in the art that the relative positions of the first and fourth chambers (445, 454), the second and fifth chambers (448, 455), and the third and sixth chambers (451, 456) may be switched in other versions. In one version, the shape-conforming material within the fourth, fifth, and sixth chambers (454, 455, 456) is one of either a gel, a foam, a granule material or a combination. In view of the teachings herein, other shape-conforming materials usable with the cushion (418) will be apparent to those of ordinary skill in the art.

With the configuration of the cushion (418) described above, the cushion (418) is configured to provide a various pressure profiles depending on the manner of adjustments with the fluid and each of the respective internal spaces (446, 449, 452). For instance, in some versions, a uniform distribution of contact pressure can be achieved where the third chamber (451) is configured to hold the same amount of fluid per unit of volume within the internal space (452) as in the internal spaces (446, 449) of the first and second chambers (445, 448). Still in other versions, the outer chambers may have matching pressures while the middle chamber has a pressure that may be higher or lower than the pressure within the outer chambers. Furthermore, in this configuration with differing pressures between the outer chambers and the middle chamber, the fluid may be vented and/or added in a controlled fashion to provide a way to promote blood flow to an area of the patient's tissue in contact with a portion of the cushion (418) while maintaining secure stabilization of the patient's head.

By way of example only, and not limitation, in one version, a patient is initially stabilized using the HFD (400) with the pads (430) applying the same contact pressure to portions of the patient's head. In the initial stabilization, the cushion (418) is configured such that the outer chambers and middle chamber also apply the same contact pressure to the back portion of the patient's head. In this example the HFD (400) is used with the patient in a supine position, but this is not necessary in all examples such that the HFD (400) may be used with the patient in other positions. After some time has passed, the pressure within the pads (430) and/or the cushion (418) can be manipulated so that blood flow can be restored or increased to the areas where the tissue of the patient's head contacts portions of the HFD (400). Moreover, this manipulation of pressure comprises a short term relief or reduction of pressure to promote increased blood flow to the tissue, followed by an increase in pressure after a period of time has passed to provide for enhanced stabilization. Furthermore, this manipulation of pressure can be performed in an alternating fashion among the pads (430) and/or chambers of the cushion (418). By using this alternating fashion, the tissue areas in contact with the HFD (400) are treated with restored or increased blood flow while maintaining an acceptable degree of stabilization.

An example of the alternating pressure relief and restoration sequence can include as a first step, after an initial stabilization is configured, reducing the pressure in the pads (430) to give an amount of time to restore blood flow to the portions of the patient's head contacted by pads (430). Note that in some such examples the pressure in the pads (430) may not be reduced at all, and the pressure relief sequence may be limited to the multi-chamber cushion (418). Note also that in other examples, the first step may be to perform a pressure relief step or process on the multi-chamber cushion (418) and thereafter perform a pressure relief step on one or both of the pads (430). In the present example, however, after the pressure in the pads (430) has been reduced and some time has passed where blood flow has been increased to the tissue areas of the patient in contact with the pads (430), the pressure in the pads (430) is then restored to its initial level.

Thereafter, the middle chamber defined by the third chamber (451) is vented to reduce its pressure. This action reduces the force or pressure applied to the patient's head at the middle chamber and thus allows for increased blood flow to this back area of the patient's head in contact with the middle chamber. In this case, the outer chambers, defined collectively by the first and second chambers (445, 448), remain at their original or initial pressure or experience a higher pressure based on an increase in force in these areas from the patient's head with the middle chamber vented. Thus the outer chambers and the pads (430) provide stabilization to the patient's head while the tissue area in contact with the middle chamber is receiving a period of increased or restored blood flow to prevent or reduce the risk of tissue trauma in this area.

For the sake of further clarity, the middle chamber of the cushion (418) comprises both the third chamber (451) that is configured to contain the fluid, as well as the sixth chamber (456) that is configured with the shape-conforming material. Similarly, with the pair of outer chambers, one of the outer chambers comprises the first chamber (445) that is configured to contain the fluid, as well as the fourth chamber (454) that is configured with the shape-conforming material. And the other of the outer chambers comprises the second chamber (448) that is configured to contain the fluid, as well as the fifth chamber (455) that is configured with the shape-conforming material. As will be understood in view of the teachings herein, the pressure relief discussed above within the outer chambers and the middle chamber occurs by changing the fluid volume within the respective internal spaces (446, 449, 452) of the first, second, and third chambers (445, 448, 451), while the increase in blood flow based on the pressure relief occurs at the tissue areas in contact with the respective fourth, fifth, and sixth chambers (454, 455, 456) having the shape-conforming material. In other configurations for the HFD (400) and other HFDs, the fluid-filled chambers may be the chambers in contact with the patient's head while the shape-conforming containing chambers may be located beneath or subjacent to the respective fluid-filled chambers. In view of the teachings herein, other configurations for the chambers of the HFD (400) and other HFDs will be apparent to those of ordinary skill in the art.

Returning again to the example above of a pressure relief sequence, after the pressure in middle chamber of the cushion (418) has been reduced and some time has passed where blood flow has been increased to the tissue area of the patient in contact with the middle chamber, and specifically the sixth chamber (456), the pressure in the middle chamber of the cushion (418) is then restored to its initial level. Thereafter, the pair of outer chambers are vented to reduce their pressure by venting or extracting fluid from the respective first and second chambers (445, 448). This action reduces the force or pressure applied to the patient's head at the outer chambers, and thus allows for increased blood flow to these areas of the patient's head in contact with the outer chambers, and more specifically at the areas of contact with the respective fourth and fifth chambers (454, 455). In this case, the middle chamber remains at its original or initial pressure as well as the pads (430). Thus the middle chamber and the pads (430) provide stabilization to the patient's head while the tissue area in contact with the outer chambers is receiving a period of increased or restored blood flow to prevent or reduce the risk of tissue trauma in this area.

After the pressure in outer chambers of the cushion (418) has been reduced and some time has passed where blood flow has been increased to the tissue area of the patient in contact with the outer chambers, and specifically the fourth and fifth chambers (454, 455), the pressure in the outer chambers of the cushion (418) is then restored to its initial level. The above described pressure relief process can be conducted multiple times as needed or desired to help reduce the risk of tissue injury or trauma. Moreover, these pressure relief actions can be completed in any order as the circumstances require or dictate such that the example order described above should not be considered a required order or the only order or sequence.

With the HFD (400), as described above, the fluid connection between the first chambers (432) of the pads (430) via the tube (441) allows for the pressure in each of the pads (430) to be the same and to be simultaneously adjusted such that while the pressure in the pads (430) changes, it does so in the same manner and to the same degree. With the pads (430) generally located on opposite sides of the patient's head, the fluid connection between the first chambers (432) of the pads (430) allows for pressure changes within the pads (430) to promote blood flow to the tissue areas contacted by the pads (430) without altering the differential in the force that is applied to the opposing sides of the patient's head by the respective pads (430). This configuration allows for the pressure changes within the pads (430) without causing the patient's head to move or change position.

For instance, in one example, the initial force applied to each side of the patient's head by each of the pads (430) may be about 20 newtons, and thus the differential in force would be zero because the force applied by each of the pads (430) is the same. When an example pressure relief process has been performed, the force applied to each side of the patient's head by each of the pads (430) may now be about 50 newtons, and thus the differential in force maintained at zero because the force applied by each of the pads (430) remains the same. While in the illustrated example of the HFD (400) the pads (430) are fluidly connected by the tube (441), this is not required in all versions. For instance, in some other versions the pads (430) may be independently adjustable or controllable regarding their pressure based on fluid volumes within the first chambers (432).

Similar to the pads (430), with the HFD (400) as described above, the fluid connection between the first chamber (445) and the second chamber (448) of the cushion (418) via the connection tube (450) allows for the pressure in each of the outer chambers of the cushion (418) to be the same and to be simultaneously adjusted such that while the pressure in the outer chambers of the cushion (418) changes, it does so in the same manner and to the same degree. As shown and described, the outer chambers of the cushion (418) are generally located on opposite sides of the sagittal plane of the patient's head when in the supine position such that the outer chambers of the cushion (418) are substantially symmetrically located about the sagittal plane dividing the patient's head into left and right portions. The fluid connection between the outer chambers of the cushion (418) allows for pressure changes within the outer chambers of the cushion (418) to promote blood flow to the tissue areas contacted by the outer chambers of the cushion (418) without altering the differential in the force that is applied to the patient's head by the respective outer chambers of the cushion (418). This configuration allows for the pressure changes within the outer chambers of the cushion (418) without causing the patient's head to move or change position, i.e. rotating about the patient's longitudinal axis because of an uneven force applied by one of the outer chambers of the cushion (418) compared to the other outer chamber of the cushion (418).

V. Exemplary Fluid Control Systems and Methods

Referring now to FIG. 20, the fluid control system (444) is shown with the HFD (400) schematically. As described above in detail, the HFD (400) includes the pads (430) that provide the lateral stabilization to the patient's head, and the cushion (418) that provides subjacent support and stabilization. As shown in FIG. 20, the torque screw (443) connects with one of the pads (430) to permit increasing or decreasing the pressure the pad (430) applies to the patient's head. The connection tube (441) connects the pads (430) together such that they are in fluid communication. As described above, the connection tube (441) connects the first chambers (432) of the respective pads (430). In this configuration, the pressure in each of the pads (430) is the same and each of the pads (430) imparts the same force on the patient's head.

Also connected with the connection tube (441) is a valve (457). The valve (457) is configured to selectively vent fluid from the pads (430) to reduce the pressure within the pads (430) or to permit additional fluid to flow to the pads (430) to increase the pressure within the pads (430). The valve (457) connects with a pump (458), which is configured to supply additional fluid to the pads (430) when desired. In some versions, the pump (458) can also be configured to direct vented or extracted fluid away from the pads (430). In fluid communication with the pump (458) is a fluid reservoir (459). The fluid reservoir (459) is configured to provide additional fluid to be delivered via the pump (458) to the pads (430). In some instances, venting fluid from the pads (430) involves opening the valve (457) and operating the pump (458) to move fluid from the pads (430) to the fluid reservoir (459). The pump (458) can also be used without the fluid reservoir (459) such that the fluid reservoir (459) may be omitted in some versions. In such versions, the pump (458) may be configured to deliver air from the surrounding environment to the pads (430). Similarly, venting fluid from the pads (430) in such versions may involve venting air from the pads (430) back to the surrounding environment instead of venting to the fluid reservoir (459). In some examples, the fluid reservoir (459) itself can be considered the surrounding environment.

Figure 25:
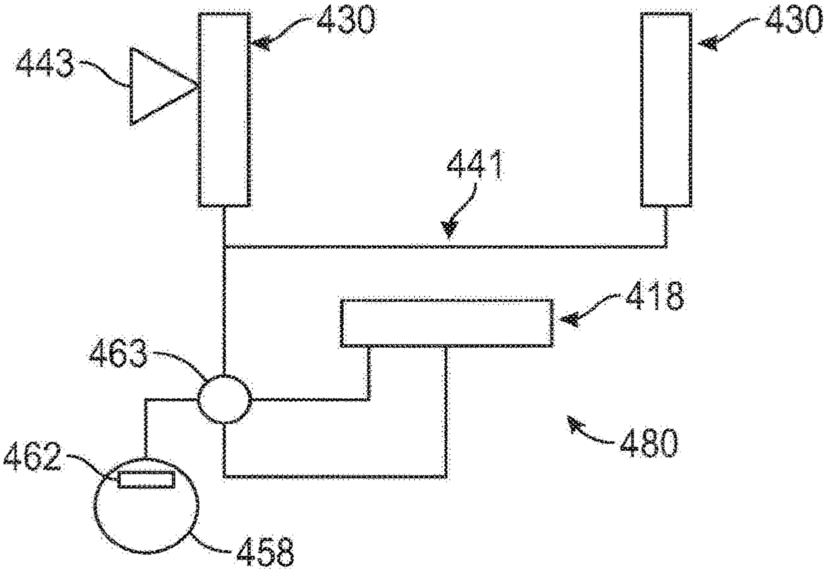
FIG. 25 depicts an exemplary schematic view of the HFD of FIG. 16 with a fluid control system.

In one version having a simplified configuration for the fluid control system (444), the fluid reservoir (459) is omitted, and the pump (458) comprises a hand pump or foot pump having a pressure gauge and configured to be manually operated. In this example, the pump (458) is selectively connectable with the various valves (457, 460, 461) to adjust fluid volumes and pressure within the pads (430) and cushion (418). In some versions, such as illustrated in FIG. 25, a fluid control system (480) can have a single valve (463) that is switchable can be used instead of the multiple valves (457, 460, 461). In such an instance, the valve (463) connects with the pump (458) as well as the respective ports (447, 453) of the cushion (418). As also shown, the valve (463) can also be connected with the pads (430) via the connection tube (441), although this additional fluid connection is not required in all versions and may be controlled by a separate fluid control system. When controlling fluid within the fluid control system (480), the valve (463) is configured such that fluid can be directed to any of the fluid holding chambers of the cushion (418) and/or the pads (430). Moreover, the valve (463) can be configured to direct fluid to more than one of the chambers of the cushion (418) and/or pads (430) at the same time. The pump (458) is configured with a pressure gauge (462) and the pressure gauge (462) is configured to indicate a pressure within the chambers to which the valve (463) is actively in fluid communication with. In view of the teachings herein, other configurations for the various fluid control systems will be apparent to those of ordinary skill in the art. For instance, it will be appreciated that to direct the fluid, a single pump or multiple pumps may be used, a single valve or multiple valves may be used, and a variety of ports and connection tubes may be used.

In the present example, the pump (458) also connects two other valves (460, 461) that connect with the respective ports (447, 453) of the cushion (418). The valves (460, 461) are configured similar to the valve (457) and thus the pump (458) can also be operated to provide additional fluid from the fluid reservoir (459) to either or both of the outer chambers and middle chamber of the cushion (418). As described above with respect to the HFD (400), the fluid is provided to the first and third chambers (445, 451) of the cushion (418). Furthermore, in this configuration, fluid can be vented or extracted from the cushion (418) by either venting the fluid to the atmosphere via the valves (460, 461) in one example, or by opening the valves (460, 461) and operating the pump (458) to transfer fluid to the fluid reservoir (459). In view of the teachings herein, other ways to configure and operate the fluid control system (444) to manipulate the pressures within the pads (430) and cushion (418) will be apparent to those of ordinary skill in the art.

Figure 21:
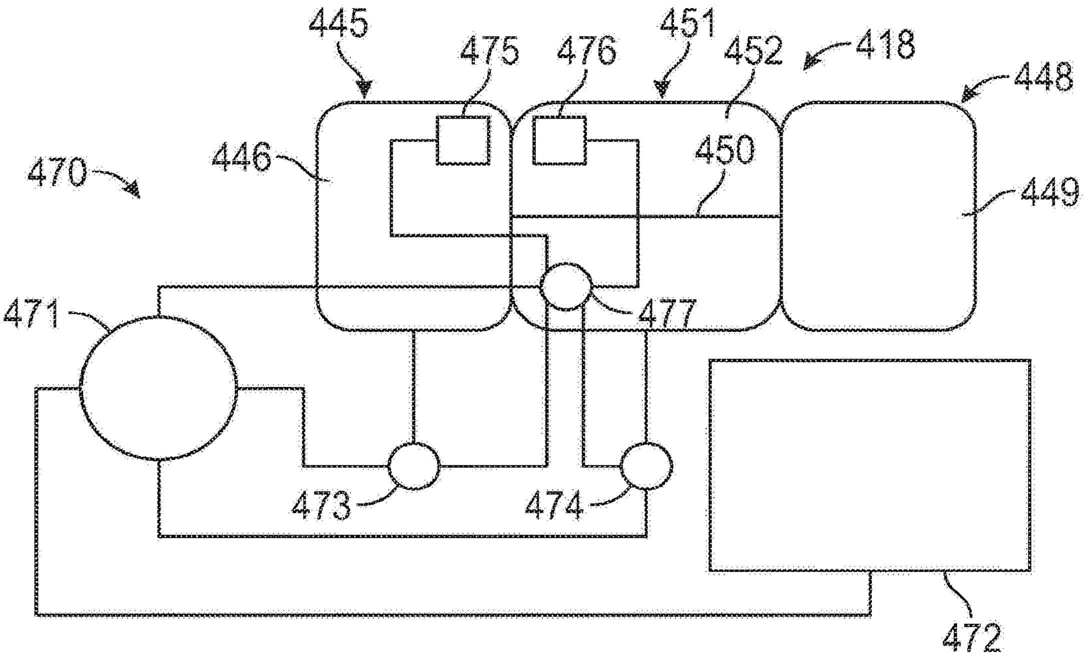
FIG. 21 depicts an exemplary schematic view of a fluid control system usable with the HFD of FIG. 16 and other HFDs described herein.

FIG. 21 shows another exemplary fluid control system (470) that is usable with the multi-chamber cushion (418) of the HFD (400). The fluid control system (470) is configured to provide fluid control where the outer chambers and middle chamber can be vented and refilled in an alternating manner as described above. Again, as discussed above this alternating venting or pressure relief provides for the ability to increase blood flow to certain areas of the patient's head, while also maintaining adequate stabilization of the patient's head.

As shown in the illustrated version of FIG. 21, the fluid control system (470) comprises a pump (471) connected to a fluid reservoir (472) containing fluid. With the fluid control system (470) the pump (471) further connects with two valves (473, 474). One of the valves (473) connects with the port (447) of the first chamber (445) of the cushion (418), and the other valve (474) connects with the port (453) of the third chamber (448) of the cushion (418). The connections between the pump (471), the fluid reservoir (472), the valves (473, 474), and the ports (447, 453) are such that these components are in fluid communication so that fluid can be transported between these components. Accordingly, the fluid control system (470) is configured to either direct fluid to the cushion (418) or extract or vent fluid from the cushion (418). As described above, the first chamber (445) of the cushion (418) connects with the second chamber (448) by way of tube (450) such that fluid changes impact both chambers (445, 448) in the same manner and to the same degree such that the pair of outer chambers have the same pressure.

Within the internal space (446) of the first chamber (445), the fluid control system (470) includes a pressure sensor (475). In some other versions, the pressure sensor (475) can be instead located within the internal space (449) of the second chamber (448). The fluid control system (470) further includes a pressure sensor (476) located within the internal space (452) of the third chamber (451). In the present example, the pressure sensors (475, 476) connect with a control unit (477). In the illustrated example, the control unit (477) is also located within the internal space (452) of the third chamber (451). In some other versions, the control unit (477) can be located in other positions within or outside of the cushion (418). Also connected with the control unit (477) are the valves (473, 474) and the pump (471). The connections between the control unit (477), the pump (471), the valves (473, 474), and the sensors (475, 476) are such that these components are in electrical communication so that electrical signals can be transmitted and/or received by between these components. The components described here that transmit and/or receive signals are powered by batteries contained within these components. Of course in other versions, separate power sources may be used instead of or in addition to the batteries within the components. In view of the teachings herein, other ways to provide power to the components described here will be apparent to those of ordinary skill in the art.

With the configuration described above for FIG. 21, in operation the fluid control system (470) can be configured such that the control unit (477) is operable to change the fluid volumes within the first, second, and third chambers (445, 448, 451) using signals from the pressure sensors (475, 476). For example, after some time has passed where a patient's head has been stabilized with the HFD (400), it may be desired to selectively relieve pressure on the patient's head to restore blood flow to certain tissue areas contacted by the HFD (400) to reduce the risk of tissue trauma or injury as described above. With the fluid control system (470), the control unit (477) can be programmed to execute a set of instructions whereby the pair of outer chambers of the cushion (418) and the middle chamber are manipulated in an alternating fashion to relieve pressure by venting or extracting the fluid to allow for a period of increased blood flow to the tissue before increasing the pressure by delivering fluid back to the respective chamber from which the fluid was previously vented or extracted.

By way of example only, and not limitation, one alternating sequence of pressure relief using the fluid control system (470) may be conducted by initiating at the control unit (477) a first pressure relief action or process where the fluid is vented or extracted from the first and second chambers (445, 448) until the pressure sensor (475) reaches a predetermined value. The predetermined value may be a percentage reduction in the pressure sensor (475) reading, or it may be a selected pressure value that may be determined to increase blood flow to the tissue area without compromising the stability of the patient. Once the pressure sensor (475) reaches the predetermined value, a predetermined wait time ensues where time is provided for restoration or increase of blood flow to the areas of tissue in contact with the outer chambers. After the predetermined wait time has elapsed, the control unit (477) sends a signal to the pump (471) and the valve (473) to direct fluid to the first and second chambers (445, 448) to add fluid until the sensor (475) reaches a predetermined value for pressure. This predetermined value may be the same as the pressure in the outer chambers of the cushion (418) before the pressure relief cycle began, or it may be a different pressure value.

With the outer chambers refilled and having sufficient pressure to provide sufficient stabilizing force to the patient's head, next the control unit (477) initiates a second pressure relief action or process where the fluid is vented or extracted from the third chamber (451) until the pressure sensor (476) reaches a predetermined value. The predetermined value may be a percentage reduction in the pressure sensor (476) reading, or it may be a selected pressure value that may be determined to increase blood flow to the tissue area without compromising the stability of the patient. Once the pressure sensor (476) reaches the predetermined value, a predetermined wait time ensues where time is provided for restoration or increase of blood flow to the areas of tissue in contact with the middle chamber. After the predetermined wait time has elapsed, the control unit (477) sends a signal to the pump (471) and the valve (474) to direct fluid to the third chambers (451) to add fluid until the sensor (476) reaches a predetermined value for pressure. This predetermined value may be the same as the pressure in the middle chamber of the cushion (418) before the pressure relief cycle began, or it may be a different pressure value. From this point, once alternating cycle would have been completed and subsequent alternating cycles could continue immediately thereafter or after some time has passed.

In view of the teachings herein, other ways to configure and operate the fluid control system (470) will be apparent to those of ordinary skill in the art. For instance, in some versions, the sensors (475, 476), the valves (473, 474), the pump (471), and/or the control unit (477) may be connected with an output display where the pressure and fluid data within the cushion (418) may be visually displayed. In other instances, this data could be wirelessly transmitted to a device with a display, e.g. the fluid control system (470) could be operable via an application installed on a computer or tablet. Still yet, in other versions, the control unit (477) may be located outside the cushion (418) and further connected with the pads (430) using similar sensors and valves such that the control unit (477) is able to control fluid deliver and extraction from both the chambers of the cushion (418) as well as one or more of the pads (430). Still further, in some versions the pump (471) includes an integrated measurement of the pressure, such that one or both of the sensors (475, 476) may be effectively part of or within the pump (471).

VI. Exemplary Head Fixation Device with Arc and Curved Member

Figure 22:
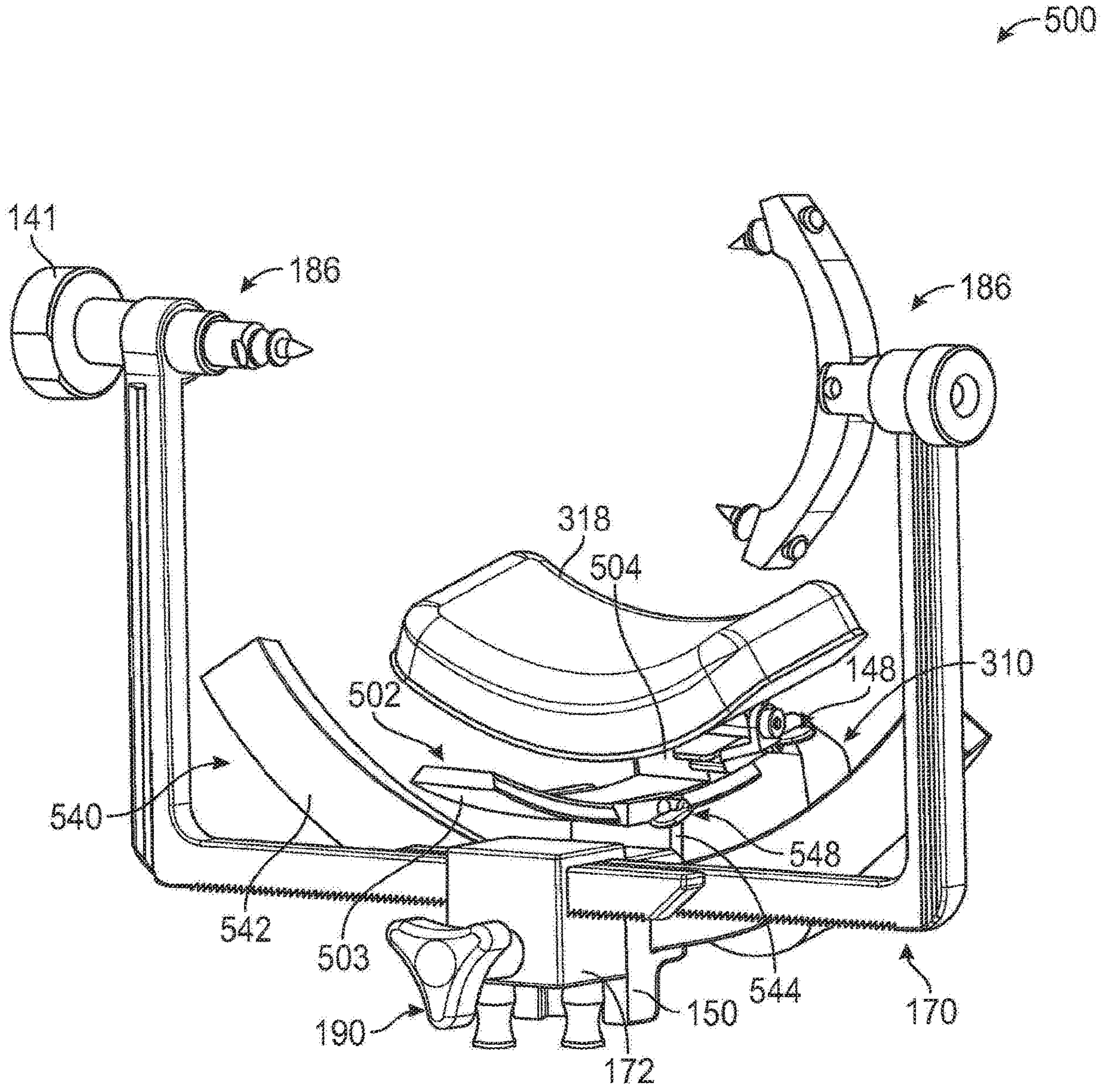
FIG. 22 depicts a perspective view of another exemplary HFD that includes a rotational adjustment of an arc member.

As described above with respect to some exemplary HFDs, in certain examples the connected arc member and skull clamp are adjustable to some degree toward or away from the cushion of the HFD that supports the patient's head. FIG. 22 depicts another exemplary HFD (500) that includes this type of adjustability but incorporating a different arc member (540) and a curved member (502) as described further below.

Figure 23:
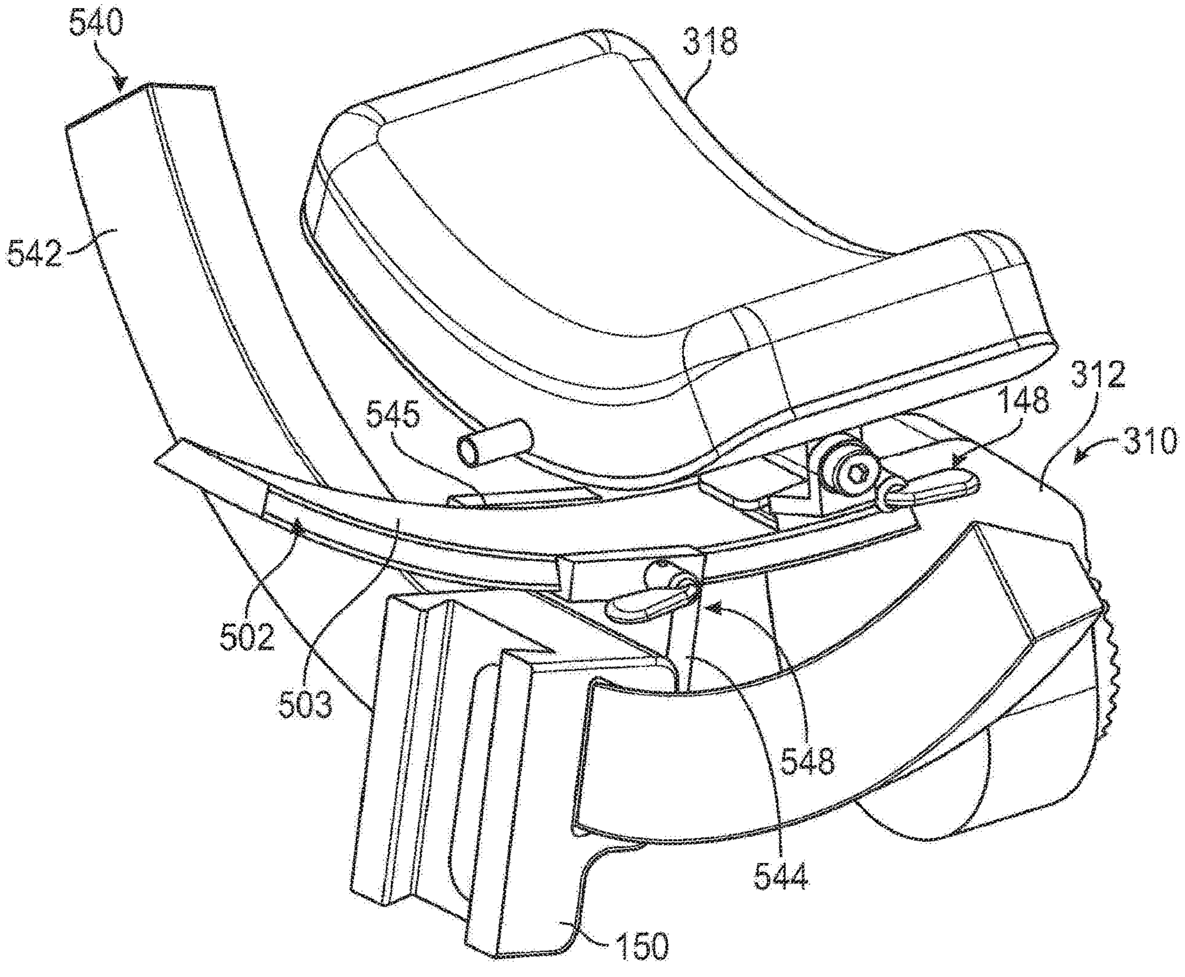
FIG. 23 depicts a partial perspective view of the HFD of FIG. 22, shown without the skull clamp, locking member, and actuator.
Figure 24:
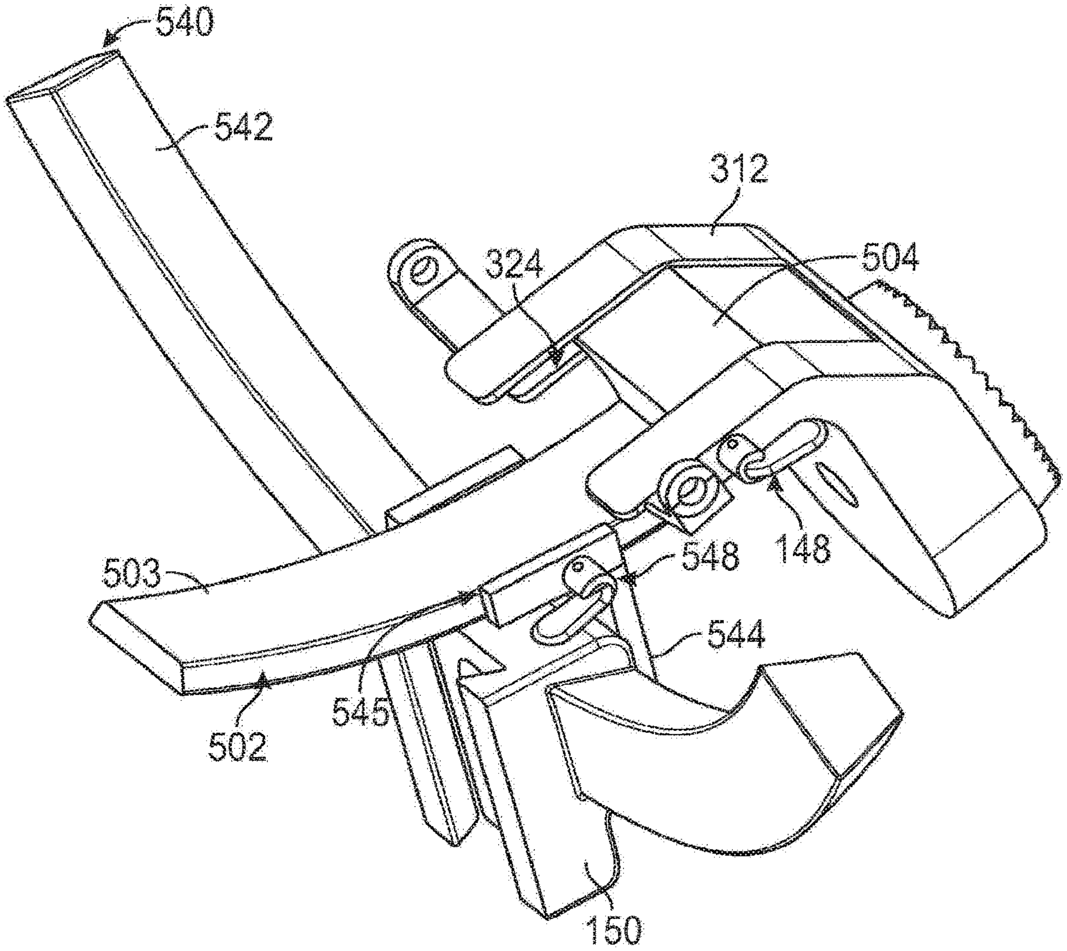
FIG. 24 depicts another partial perspective view of the HFD as shown in FIG. 23, but with the cushion and base removed.

Referring to FIGS. 22-24, the HFD (500) is similar in respects to the above-described HFD (300), but the HFD (500) incorporates arc member (540) in place of arc member (140) described above, and the HFD (500) includes the curved member (502). The HFD (500) comprises the skull clamp (170) and the actuator (190) as described above. The HFD (500) also comprises the central head support (310) and the pivotable cushion (318) as described above with respect to the HFD (300). It should be noted that the cushion (318) could be replaced with other cushions, such as with cushions (418, 118). In view of the teachings herein, ways to incorporate the cushions (118, 418) instead of the cushion (318) will be apparent to those of ordinary skill in the art. The HFD (500) further includes stabilization assemblies (186) similar to the HFD (300) where pins are used to stabilize the patient's head. It should be noted that the HFD (500) may be modified such that the pads (430) described above with respect to the HFD (400) can replace the illustrated pins in other versions. In view of the teachings herein, ways to incorporate the pads (430) for the stabilizing assemblies (186) instead of the pins will be apparent to those of ordinary skill in the art. As mentioned, except as described below, the features of the HFD (500) are the same as those described above with respect to the HFD (300). Therefore, for the sake of brevity, the features of the HFD (300) described above apply equally to the HFD (500) with the exception of the described differences above and below.

With the HFD (500), the central head support (310) and the arc member (540) are configured to adjust a spacing between the central head support (310) and the arc member (540). Because the arc member (540) connects with the skull clamp (170) in the same manner as does the arc member (140) as described above, the spacing adjustment between the central head support (310) and the arc member (540) also adjusts the spacing between the central head support (310) and the skull clamp (170). The arc member (540) comprises a connector (544). The connector (544) adjustably connects with the curved member (502) as shown in the illustrated version of FIGS. 22-24. The curved member (502) comprises an elongated portion (503) and a beam portion (504). As illustrated, within the connector (544) is a slot (545). The slot (545) receives the elongated portion (503) of the curved member (502). As also shown, the curved member (502) further connects with the body (312) of the central head support (310). As illustrated, within the body (312) is a slot (324). The slot (324) receives the beam portion (504) of the curved member (502). With this configuration, the elongated portion (503) of the curved member (502) defines an arc length and a radius of curvature. The radius of curvature represents the distance from a center point of a patient's head when positioned on the cushion (318) to a point at the middle of the cross section of the elongated portion (503). By way of example only, and not limitation, in some examples the curved member (502) can have an arc length between about 80 and about 180 millimeters, and define a radius of curvature between about 120 and about 200 millimeters. For instance, in one example the curved member (502) defines a radius of curvature of about 162 millimeters with an arc length of about 123 millimeters. Of course these specific dimensions are not required in all version and other suitable dimensions will be apparent to those of ordinary skill in the art in view of the teachings herein.

In the present example, the profile of the elongated portion (503) of the curved member (502) has a complementary shape to the slot (545). Additionally, the profile of the beam portion (504) has a complementary shape to the slot (324). In the present example the elongated portion (503) and the slot (545) together form a dovetail interface in cross section, and the beam portion (504) and slot (324) together form a dovetail interface in cross section. In this manner the arc member (540) is adjustable relative to the central head support (310) by moving the connector (544) with its slot (545) along the elongated portion (503) of the curved member (502). Also, the arc member (540) is adjustable relative to the central head support (310) by moving the beam portion (504) of the curved member (502) along the slot (324) of the central head support (310). Thus, this configuration provides for multiple, in this example two, ways in which to adjust the spacing between the arc member (540) and its connected skull clamp (170) and the central head support (310).

In the present example, moving the slot (545) of the connector (544) of the arc member (540) along the elongated portion (503) of the curved member (502) occurs along an arc or curved path. In this manner, arc member (540) is rotatable relative to the curved member (502), and the rotation occurs along the interface of the slot (545) of the connector (544) and the elongated portion (503) of the curved member (502). In this example, the slot (545) comprises a radius of curvature and the elongated portion (503) of the curved member (502) defines a matching radius of curvature.

The curved member (502), in the present example, is oriented perpendicular to a curved elongated member (542) of the arc member (540). In other words, a plane defined by the curved elongated member (542) of the arc member (540) is perpendicular to a plane defined by the longitudinal arc of the elongated portion (503) of the curved member (502). In this configuration, with a patient's head supported by the cushion (318) of the HFD (500), the arc member (540) is rotatable about the patient's head along the direction of the longitudinal axis of the patient. This adjustment complements and provides another adjustment for securely stabilizing the patient in addition to the adjustment described above regarding being able to adjust the skull clamp (170) along the curved elongated member (542) of the arc member (540). Thus with this configuration, with the skull clamp (170) connected with the arc member (540), the skull clamp (170) can be rotationally adjusted about the patient's head both about the longitudinal axis of the patient extending through the patient's head and also along the longitudinal axis of the patient extending through the patient's head. This range of adjustment helps to promote proper placement or locating of the stabilizing assemblies (186) on the patient's head.

As described above, the arc member (540) can also be translated relative to the central head support (310) of the HFD (500). This translation occurs along the interface of the beam portion (504) and the slot (324). In this manner, when the arc member (540) is adjusted relative to the central head support (310), the beam portion (504) of the curved member (502) translates in a linear fashion within the slot (324). This adjustment, in combination with the other adjustments described above, provides a further degree of freedom regarding placement or locating the stabilizing assemblies (186) the skull clamp (170) on the patient's head. In view of the teachings herein, other ways to configure the HFD (500) as well as the arc member (540) and curved member (502) for providing proper placement of the stabilizing assemblies (186) for secure patient stabilization will be apparent to those of ordinary skill in the art.

To control the rotational adjustability of the arc member (540) along the elongated portion (503) of the curved member (502) as described above, the connector (544) of the arc member (540) comprises an actuator (548) that controls a lock feature within the connector (544) that selectively secures the relative position of the connector (544) along the elongated portion (503) of the curved member (502). The actuator (548) and the lock feature are similar to the actuator (148) and the lock feature (149) as described above with respect to the HFD (100). Similarly, to control the translational adjustability of the beam portion (504) of the curved member (502) along the slot (324) of the central head support (310), the central head support (310) comprises the actuator (148) and the lock feature (149) as described above with respect to the HFD (100). With the HFD (500), the actuator (148) and lock feature (149) are configured and operable in the same manner as described above with respect to the HFD (100). In view of the teachings herein, other ways the HFD (500) may be modified to control the adjustability of the arc member (540) relative to the curved member (502), and to control the adjustability of the curved member (502) relative to the central head support (310) will be apparent to those of ordinary skill in the art.

VII. Exemplary Head Fixation Device with Cassette Features

FIGS. 26-30 illustrate an exemplary HFD (1000) configured for use in supporting and stabilizing a head of a patient during a medical procedure. The HFD (1000) comprises a central head support (1100) and a skull clamp (1001) connectable with the central head support (1100) by a positioning assembly (1200).

The central head support (1100) comprises a body (1102) and an attachment feature (1104) on the body (1102), where the attachment feature (1104) is in the form of a starburst configured to connect with an operating table or other structure directly or indirectly via one or more intermediate structures. For example, in some instances a base unit, such as those available from pro med instruments GmbH, attaches to an operating table and the attachment feature (1104) connects with the base unit. In some instances an adapter, such as a swivel adapter or other adapter available from pro med instruments GmbH, may connect with the base unit, and the attachment feature (1104) of the central head support (1100) connects with the adapter. In view of the teachings herein, various ways to connect the central head support (1100) with a stable structure such as an operating table, etc. will be apparent to those of ordinary skill in the art.

The central head support (1100) also comprises a base (1106) that connects with the body (1102) and that holds or retains a cushion (1108). The cushion (1108) may connect with the base (1106) by way of an adhesive, mechanical fasteners such as screws or hook and loop, or other ways that will be apparent to those of ordinary skill in the art. In some versions, the cushion (1108) is selectively connected with the base (1106) such that the cushion (1108) may be disposable or may be removed for cleaning and sterilization after use. The cushion (1108) is configured to contact the head of the patient when the HFD (1000) is used to support and stabilize the patient. In the present example, the base (1106) connects with the body (1102) by way of a disc (1110), which is connected with the base (1106) using fasteners such as screws or bolts, etc. The disc (1110) is received within a slot (1112) defined in the body (1102). In the present example, the disc (1110) is rotatable within the slot (1112) such that the attached base (1106) and cushion (1108) are rotatably adjustable. In the present example, the disc (1110) and slot (1112) features and construction is the same or similar to those features described above.

The cushion (1108) is configured to contain a shape-conforming material, which may be a fluid such as liquid, gas, or gel. In one version, the shape-conforming material is one of either a gel, a foam, or a granule material. In view of the teachings herein, other shape-conforming materials usable with the cushion (1108) will be apparent to those of ordinary skill in the art.

In use, the central head support (1100) is configured to provide subjacent support to the head of the patient. In this manner, the central head support (1100) defines a plane that extends subjacent to the head of the patient when the head of the patient is supported by the central head support. In the present example, the central head support (1100) is positioned such that the plane defined by the central head support (1100) is parallel to a floor, or orthogonal to a direction of gravitational force on the central head support (1100). Furthermore, the central head support (1100) defines a central axis (Al) that extends through the center of the cushion (1108) and parallel with the direction of gravitation force on the central head support (1100).

The positioning assembly (1200) of the HFD (1000) connects with the central head support (1100). In the present example the positioning assembly (1200) comprises a cassette carrier (1202), a connector (1204), an actuator (1206), and a locking insert (1208). In connecting with the central head support (1100), the connector (1204) includes a beam portion (1210) that is slidingly received by a slot (1114) of the central head support (1100), which is located beneath the slot (1112) that receives the disc (1110). In this manner, the central head support (1100) is configured to adjust the spacing between the central head support (1100) and the positioning assembly (1200). Since the positioning assembly (1200) is further connected with the skull clamp (1001) as will be described further below, the central head support (1100) can be considered to be configured to adjust the spacing between itself and the skull clamp (1001). The profile of the beam portion (1210) has a complementary shape to the slot (1114). In the present example the beam portion (1210) and slot (1114) together form a dovetail interface. In this manner the connector (1204) is translatable along the slot (1114), which adjusts the spacing between the positioning assembly (1200) and the central head support (1100).

To control the adjustability of the connector (1204) within the slot (1114), the central head support (1100) comprises an actuator (1116) that includes a lock feature (1118) that contacts the beam portion (1210) to either secure its position relative to the body (1102) within the slot (1114) via a compression engagement, or permit slidable adjustment of the connector (1204) relative to the body (1102) by the lock feature (1118) disengaging from contacting the beam portion (1210) at least sufficiently to permit translational movement of the connector (1204). To control the contact of the lock feature (1118) with the beam portion (1210), the actuator (1116) includes a lever (1120) that is rotated. Rotation of the lever (1120) causes the lock feature (1118) to move toward or away from the beam portion (1210) depending on the direction the lever (1120) is rotated. The actuator (1116) includes a threaded rod (1122) that extends through a threaded bore (1124) in the body (1102) of the central head support (1100). The lever (1120) includes a threaded bore (1126) that engages the threaded rod (1122). The threaded rod (1122) connects with the lock feature (1118). Rotating the lever (1120) rotates the threaded rod (1122) such that the threaded rod (1122) translates within the threaded bore (1124) of the body (1102) toward or away from the beam portion (1210) based on the direction of rotation. The translation of the threaded rod (1122) toward the beam portion (1210) drives the lock feature (1118) into contact with the beam portion (1210) of the connector (1204) to thereby secure the position of the connector (1204) relative to the central head support (1100). In a similar manner, translation of the threaded rod (1122) away from the beam portion (1210) moves the lock feature (1118) away the beam portion (1210) to permit adjustment of the connector (1204). In the configuration described above, the adjustable movement of the connector (1204) is along or parallel to the plane defined by the central head support (1100). In view of the teachings herein, other ways to connect the positioning assembly (1200) with the central head support (1100) will be apparent to those of ordinary skill in the art.

The connector (1204) of the positioning assembly (1200) further connects with the cassette carrier (1202). The connector (1204) includes a slot (1212) that is configured to receive a flange (1214) of the cassette carrier (1202). In the present example, a profile of flange (1214) has a complementary shape to a profile of the slot (1212). For instance, the flange (1214) and slot (1212) together form a dovetail interface. In this manner the cassette carrier (1202) is translatable along the slot (1212) of the connector (1204), which thereby adjusts the spacing between the skull clamp (1001) that connects with the cassette carrier (1202) as discussed below, and the central head support (1100).

The connection between the cassette carrier (1202) and the connector (1204) is further configured for rotational adjustment in addition to the translational adjustment mentioned above. For instance, the flange (1214) of the cassette carrier (1202) is rotatable within the slot (1212) of the connector (1204). This rotational movement allows for the cassette carrier (1202) as well as the skull clamp (1001) attached thereto as will be discussed below to be rotationally adjusted relative to the connector (1204) and central head support (1100) attached thereto as discussed above. Therefore, in the present example, the positioning assembly (1200) is configured to provide for adjusting the skull clamp (1001) relative to the central head support (1100) rotationally as well as translationally. This allows for the skull clamp (1001) to be raised and lowered relative to the central head support (1100), and patient's head resting thereon. This also allows for the skull clamp (1001) to be rotated about the patient's head resting upon the central head support (1100). Moreover this dual adjustment is provided for in a single connection interface within the positioning assembly (1200) between the cassette carrier (1202) and the connector (1204). In terms of the range of adjustability for rotation of the cassette carrier (1202) with connected skull clamp (1001) relative to the central head support (1100), in the present version, the skull clamp (1001) can be rotated in either direction up to about forty-five degrees offset from the central axis (A1) defined by the central head support (1100). In view of the teachings herein, other ways to adjust the skull clamp (1001) relative to the central head support (1100) greater and lesser amounts or degrees will be apparent to those of ordinary skill in the art.

The positioning assembly (1200) further incudes the actuator (1206). The actuator (1206) is configured to selectively secure the position, both rotational position and translational position, of the cassette carrier (1202) with the connector (1204). With the configuration described and illustrated, the actuator (1206) is configured to selectively secure the position of the skull clamp (1001), both rotational position and translational position, relative to the central head support (1100). Moreover, the single actuator (1206) is configured to selectively secure both these adjustments substantially simultaneously.

In the illustrated version, the actuator (1206) comprises a threaded rod (1216) connected with a knob (1218). The cassette carrier (1202) comprises a threaded bore (1220) configured to receive the threaded rod (1216) of the actuator (1206). The threaded bore (1220) extends all the way through the cassette carrier (1202) from one side to the other. In the present example, the threaded bore (1220) extends through the flange (1214), with the end of the threaded rod (1216) contacting the connector (1204) within the slot (1212).

Rotating the knob (1218) of the actuator (1206) translates the cassette carrier (1202) toward or away from the connector (1204) depending on the direction the knob (1218) is rotated based on the threaded engagement between the threaded rod (1216) and the threaded bore (1220). By translating the cassette carrier (1202) toward the connector (1204), the flange (1214) moves toward the connector (1204) and a sufficient gap or space is created at the interface of the flange (1214) and slot (1212) of the connector (1204) so that the cassette carrier (1202) can be rotationally and translationally adjusted as described above. By using the actuator (1206) to translate the cassette carrier (1202) away from the connector (1204), the flange (1214) moves away from the connector (1204) such that it contacts an inner wall (1222) of the slot (1212) creating an interference between the flange (1214) and the slot (1212) so that the flange (1214) binds against the inner wall (1222) of the slot (1212) to secure the cassette carrier (1202) relative to the connector (1204). This secures both the rotational position as well as the translational position.

In the present example, rotation of the actuator (1206) only requires minimal rotational movement to move the positioning assembly (1200) from the adjustable to fixed states. For instance, by way of example only, and not limitation, in one version the positioning assembly (1200) can be moved from an adjustable to a fixed state with as little as one quarter rotation of the knob (1218) of the actuator (1206). Of course in other versions, the positioning assembly (1200) may be configured such that greater or less rotation of the actuator (1206) may be used to move the positioning assembly (1200) from an adjustable to a fixed state.

Figure 26:
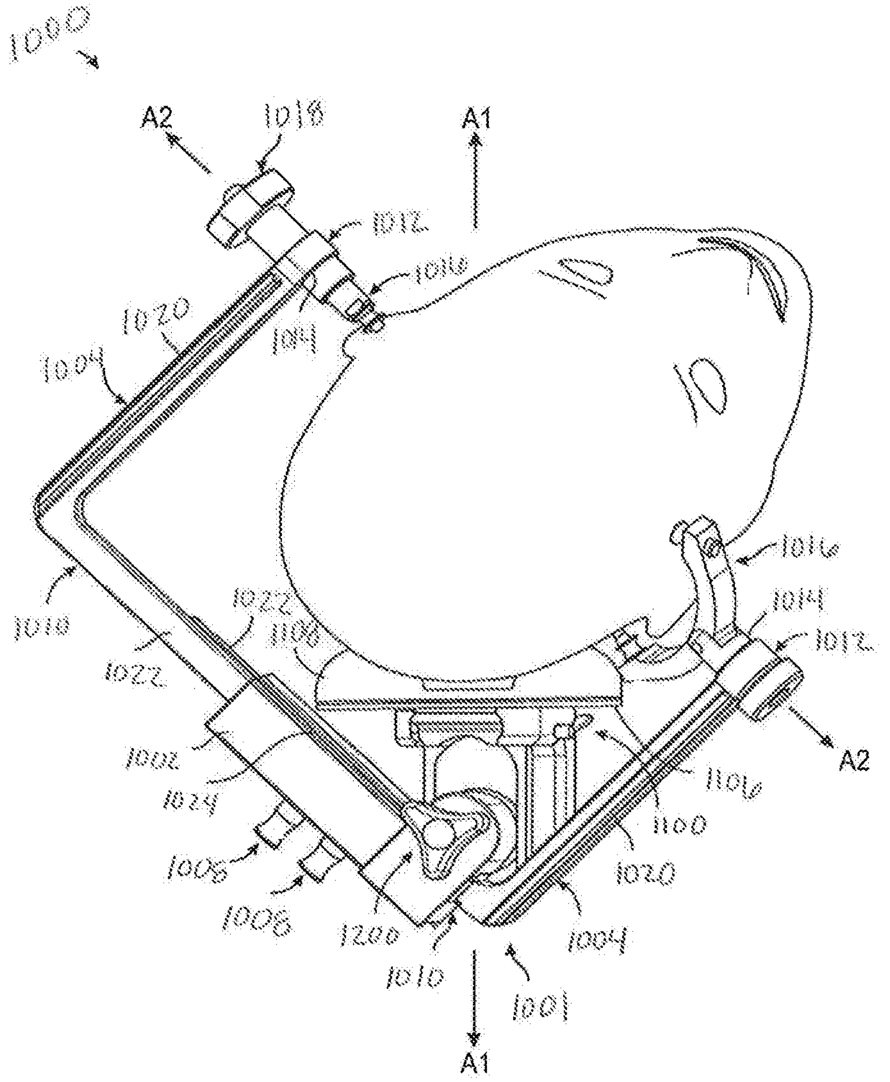
FIG. 26 depicts a perspective view of another exemplary HFD having cassette features.
Figure 27:
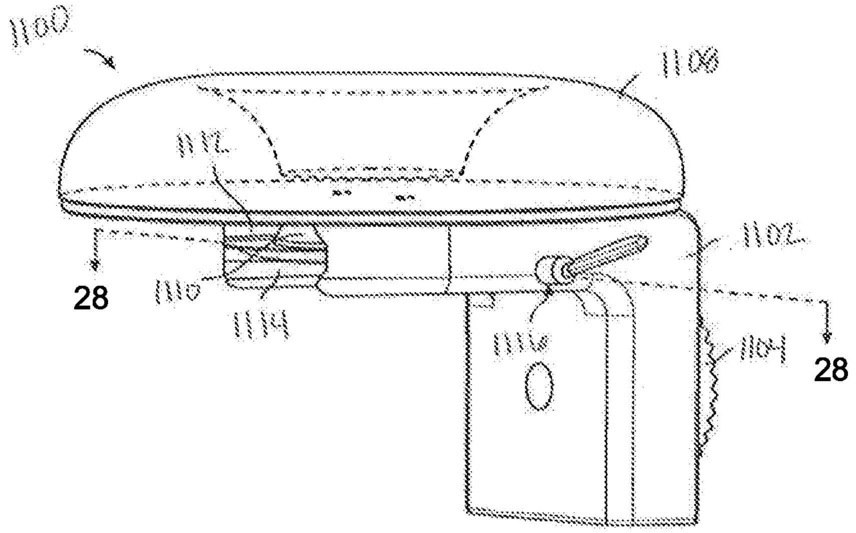
FIG. 27 depicts a partial perspective view of the HFD of FIG. 26, showing a central head support of the HFD.
Figure 28:
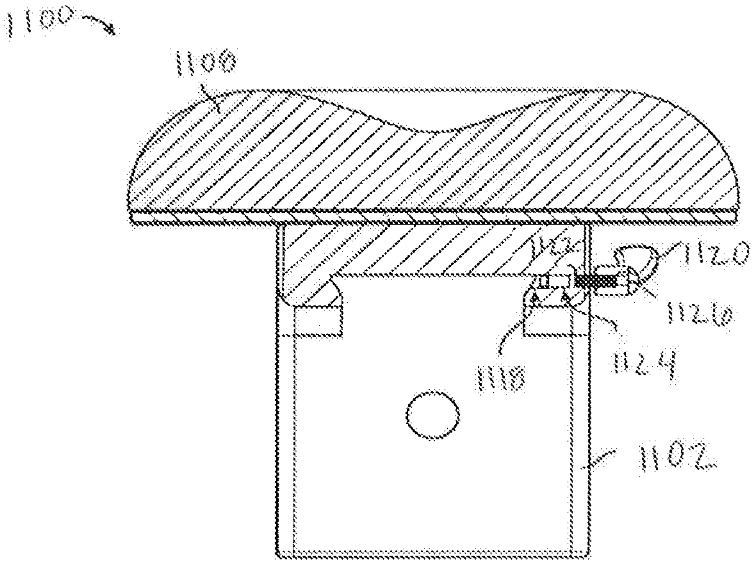
FIG. 28 depicts a front view of the HFD of FIG. 27 in cross section taken along the line 28-28 of FIG. 27.

As shown in FIG. 26, the skull clamp (1001) connects with the positioning assembly (1200). More specifically, the skull clamp (1001) connects with the positioning assembly (1200) in such a manner that the skull clamp (1001) is selectively moveable or adjustable relative to the positioning member (1200). In the illustrated version, the cassette carrier (1202) comprises a pair of sidewalls (1224) that define a space (1225) configured to receive a cassette (1002) of the skull clamp (1001). The cassette carrier (1202), on each sidewall (1224) includes an inward protrusion (1226) sized such that the cassette (1002) is held from beneath by the two protrusions (1226). With this configuration, the cassette (1002) is translatable relative to the cassette carrier (1202) and the translation occurs along a longitudinal axis defined by the cassette (1002). By moving or adjusting the skull clamp (1001) relative to the positioning assembly (1200) in this manner, since the positioning assembly (1200) connects with the central head support (1100), the position of the skull clamp (1001) is adjustable relative to the central head support (1100). Furthermore, as shown in FIG. 26 for example, it is possible to adjust the skull clamp (1001) rotationally by up to at least about forty-five degrees offset from the central axis (Al), and also keep the skull clamp (1001) centered about the cushion (1108) of the central head support (1100) by adjusting the position of the cassette (1002) relative to the cassette carrier (1202). Keeping the skull clamp (1001) centered about the cushion (1108) allows for a more stable stabilization of the patient's head resting upon the cushion (1108).

Furthermore, when a patient's head is supported by the central head support (1100), in at least some examples, movement of the skull clamp (1001) rotationally—based on rotating the cassette carrier (1202) relative to the connector (1204)—and in combination translationally—based on translation of the cassette (1002) relative to the cassette carrier (1202)—alters a position of the skull clamp (1001) concentrically, or substantially concentrically, about the head of the patient. In similar terms, a patient defines a sagittal plane that divides the patient into left and right sides, and an axis that extends longitudinally along the sagittal plane is considered a longitudinal axis defined by the patient. Generally this longitudinal axis extends from the head of the patient to the foot of the patient. In at least some examples, movement of the skull clamp (1001) as described above alters a position of the skull clamp (1001) about this longitudinal axis defined by the patient. As mentioned above, in some instances the skull clamp (1001) is adjustable in either direction relative to the central head support (1100) and the patient's longitudinal axis up to about forty-five degrees from the central axis (A1) defined by the central head support (1100). In this manner, the HFD (1000) permits semi-lateral positioning of the skull clamp (1001) on either side of the head of the patient supported by the central head support (1100) up to about forty-five degrees. In view of the teachings herein, modifications to the HFD (1000) to achieve adjustments of greater than or less than about forty-five degrees will be apparent to those of ordinary skill in the art.

Turning now to further details of the skull clamp (1001) as shown in FIG. 26, the skull clamp (1001) comprises the cassette (1002), and a pair of extension bars (1004). The cassette (1002) comprises a pair of openings (1006) configured to receive the extension bars (1004). The extension bars (1004) are independently moveable relative to the cassette (1002) and each other. Furthermore, the cassette (1002) comprises a pair of locks (1008) that are configured to engage a respective extension bar (1004) to either secure the extension bar (1004) in position or permit adjustment of the extension bar (1004). In this manner, each extension bar (1004) comprises a toothed rack (1010) and each lock (1008) comprises a complementary shaped toothed portion residing within the cassette (1002) that is moveable to engage or disengage the toothed rack (1010) with which it is associated. For instance, the locks (1008) are initially biased by a spring or other structure such that the toothed portion will engage with the toothed rack (1010) and thus lock or secure the position of the extension bar (1004) relative to the cassette (1002). Each lock (1008) may be pulled downward or away from the cassette (1002) to disengage the toothed portion of the lock (1008) from the toothed rack (1010) and thereby permit lateral movement of the extension bar (1004) relative to the cassette (1002) and the other extension bar (1004). In this manner cassette (1002) can be considered to be a locking member.

In the present example, the extension bars (1004) are interchangeable such that one may replace the other in terms of its position within the cassette (1002). Each extension bar (1004) further comprises an upper end portion (1012) having a bore (1014) configured to receive a stabilizing assembly (1016). The stabilizing assemblies (1016) are configured to contact the head of the patient and provide lateral support and stabilization to the head of the patient. In the present example, the stabilizing assembly (1016) may take the form of a single pin or a dual pin assembly. Furthermore, the stabilizing assembly (1016) may include a torque screw (1018) for adjusting the force or pressure applied to the patient's head by the stabilizing assemblies (1016). In other versions, stabilizing assemblies (1016) may take the form of a single or multi-chamber pad. Returning to the present example, each extension bar (1004) comprises an upright portion (1020) and a base (1022) with the upright portion (1020) defining a longitudinal axis. In the present example, each respective bore (1014) is offset from the longitudinal axis defined by the upright portion (1020) of each respective extension bar (1004). Furthermore, when the extension bars (1004) are positioned within the cassette (1002) the bores (1014) are offset in opposite directions such that they align and share a common axis (A2) that extends through each bore (1014). Additionally, each of the extension bars (1004) defines a rail configured to receive one or more accessories positionable along at least a portion of the extension bar (1004).

Figure 32:
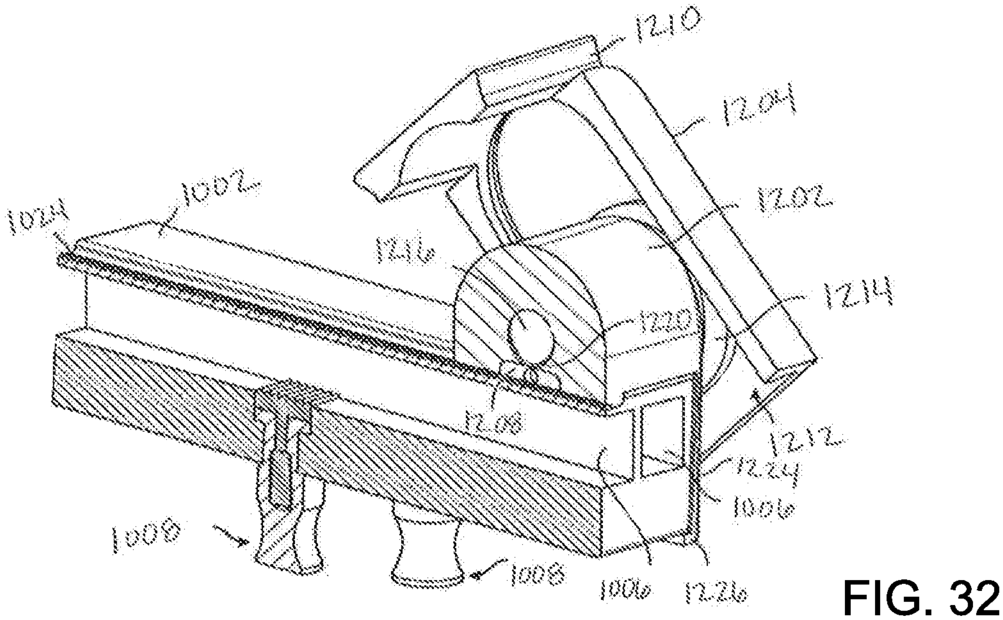
FIG. 32 depicts a cross section view taken along line 32-32 of FIG. 30.

As mentioned above, the cassette (1002) of the skull clamp (1001) is configured to selectively translate relative to the cassette carrier (1202) of the positioning assembly (1200). Referring to FIGS. 26 and 32, in the present example, the cassette (1002) further comprises a toothed rack (1024). The cassette carrier (1202) further comprises a locking insert (1208). The locking insert (1208) comprises a toothed rack that complements, and is configured to selectively engage with, the toothed rack (1024) of the cassette (1002). When the locking insert (1208) is in a disengaged position the cassette (1002) can be translated relative to the cassette carrier (1202). As described above, this translational movement provides for adjustment of the skull clamp (1001) relative to the central head support (1100). When the locking insert (1208) is in an engaged position where its toothed rack engages with the toothed rack (1024) of the cassette (1002), the cassette (1002) is fixed or secured relative to the cassette carrier (1202). When secured, the skull clamp (1001) is secured relative to the central head support (1100) so that it cannot translate along the longitudinal axis of the cassette (1002) relative to the positioning assembly (1200).

Figure 29:
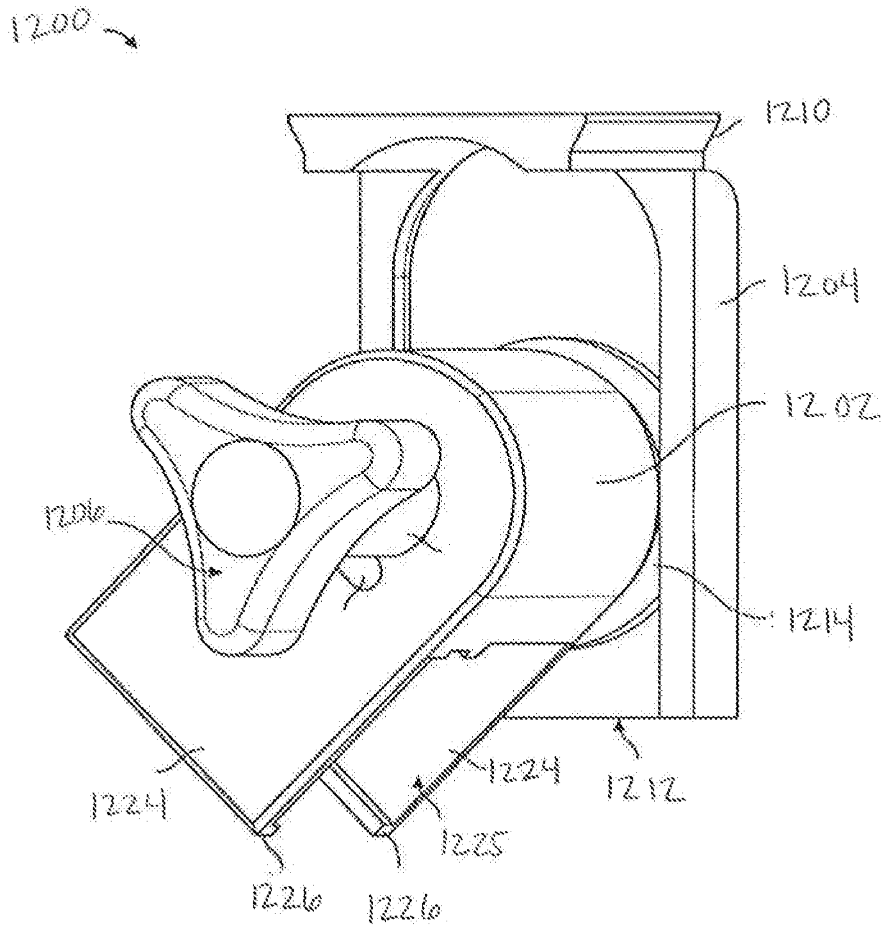
FIG. 29 depicts a partial perspective view of the HFD of FIG. 26, showing a positioning assembly of the HFD.
Figure 30:
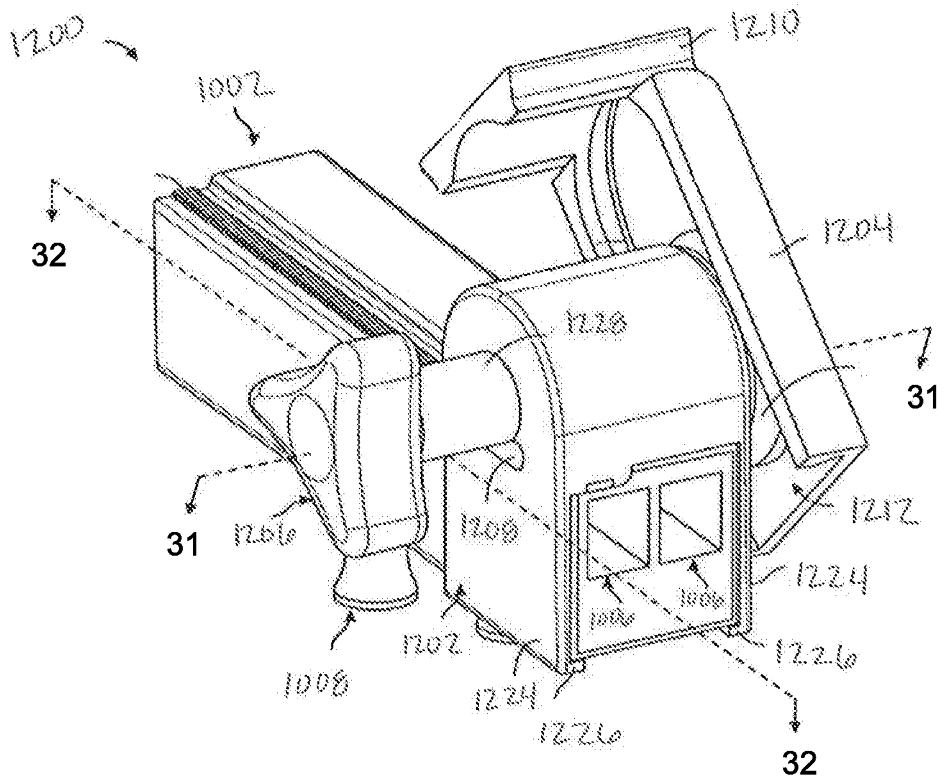
FIG. 30 depicts a partial perspective view of the positioning assembly of FIG. 29 connected with a portion of the skull clamp.
Figure 31:
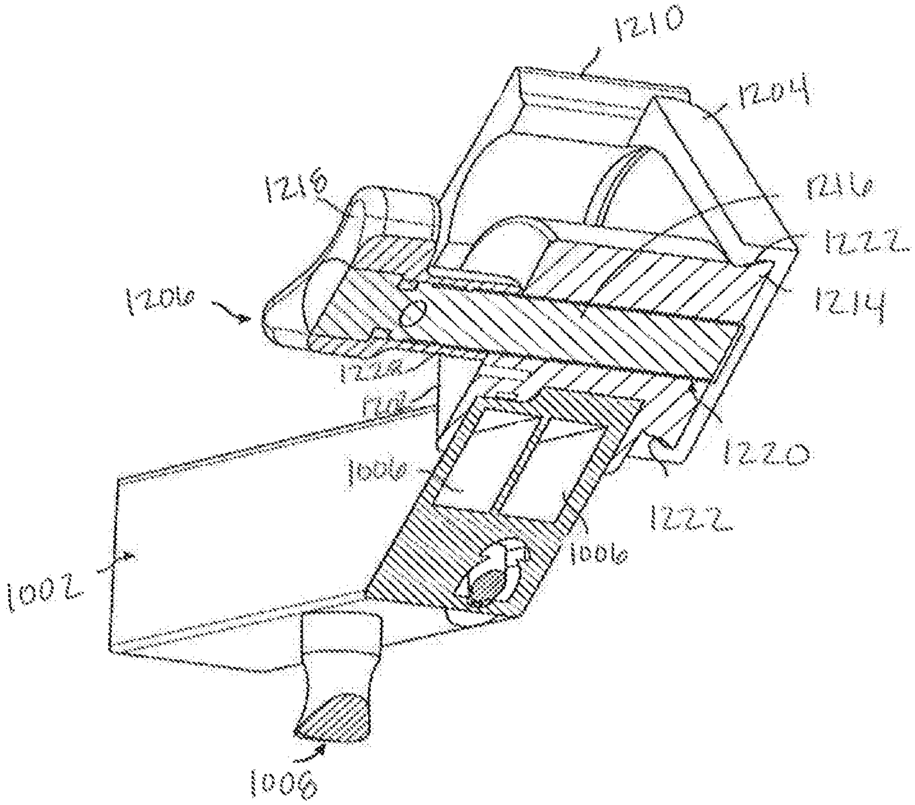
FIG. 31 depicts a cross section view taken along line 31-31 of FIG. 30.

Referring to FIGS. 29 and 30, the locking insert (1208) is held in place with the cassette carrier (1202) by an interference fit with a collar (1228) of the actuator (1206). In the present version, loosening the actuator (1206) such that the position assembly (1200) can be adjusted as discussed above, further loosens the interference fit between the collar (1228) and the locking insert (1208). Thus in this state, the locking insert (1208) may slide outward, away from the space (1225) defined by the sidewalls (1224) of the cassette carrier (1202). This movement of the locking insert (1208) causes the toothed rack of the locking insert (1208) to disengage from the toothed rack (1024) of the cassette (1002) so that the cassette (1002) can be adjusted relative to the cassette carrier (1202) as discussed above. When the actuator (1206) is tightened such that the position assembly (1200) is not adjustable as discussed above, the collar (1228) of the actuator (1206) pushes against the locking insert (1208) so that the locking insert (1208) is fully inserted or seated within the cassette carrier (1202). In this state the toothed rack of the locking insert (1208) engages the toothed rack (1024) of the cassette (1002) so that the cassette (1002) is fixed or secured relative to the cassette carrier (1202) as discussed above.

The above configuration describes and shows the adjustability of the skull clamp (1001) relative to the central head support (1100) via the rotation and translation of the flange (1214) of the cassette carrier (1202) within the slot (1212) of the connector (1204), and via the translation of the cassette (1002) relative to the cassette carrier (1202). Furthermore, in the present version, actuation of the single actuator (1206) causes the HFD (1000) to be in the adjustable state or fixed state depending on the mode of actuation. In this manner, the actuator (1206) is operable to substantially simultaneously lock or unlock the HFD (1000) for adjustment with respect to three different adjustments. In other versions such substantially simultaneous locking and unlocking adjustment capability is not required, and this may occur sequentially. Also in some other versions, the locking insert (1208) may be removed or inserted within the cassette carrier (1202) when the actuator (1206) is backed out far enough from the cassette carrier (1202) such that there is sufficient space between the collar (1228) and the cassette carrier (1202) within which to place and insert or remove the locking insert (1208) from the cassette carrier (1202). In view of the teachings herein, other ways to modify the actuator (1206) and its operability will be apparent to those of ordinary skill in the art.

VIII. Exemplary Pressure Control Pivoting Cushion

Figure 33:
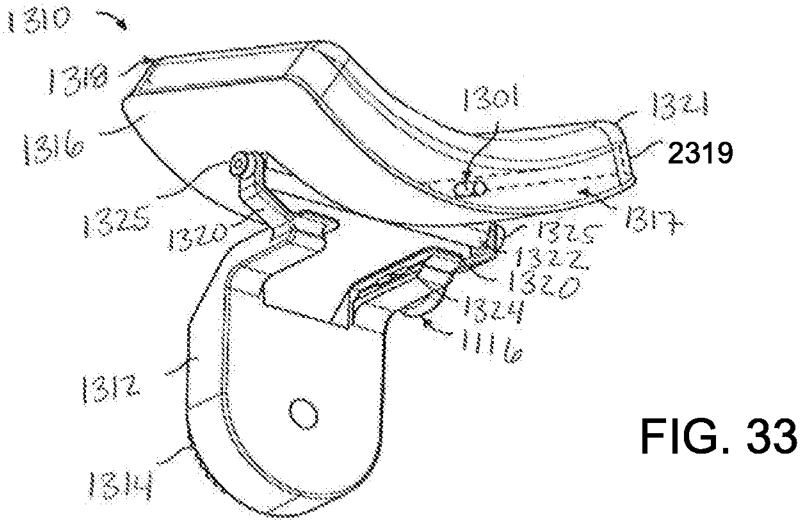
FIG. 33 depicts a perspective view of another exemplary central head support usable with the HFD of FIG. 26.

In providing HFDs with ample adjustability to accommodate various patient positioning, another desirable feature can be to incorporate a selective pivot adjustment to the cushion of the HFD. Other features that can be incorporated into the cushion pertain to management or control of the contact pressure between the cushion and the patient. FIG. 33 depicts a central head support (1310) that can be used in place of the central head support (1100) of the HFD (1000). The central head support (1310) incorporates a pivoting cushion feature and features that aid in controlling contact pressure.

[000156] The central head support (1310) comprises a slot (1324) that receives the beam portion (1210) of the connector (1204) of the positioning assembly (1200). The central head support (1310) further comprises a body (1312) and an attachment feature (1314) on the body (1312), where the attachment feature (1314) is in the form of a starburst configured to connect with an operating table or other structure directly or indirectly via one or more intermediate structures. For example, in some instances a base unit, such as those available from pro med instruments GmbH, attaches to an operating table and the attachment feature (1314) connects with the base unit. In some instances an adapter, such as a swivel adapter or other adapter available from pro med instruments GmbH, may connect with the base unit, and the attachment feature (1314) of the central head support (1310) connects with the adapter. In view of the teachings herein, various ways to connect the central head support (1310) with a stable structure such as an operating table, etc. will be apparent to those of ordinary skill in the art.

The central head support (1310) also comprises a base (1316) that connects with the body (1312) and that holds or retains a cushion (1318). The cushion (1318) may connect with the base (1316) by way of an adhesive, mechanical fasteners such as screws or hook and loop, or other ways that will be apparent to those of ordinary skill in the art. In some versions, the cushion (1318) is selectively connected with the base (1316) such that the cushion (1318) may be disposable or may be removed for cleaning and sterilization after use. The cushion (1318) is configured to contact the head of the patient when the HFD (1000) is used to support and stabilize the patient. In the present example, the base (1316) connects with the body (1312) by way of a pair of arms (1320) that extend from the body (1312) outward and upward. The base (1316) comprises a connection member (1322) defining an axis extending transversely across the base (1316). The connection member (1322) comprises a pair of bores and each bore aligns with a respective bore in each of the arms (1320). The axis defined by the connection member (1322) extends along the bores of the connection member (1322) such that the axis defines a pivoting axis about which the base (1316) and connected cushion (1318) are pivotable. A pair of fasteners (1325) extend through the bores of the arms (1320) and engage the bores of the connection member (1322) to pivotably connect the base (1316) with the body (1312) of the central head support (1310). The fasteners (1325) may be tightened to secure the position of the base (1316) and connected cushion (1318), and conversely the fasteners (1325) may be loosened to permit pivotable adjustment of the base (1316) and connected cushion (1318).

In use, the central head support (1310) is configured to provide subjacent support to the head of the patient. In this manner, the central head support (1310) defines a plane that extends subjacent to the head of the patient when the head of the patient is supported by the central head support. In the present example, the central head support (1310) is positioned such that the plane defined by the central head support (1310) may be adjusted based on the pivoting action of the base (1316) and connected cushion (1318). Therefore, the plane defined by the central head support (1310) is not limited to being parallel to a floor, or orthogonal to a direction of gravitational force on the central head support (1310).

The central head support (1310) is configured to adjust a spacing between the central head support (1310) and positioning assembly (1200) in the same manner as discussed above with respect to the central head support (1100) and the positioning assembly (1200). For instance, the connector (1204) adjustably connects with the body (1312) of the central head support (1310). As illustrated, within the body (1312) is a slot (1324). The slot (1324) receives the beam portion (1210) of the connector (1204). The profile of the beam portion (1210) has a complementary shape to the slot (1324). In the present example the beam portion (1210) and slot (1324) together form a dovetail interface. In this manner the connector (1204) is translatable along the slot (1324), which adjusts the spacing between the positioning assembly (1200) and the central head support (1310). To control the adjustability of the connector (1204) within the slot (1324), the central head support (1310) comprises the actuator (1116) and the lock feature (1118), which are configured and operable in the same manner as described above. In this configuration, the connector (1204) is adjustable along or parallel to the plane defined by the central head support (1310) to change a position of the positioning assembly (1200) relative to the central head support (1310).

The cushion (1318) comprises a first chamber (2319) having an internal space (1317) that is configured to be filled with a fluid. The fluid may be a gas or a liquid. The first chamber (2319) includes a port (1301) that is configured to provide access to the internal space (1317). The fluid may be directed to the internal space (1317) within the first chamber (2319) or extracted from or vented from the internal space (1317) of the first chamber (2319). When venting fluid from the first chamber (2319), all or a portion of the fluid may be released or vented from the internal space (1317).

The cushion (1318) further comprises a second chamber (1321), which is configured to be filled with a shape-conforming material. In the present example, the first chamber (2319) is positioned subjacent to the second chamber (1321). Furthermore, the second chamber (1321) is configured to contact the patient's head. In view of the teachings herein, it will be apparent to those of ordinary skill in the art that the relative positions of the first and second chambers (2319, 1321) may be switched in other versions. In one version, the shape-conforming material is one of either a gel, a foam, or a granule material. In view of the teachings herein, other shape- conforming materials usable with the cushion (1318) will be apparent to those of ordinary skill in the art.

With the configuration of the cushion (1318) described above, the cushion (1318) is configured to provide a uniform distribution of contact pressure with the head of the patient when the head is supported by the central head support (1310). Moreover, the contact pressure can be increased by filling the first chamber (2319) with fluid via the port (1301) when the system is configured for use with skull pins.

Conversely, the contact pressure can be decreased by venting the fluid from the first chamber (2319) as mentioned above. By reducing the contact pressure, blood flow can be restored to the area of the patient's head in contact with the cushion (1318). In some instances, but not required in all versions, substantial venting of the fluid from the first chamber (2319) may cause the cushion (1318) to deflate or reduce in height such that the cushion (1318) no longer contacts the head of the patient or does not apply relevant pressure to the patient's head. Similar to above, by reducing the contact pressure to the extent that the contact pressure between the cushion (1318) and the patient is lacking, blood flow can be restored to this area of the patient's head that was stabilized with the cushion (1318). By reducing contact pressure and providing for restoration of blood flow, tissue trauma or injury can be avoided or the risk reduced. Additionally, stabilization can be maintained by the stabilization assemblies (1016) when reducing contact pressure between the cushion (1318) and the patient's head so as to not sacrifice stabilization of the patient when restoring blood flow to an area of tissue. In some instances, once sufficient time has elapsed to restore blood flow to the tissue area in contact with the cushion (1318), the contact pressure can be increased again by filling the first chamber (2319) with the fluid to provide or restore an enhanced or a greater degree of stabilization.

Figure 34:
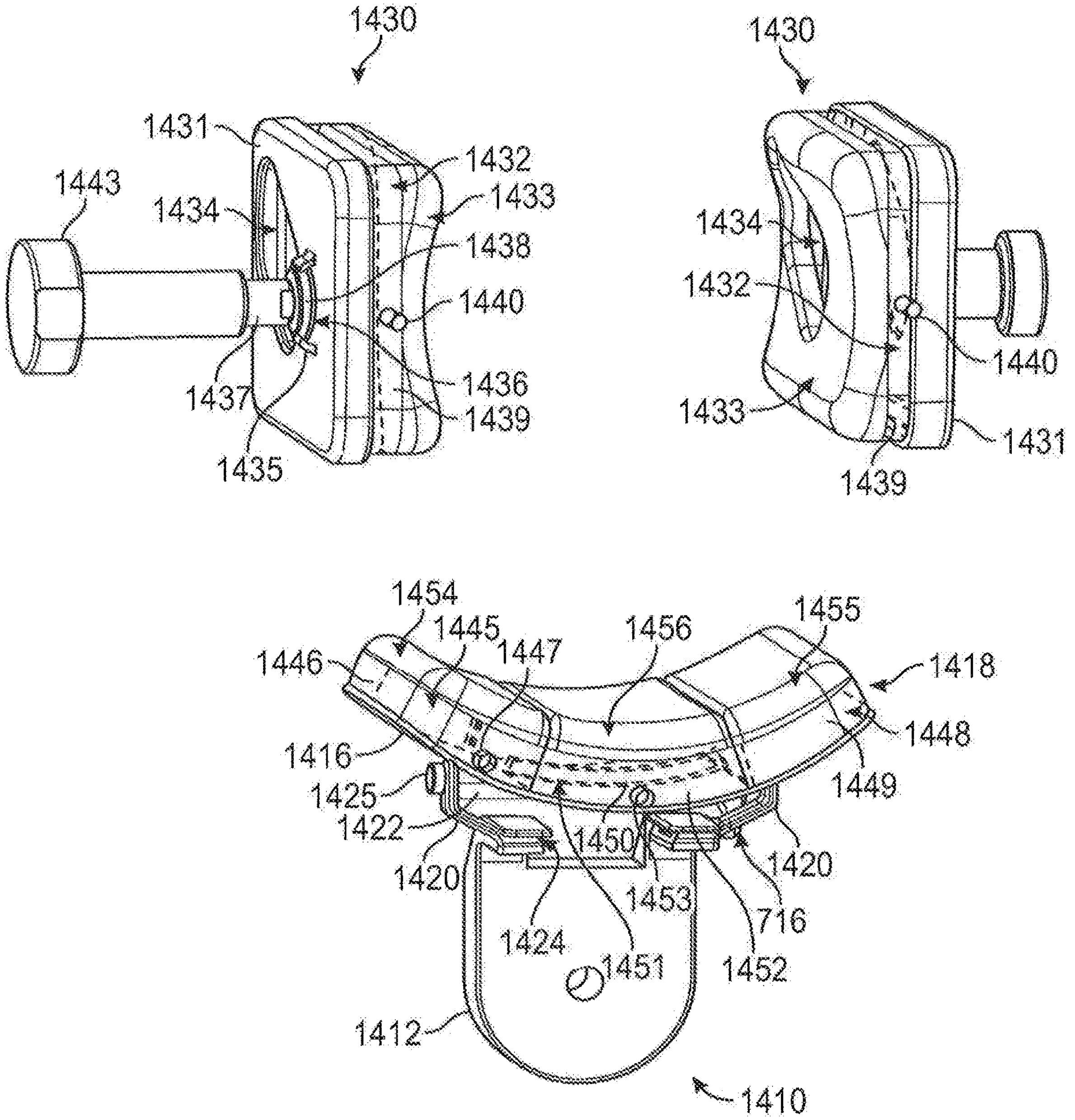
FIG. 34 depicts a perspective view of another exemplary central head support and another pair of stabilization assemblies usable with the HFD of FIG. 26.

IX. Exemplary Non-Invasive Configuration with Lateral Pads and Multi-Chamber Cushion In some instances, a non-invasive HFD configuration may be desired where the stabilization assemblies have the form of pads instead of pins, where the pads provide the lateral stabilization. Additionally, the pads may be configured with certain contact pressure control features to help promote blood flow to certain tissue areas to avoid or reduce the risk of tissue injury or trauma. FIG. 34 depicts pads (1430) for the stabilization assemblies (1016) to provide for a non-invasive stabilization with the HFD (1000). FIG. 34 also depicts a central head support (1410) that can be used in place of the central head support (1100) of the HFD (1000). The central head support (1410) incorporates a pivoting cushion feature and features that aid in controlling contact pressure, similar to the central head support (1310) described above. The central head support (1410) differs from the central heads support (1310) in that a cushion (1418) replaces the cushion (1318). Similar to the cushion (1318) described above, the pads (1430) include features that aid in controlling pressure at the stabilization contact areas where the pads (1430) contact the patient's head.

The central head support (1410) comprises a slot (1424) that receives the beam portion (1210) of the connector (1204) of the positioning assembly (1200). The central head support (1410) further comprises a body (1412) and an attachment feature on the body (1412), where the attachment feature is in the form of a starburst configured to connect with an operating table or other structure directly or indirectly via one or more intermediate structures. For example, in some instances a base unit, such as those available from pro med instruments GmbH, attaches to an operating table and the attachment feature connects with the base unit. In some instances an adapter, such as a swivel adapter or other adapter available from pro med instruments GmbH, may connect with the base unit, and the attachment feature of the central head support (1410) connects with the adapter. In view of the teachings herein, various ways to connect the central head support (1410) with a stable structure such as an operating table, etc. will be apparent to those of ordinary skill in the art.

The central head support (1410) also comprises a base (1416) that connects with the body (1412) and that holds or retains the cushion (1418). The cushion (1418) may connect with the base (1416) by way of an adhesive, mechanical fasteners such as screws or hook and loop, or other ways that will be apparent to those of ordinary skill in the art. In some versions, the cushion (1418) is selectively connected with the base (1416) such that the cushion (1418) may be disposable or may be removed for cleaning and sterilization after use. The cushion (1418) is configured to contact the head of the patient when the HFD (1000) is used to support and stabilize the patient. In the present example, the base (1416) connects with the body (1412) by way of a pair of arms (1420) that extend from the body (1412) outward and upward. The base (1416) comprises a connection member (1422) defining an axis extending transversely across the base (1416). The connection member (1422) comprises a pair of bores on each side and each bore aligns with a respective bore in each of the arms (1420). The axis defined by the connection member (1422) extends along the bores of the connection member (1422) such that the axis defines a pivoting axis about which the base (1416) and connected cushion (1418) are pivotable. A pair of fasteners (1425) extend through the bores of the arms (1420) and engage the bores of the connection member (1422) to pivotably connect the base (1416) with the body (1412) of the central head support (1410). The fasteners (1425) may be tightened to secure the position of the base (1416) and connected cushion (1418), and conversely the fasteners (1425) may be loosened to permit pivotable adjustment of the base (1416) and connected cushion (1418).

In use, the central head support (1410) is configured to provide subjacent support to the head of the patient. In this manner, the central head support (1410) defines a plane that extends subjacent to the head of the patient when the head of the patient is supported by the central head support. In the present example, the central head support (1410) is positioned such that the plane defined by the central head support (1410) may be adjusted based on the pivoting action of the base (1416) and connected cushion (1418). Therefore, the plane defined by the central head support (1410) is not limited to being parallel to a floor, or orthogonal to a direction of gravitational force on the central head support (1410).

The central head support (1410) is configured to adjust a spacing between the central head support (1410) and positioning assembly (1200) in the same manner as discussed above with respect to the central head support (1100) and the positioning assembly (1200). For instance, the connector (1204) adjustably connects with the body (1412) of the central head support (1410). As illustrated, within the body (1412) is a slot (1424). The slot (1424) receives the beam portion (1210) of the connector (1204). The profile of the beam portion (1206) has a complementary shape to the slot (1424). In the present example the beam portion (1206) and slot (1424) together form a dovetail interface. In this manner the connector (1204) is translatable along the slot (1424), which adjusts the spacing between the positioning assembly (1200) and the central head support (1410). To control the adjustability of the connector (1204) within the slot (1424), the central head support (1410) comprises the actuator (1116) and the lock feature (1118), which are configured and operable in the same manner as described above. In this configuration, the connector (1204) is adjustable along or parallel to the plane defined by the central head support (1410) to change a position of the positioning assembly (1200) relative to the central head support (1410).

The pads (1430) comprise a housing (1431), a first chamber (1432), and a second chamber (1433). A bore or cut-out (1434) extends through the housing (1431), the first chamber (1432), and the second chamber (1433). The bore (1434) is located such that it is configured to receive a patient's ear during stabilization so as to protect the patient's ear from excessive compression and pressure, and instead direct such pressure and compressive force on the patient's skull. Located on the housing (1431) is also an annular flange (1435) that defines a slot (1436) configured to connect with the remainder of the stabilizing assembly (1016). In the present example, the stabilizing assembly includes a collar (1437) having a flange (1438) that fits within the slot (1436). With this configuration, the pad (1430) can be adjusted about an axis defined by and extending through the bore (1014) as illustrated above in FIG. 26.

The first chamber (1432) of the pad (1430) defines an internal space (1439) that is configured to be filled with a fluid, which may be a liquid or gas or combination. There is also a port (1440) that can be opened and closed that connects with the first chamber (1432) and provides access to the internal space (1439) of the first chamber (1432). In this manner, the fluid can be delivered to or vented or extracted from the internal space (1439) of the first chamber (1432) by way of the port (1440).

When the pads (1430) are used with each stabilizing assembly (1016), in some versions the ports (1440) are connected by a tube, hose, or conduit (1441). The tube (1441) may be connected to a valve (1457) and further connected to a fluid reservoir (1459) as described further below. In this configuration, by connecting the first chambers (1432) of multiple pads (1430), the pressure within the first chambers (1432) is the same, and the pressure changes in the same fashion too as the first chambers (1432) may be filled with more fluid to increase the pressure, or fluid vented from the first chambers (1432) to decrease the pressure within.

The first chamber (1432) is located between the housing (1431) and the second chamber (1433). Of course in other versions, in view of the teachings herein, it will be apparent to those of ordinary skill in the art that the locations of the first chamber (1432) and the second chamber (1433) may be switched. The second chamber (1433) of the pad (1430) is configured to be filled with a shape-conforming material as described above with respect to cushion (1318). In the present example, the second chamber (1433) is positioned to be adjacent to and in contact with the head of the patient. In one version, the shape-conforming material within the second chamber (1433) is one of either a gel, a foam, a granule material or a combination of such materials. In view of the teachings herein, other shape-conforming materials usable with the second chambers (1433) of pads (1430) will be apparent to those of ordinary skill in the art.

Figure 35:
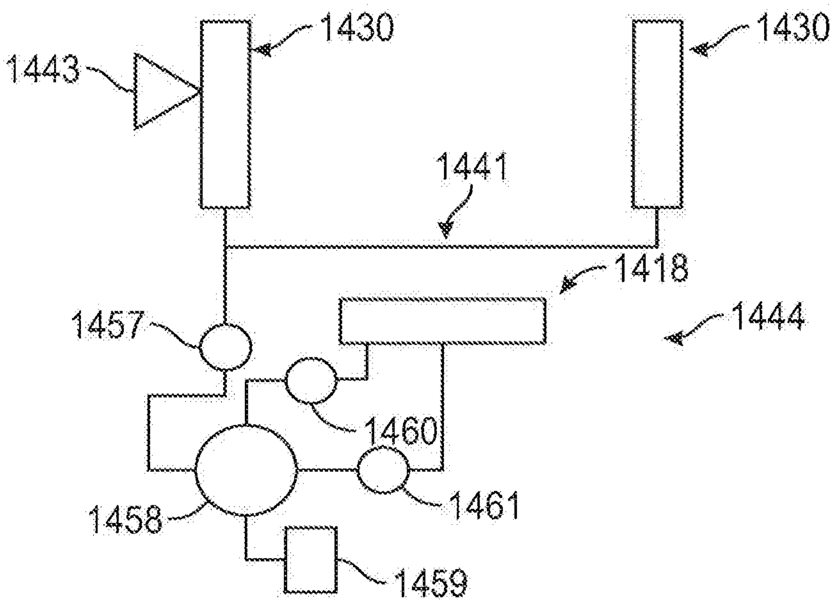
FIG. 35 depicts an exemplary fluid control system usable with the HFD of FIG. 26.

With the configuration of the pads (1430) described above, the pads (1430) are configured to provide a uniform distribution of contact pressure with the head of the patient when the head is supported by the stabilization assemblies (1016) having the pads (1430). Moreover, the contact pressure can be increased by filling the first chamber (1432) with fluid via the port (1440) or via the tube (1441) connected with the ports (1440) as shown in FIG. 35, which depicts a fluid control system (1444). Conversely, the contact pressure can be decreased by venting the fluid from the first chamber (1432) as mentioned above. By reducing the contact pressure, blood flow can be restored to the area of the patient's head in contact with the pads (1430). In some instances, but not required in all versions, substantial venting of the fluid from the first chamber (1432) may cause the pads (1430) to deflate or reduce in size such that the pads (1430) no longer apply relevant pressure to the head of the patient. Similar to above, by reducing the contact pressure to the extent that the contact between the pads (1430) and the patient is lacking, blood flow can be restored to the area of the patient's head that was in contact with the pads (1430). By reducing contact pressure and providing for restoration of blood flow, tissue trauma or injury can be avoided or the risk reduced. Additionally, support of the patient's head can be maintained by the cushion (1418) of the central head support (1410) when reducing contact pressure between the pads (1430) and the patient's head so as to not sacrifice support of the patient when restoring blood flow to an area of tissue. In some instances, once sufficient time has elapsed to restore blood flow to the tissue area in contact with the pads (1430), the contact pressure can be increased again by filling the first chambers (1432) with the fluid to provide or restore an enhanced or a greater degree of stabilization.

In some versions of the HFD (1000) configured with the pads (1430), both of the laterally positioned pads (1430) are connected via the tube (1441) and the pads (1430) are kept at the same pressure at all times within each of the pads (1430). In some other versions, it is not required to connect both the laterally positioned pads (1430) with the tube (1441), and thus each of the pads (1430) can be controlled independent from the other in terms of its pressure. Still yet, various valve placements may be incorporated with the tube (1441) such that the pads (1430), even if connected via the tube (1441), may be configured to be controlled independently. In view of the teachings herein, other ways to configure the pads (1430) and control the pressure within will be apparent to those of ordinary skill in the art. By way of example only, and not limitation, the pressure demands within the pads (1430) may differ with patient positions where the skull clamp (800) is rotated about the patient's head as described above.

In some versions of the HFD (1000) configured with the pads (1430), the pressure the pads (1430) apply to the patient's head is adjustable using a torque screw (1443). The torque screw (1443) is a component of one of the stabilizing assemblies (816). Tightening the torque screw (1443) increases the pressure applied by the pads (1430) to the patient's head. In the illustrated version, the single torque screw (1443) is on one side, and the two pads (1430) are connected by the tube (1441) such actuation of the torque screw (1443) changes the pressure in both the pads (1430). In some other versions, multiple torque screws (1443) could be used, one associated with each of the pads (1430) such that the pads (1430) may not be connected by the tube (1441). In some versions, the initial stabilization may be accomplished using the torque screw (1443). After setting the torque screw (1443) initially, subsequent pressure adjustments could be made by adjusting the amount of fluid within the first chambers (1432) of the pads (1430), e.g. by directing more fluid to the first chambers (1432) to increase the pressure, or by venting fluid from the first chambers (1432) to decrease the pressure. In other words, in some versions, whether or not the torque screw (1443) is included, the contact pressure provided by each of the pads (1430) can be controlled or adjusted separate and independent from the torque screw (1443). In some versions, the torque screw (1443) can be omitted altogether, and replaced with a conventional skull pin assembly. In view of the teachings herein, other ways to use either the torque screw (1443), a fluid control system (1444) as shown in FIG. 35, or both in combination will be apparent to those of ordinary skill in the art.

As mentioned, the HFD (1000) can be configured with the central head support (1410) having the cushion (1418). The cushion (1418) comprises a multi-chamber structure with a first chamber (1445) having an internal space (1446) that is configured to be filled with a fluid. The fluid may be a gas or a liquid. The first chamber (1445) includes a port (1447) that is configured to provide access to the internal space (1446). The fluid may be directed to the internal space (1446) within the first chamber (1445) or extracted from or vented from the internal space (1446) of the first chamber (1445). When venting fluid from the first chamber (1445), all or a portion of the fluid may be released or vented from the internal space (1446). The cushion further comprises a second chamber (1448) having an internal space (1449) that is configured to be filled with the fluid, or fluid may be extracted from or vented from the internal space (1449) of the second chamber (1448). When venting fluid from the second chamber (1448), all or a portion of the fluid may be released or vented from the internal space (1449). In the present example, the internal space (1446) of the first chamber (1445) and the internal space (1449) of the second chamber (1448) are in fluid communication by way of a connection tube (1450) that extends between the internal spaces (1446, 1449) of the first and second chambers (1445, 1448).

The cushion (1418) further comprises a third chamber (1451) positioned between the first and second chambers (1445, 1448). In this configuration, the first and second chambers (1445, 1448) collectively define a pair of outer chambers while the third chamber (1451) defines a middle chamber. The third chamber (1451) also comprises an internal space (1452), and the connection tube (1450) extends through the internal space (1452) of the third chamber (1451). The internal space (1452) of the third chamber is configured to be filled with the fluid similar to the first and second chambers (1445, 1448). The fluid may be added to or removed from the internal space (1452), which can change the pressure within this area of the cushion (1418). The third chamber (1451) comprises a port (1453) similar to the first chamber (1445). The port (1453) provides access to the internal space (1452) and is used to direct fluid to the internal space (1452) or vent fluid from the internal space (1452).

The cushion (1418) further comprises a fourth chamber (1454), a fifth chamber (1455), and a sixth chamber (1456), each configured be filled with a shape-conforming material. The first chamber (1445) is positioned subjacent to the fourth chamber (1454), and the fourth chamber (1454) is configured to contact the head of the patient. The second chamber (1448) is positioned subjacent to the fifth chamber (1455), and the fifth chamber (1455) is configured to contact the head of the patient. The third chamber (1451) is positioned subjacent to the sixth chamber (1456), and the sixth chamber (1456) is configured to contact the head of the patient. In view of the teachings herein, it will be apparent to those of ordinary skill in the art that the relative positions of the first and fourth chambers (1445, 1454), the second and fifth chambers (1448, 1455), and the third and sixth chambers (1451, 1456) may be switched in other versions. In one version, the shape-conforming material within the fourth, fifth, and sixth chambers (1454, 1455, 1456) is one of either a gel, a foam, a granule material or a combination. In view of the teachings herein, other shape-conforming materials usable with the cushion (1418) will be apparent to those of ordinary skill in the art.

With the configuration of the cushion (1418) described above, the cushion (1418) is configured to provide a various pressure profiles depending on the manner of adjustments with the fluid and each of the respective internal spaces (1446, 1449, 1452). For instance, in some versions, a uniform distribution of contact pressure can be achieved where the third chamber (1451) is configured to hold the same amount of fluid per unit of volume within the internal space (1452) as in the internal spaces (1446, 1449) of the first and second chambers (1445, 1448). Still in other versions, the outer chambers may have matching pressures while the middle chamber has a pressure that may be higher or lower than the pressure within the outer chambers. Furthermore, in this configuration with differing pressures between the outer chambers and the middle chamber, the fluid may be vented and/or added in a controlled fashion to provide a way to promote blood flow to an area of the patient's tissue in contact with a portion of the cushion (1418) while maintaining secure stabilization of the patient's head.

By way of example only, and not limitation, in one version, a patient is initially stabilized with the pads (1430) applying the same contact pressure to portions of the patient's head. In the initial stabilization, the cushion (1418) is configured such that the outer chambers and middle chamber also apply the same contact pressure to the back portion of the patient's head. In this example the HFD (1000) is used with the patient in a supine position, but this is not necessary in all examples such that the HFD (1000) may be used with the patient in other positions. After some time has passed, the pressure within the pads (1430) and/or the cushion (1418) can be manipulated so that blood flow can be restored or increased to the areas where the tissue of the patient's head contacts portions of the HFD (1000). Moreover, this manipulation of pressure comprises a short term relief or reduction of pressure to promote increased blood flow to the tissue, followed by an increase in pressure after a period of time has passed to provide for enhanced stabilization. Furthermore, this manipulation of pressure can be performed in an alternating fashion among the pads (1430) and/or chambers of the cushion (1418). By using this alternating fashion, the tissue areas in contact with the HFD (1000) are treated with restored or increased blood flow while maintaining an acceptable degree of stabilization.

An example of the alternating pressure relief and restoration sequence can include as a first step, after an initial stabilization is configured, reducing the pressure in the pads (1430) to give an amount of time to restore blood flow to the portions of the patient's head contacted by pads (1430). Note that in some such examples the pressure in the pads (1430) may not be reduced at all, and the pressure relief sequence may be limited to the multi-chamber cushion (1418). Note also that in other examples, the first step may be to perform a pressure relief step or process on the multi-chamber cushion (1418) and thereafter perform a pressure relief step on one or both of the pads (1430). In the present example, however, after the pressure in the pads (1430) has been reduced and some time has passed where blood flow has been increased to the tissue areas of the patient in contact with the pads (1430), the pressure in the pads (1430) is then restored to its initial level.

Thereafter, the middle chamber defined by the third chamber (1451) is vented to reduce its pressure. This action reduces the force or pressure applied to the patient's head at the middle chamber and thus allows for increased blood flow to this back area of the patient's head in contact with the middle chamber. In this case, the outer chambers, defined collectively by the first and second chambers (1445, 1448), remain at their original or initial pressure, or experience a higher pressure. Thus the outer chambers and the pads (1430) provide stabilization to the patient's head while the tissue area in contact with the middle chamber is receiving a period of increased or restored blood flow to prevent or reduce the risk of tissue trauma in this area.

For the sake of further clarity, the middle chamber of the cushion (1418) comprises both the third chamber (1451) that is configured to contain the fluid, as well as the sixth chamber (1456) that is configured with the shape-conforming material. Similarly, with the pair of outer chambers, one of the outer chambers comprises the first chamber (1445) that is configured to contain the fluid, as well as the fourth chamber (1454) that is configured with the shape-conforming material. And the other of the outer chambers comprises the second chamber (1448) that is configured to contain the fluid, as well as the fifth chamber (1455) that is configured with the shape-conforming material. As will be understood in view of the teachings herein, the pressure relief discussed above within the outer chambers and the middle chamber occurs by changing the fluid volume within the respective internal spaces (1446, 1449, 1452) of the first, second, and third chambers (1445, 1448, 1451), while the increase in blood flow based on the pressure relief occurs at the tissue areas in contact with the respective fourth, fifth, and sixth chambers (1454, 1455, 1456) having the shape-conforming material. In other configurations, the fluid-filled chambers may be the chambers in contact with the patient's head while the shape-conforming containing chambers may be located beneath or subjacent to the respective fluid-filled chambers. In view of the teachings herein, other configurations for the chambers will be apparent to those of ordinary skill in the art.

Returning again to the example above of a pressure relief sequence, after the pressure in middle chamber of the cushion (1418) has been reduced and some time has passed where blood flow has been increased to the tissue area of the patient in contact with the middle chamber, and specifically the sixth chamber (1456), the pressure in the middle chamber of the cushion (1418) is then restored to its initial level. Thereafter, the pair of outer chambers are vented to reduce their pressure by venting or extracting fluid from the respective first and second chambers (1445, 1448). This action reduces the force or pressure applied to the patient's head at the outer chambers, and thus allows for increased blood flow to these areas of the patient's head in contact with the outer chambers, and more specifically at the areas of contact with the respective fourth and fifth chambers (1454, 1455). In this case, the middle chamber experiences a higher pressure, while the pads (1430) remain at their original or initial pressure. Thus the middle chamber and the pads (1430) provide stabilization to the patient's head while the tissue area in contact with the outer chambers is receiving a period of increased or restored blood flow to prevent or reduce the risk of tissue trauma in this area.

After the pressure in outer chambers of the cushion (1418) has been reduced and some time has passed where blood flow has been increased to the tissue area of the patient in contact with the outer chambers, and specifically the fourth and fifth chambers (1454, 1455), the pressure in the outer chambers of the cushion (1418) is then restored to its initial level. The above described pressure relief process can be conducted multiple times as needed or desired to help reduce the risk of tissue injury or trauma. Moreover, these pressure relief actions can be completed in any order as the circumstances require or dictate such that the example order described above should not be considered a required order or the only order or sequence.

With the HFD (1000) configured with the pads (1430) and the central head support (1410) as described above, the fluid connection between the first chambers (1432) of the pads (1430) via the tube (1441) allows for the pressure in each of the pads (1430) to be the same and to be simultaneously adjusted such that while the pressure in the pads (1430) changes, it does so in the same manner and to the same degree. With the pads (1430) generally located on opposite sides of the patient's head, the fluid connection between the first chambers (1432) of the pads (1430) allows for pressure changes within the pads (1430) to promote blood flow to the tissue areas contacted by the pads (1430) without altering the differential in the force that is applied to the opposing sides of the patient's head by the respective pads (1430). This configuration allows for the pressure changes within the pads (1430) without causing the patient's head to move or change position.

For instance, in one example, the initial force applied to each side of the patient's head by each of the pads (1430) may be 20 newtons, and thus the differential in force would be zero because the force applied by each of the pads (1430) is the same. When an example pressure relief process has been performed, the force applied to each side of the patient's head by each of the pads (1430) may now be 50 newtons, and thus the differential in force maintained at zero because the force applied by each of the pads (1430) remains the same. Again, while in the present example the pads (1430) may be fluidly connected by the tube (1441), this is not required in all versions. For instance, in some other versions the pads (1430) may be independently adjustable or controllable regarding their pressure based on fluid volumes within the first chambers (1432).

Similar to the pads (1430), the fluid connection between the first chamber (1445) and the second chamber (1448) of the cushion (1418) via the connection tube (1450) allows for the pressure in each of the outer chambers of the cushion (1418) to be the same and to be simultaneously adjusted such that while the pressure in the outer chambers of the cushion (1418) changes, it does so in the same manner and to the same degree. As shown and described, the outer chambers of the cushion (1418) are generally located on opposite sides of the sagittal plane of the patient's head when in the supine position such that the outer chambers of the cushion (1418) are symmetrically located about the sagittal plane dividing the patient's head into left and right portions. The fluid connection between the outer chambers of the cushion (1418) allows for pressure changes within the outer chambers of the cushion (1418) to promote blood flow to the tissue areas contacted by the outer chambers of the cushion (1418) without altering the differential in the force that is applied to the patient's head by the respective outer chambers of the cushion (1418). This configuration allows for the pressure changes within the outer chambers of the cushion (1418) without causing the patient's head to move or change position, i.e. rotating about the patient's longitudinal axis because of an uneven force applied by one of the outer chambers of the cushion (1418) compared to the other outer chamber of the cushion (1418).

X. Exemplary Fluid Control Systems and Methods

FIG. 35 depicts the fluid control system (1444) usable with the HFD (1000) configured with the pads (1430) and the cushion (1418) as shown schematically. As described above in detail, the pads (1430) provide the lateral stabilization to the patient's head, and the cushion (1418) provides subjacent support and stabilization. The torque screw (1443) connects with one of the pads (1430) to permit increasing or decreasing the pressure the pad (1430) applies to the patient's head. The connection tube (1441) connects the pads (1430) together such that they are in fluid communication. As described above, the connection tube (1441) connects the first chambers (1432) of the respective pads (1430). In this configuration, the pressure in each of the pads (1430) is the same and each of the pads (1430) imparts the same force on the patient's head.

Also connected with the connection tube (1441) is a valve (1457). The valve (1457) is configured to selectively vent fluid from the pads (1430) to reduce the pressure within the pads (1430) or to permit additional fluid to flow to the pads (1430) to increase the pressure within the pads (1430). The valve (1457) connects with a pump (1458), which is configured to supply additional fluid to the pads (1430) when desired. In some versions, the pump (1458) can also be configured to direct vented or extracted fluid away from the pads (1430). In fluid communication with the pump (1458) is a fluid reservoir (1459). The fluid reservoir (1459) is configured to provide additional fluid to be delivered via the pump (1458) to the pads (1430). In some instances, venting fluid from the pads (1430) involves opening the valve (1457) and operating the pump (1458) to move fluid from the pads (1430) to the fluid reservoir (1459). The pump (1458) can also be used without the fluid reservoir (1459) such that the fluid reservoir (1459) may be omitted in some versions. In such versions, the pump (1458) may be configured to deliver air from the surrounding environment to the pads (1430). Similarly, venting fluid from the pads (1430) in such versions may involve venting air from the pads (1430) back to the surrounding environment instead of venting to the fluid reservoir (1459). In some examples, the fluid reservoir (1459) itself can be considered the surrounding environment.

Figure 37:
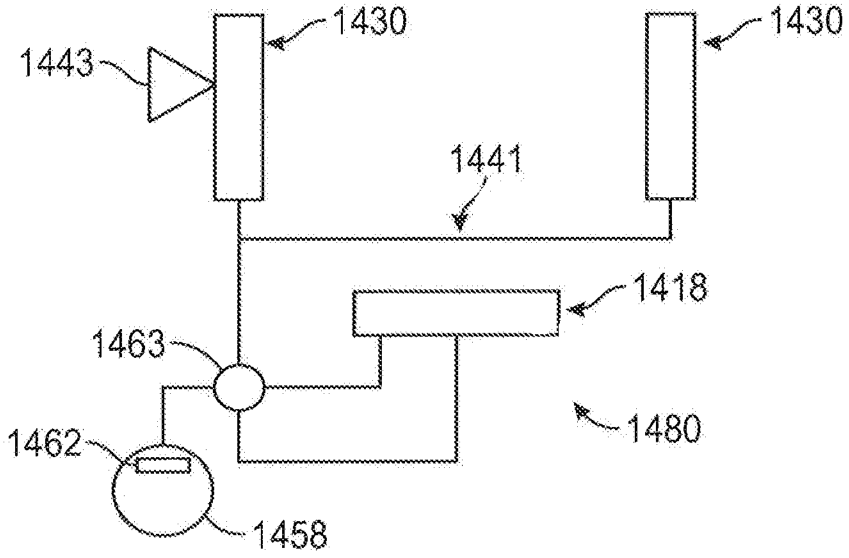
FIG. 37 depicts another exemplary fluid control system usable with the HFD of FIG. 26.

In one version having a simplified configuration for the fluid control system (1444), the fluid reservoir (1459) is omitted, and the pump (1458) comprises a hand pump or foot pump having a pressure gauge and configured to be manually operated. In this example, the pump (1458) is selectively connectable with the various valves (1457, 1460, 1461) to adjust fluid volumes and pressure within the pads (1430) and cushion (1418). In some versions, such as illustrated in FIG. 37, a fluid control system (1480) can have a single valve (1463) that is switchable can be used instead of the multiple valves (1457, 1460, 1461). In such an instance, the valve (1463) connects with the pump (1458) as well as the respective ports (1447, 1453) of the cushion (1418). As also shown, the valve (1463) can also be connected with the pads (1430) via the connection tube (1441), although this additional fluid connection is not required in all versions and may be controlled by a separate fluid control system. When controlling fluid within the fluid control system (1480), the valve (1463) is configured such that fluid can be directed to any of the fluid holding chambers of the cushion (1418) and/or the pads (1430). Moreover, the valve (1463) can be configured to direct fluid to more than one of the chambers of the cushion (1418) and/or pads (1430) at the same time. The pump (1458) is configured with a pressure gauge (1462) and the pressure gauge (1462) is configured to indicate a pressure within the chambers to which the valve (1463) is actively in fluid communication with. In view of the teachings herein, other configurations for the various fluid control systems will be apparent to those of ordinary skill in the art. For instance, it will be appreciated that to direct the fluid, a single pump or multiple pumps may be used, a single valve or multiple valves may be used, and a variety of ports and connection tubes may be used.

In the present example, the pump (1458) also connects two other valves (1460, 1461) that connect with the respective ports (1447, 1453) of the cushion (1418). The valves (1460, 1461) are configured similar to the valve (1457) and thus the pump (1458) can also be operated to provide additional fluid from the fluid reservoir (1459) to either or both of the outer chambers and middle chamber of the pad (1418). As described above, the fluid is provided to the first and third chambers (1445, 1451) of the cushion (1418). Furthermore, in this configuration, fluid can be vented or extracted from the cushion (1418) by either venting the fluid to the atmosphere via the valves (1460, 1461) in one example, or by opening the valves (1460, 1461) and operating the pump (1458) to transfer fluid to the fluid reservoir (1459). In view of the teachings herein, other ways to configure and operate the fluid control system (1444) to manipulate the pressures within the pads (1430) and cushion (1418) will be apparent to those of ordinary skill in the art.

Figure 36:
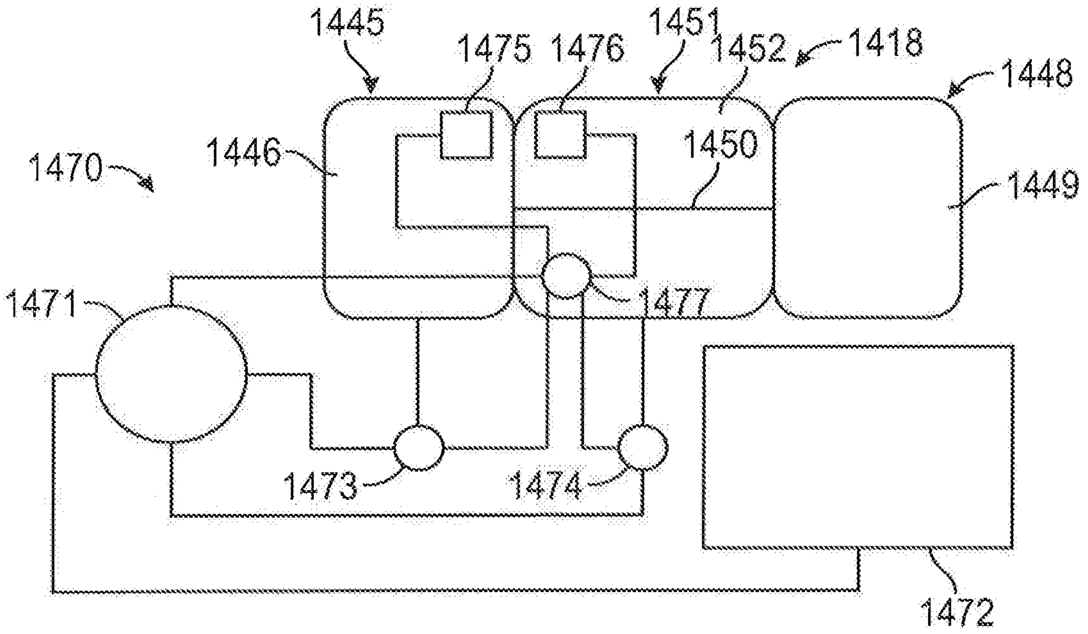
FIG. 36 depicts another exemplary fluid control system usable with the HFD of FIG. 26.

FIG. 36 shows another exemplary fluid control system (1470) that is usable with the HFD (600) when configured with the multi-chamber cushion (1418). The fluid control system (1470) is configured to provide fluid control where the outer chambers and middle chamber can be vented and refilled in an alternating manner as described above. Again, as discussed above this alternating venting or pressure relief provides for the ability to increase blood flow to certain areas of the patient's head, while also maintaining adequate stabilization of the patient's head.

As shown in the illustrated version of FIG. 36, the fluid control system (1470) comprises a pump (1471) connected to a fluid reservoir (1472) containing fluid. With the fluid control system (1470) the pump (1471) further connects with two valves (1473, 1474). One of the valves (1473) connects with the port (1447) of the first chamber (1445) of the cushion (1418), and the other valve (1474) connects with the port (1453) of the third chamber (1448) of the cushion (1418). The connections between the pump (1471), the fluid reservoir (1472), the valves (1473, 1474), and the ports (1447, 1453) are such that these components are in fluid communication so that fluid can be transported between these components. Accordingly, the fluid control system (1470) is configured to either direct fluid to the cushion (1418) or extract or vent fluid from the cushion (1418). As described above, the first chamber (1445) of the cushion (1418) connects with the second chamber (1448) by way of tube (1450) such that fluid changes impact both chambers (1445, 1448) in the same manner and to the same degree such that the pair of outer chambers have the same pressure.

Within the internal space (1446) of the first chamber (1445), the fluid control system (1470) includes a pressure sensor (1475). In some other versions, the pressure sensor (1475) can be instead located within the internal space (1449) of the second chamber (1448). The fluid control system (1470) further includes a pressure sensor (1476) located within the internal space (1452) of the third chamber (1451). In the present example, the pressure sensors (1475, 1476) connect with a control unit (1477). In the illustrated example, the control unit (1477) is also located within the internal space (1452) of the third chamber (1451). In some other versions, the control unit (1477) can be located in other positions within or outside of the cushion (1418). Also connected with the control unit (1477) are the valves (1473, 1474) and the pump (1471). The connections between the control unit (1477), the pump (1471), the valves (1473, 1474), and the sensors (1475, 1476) are such that these components are in electrical communication so that electrical signals can be transmitted and/or received by between these components. The components described here that transmit and/or receive signals are powered by batteries contained within these components. Of course in other versions, separate power sources may be used instead of or in addition to the batteries within the components. In view of the teachings herein, other ways to provide power to the components described here will be apparent to those of ordinary skill in the art.

With the configuration described above for FIG. 36, in operation the fluid control system (1470) can be configured such that the control unit (1477) is operable to change the fluid volumes within the first, second, and third chambers (1445, 1448, 1451) using signals from the pressure sensors (1475, 1476). For example, after some time has passed where a patient's head has been stabilized, it may be desired to selectively relieve pressure on the patient's head to restore blood flow to certain tissue areas contacted by the HFD (1000) to reduce the risk of tissue trauma or injury as described above. With the fluid control system (1470), the control unit (1477) can be programmed to execute a set of instructions whereby the pair of outer chambers of the cushion (1418) and the middle chamber are manipulated in an alternating fashion to relieve pressure by venting or extracting the fluid to allow for a period of increased blood flow to the tissue before increasing the pressure by delivering fluid back to the respective chamber from which the fluid was previously vented or extracted.

By way of example only, and not limitation, one alternating sequence of pressure relief using the fluid control system (1470) may be conducted by initiating at the control unit (1477) a first pressure relief action or process where the fluid is vented or extracted from the first and second chambers (1445, 1448) until the pressure sensor (1475) reaches a predetermined value. The predetermined value may be a percentage reduction in the pressure sensor (1475) reading, or it may be a selected pressure value that may be determined to increase blood flow to the tissue area without compromising the stability of the patient. Once the pressure sensor (1475) reaches the predetermined value, a predetermined wait time ensues where time is provided for restoration or increase of blood flow to the areas of tissue in contact with the outer chambers. After the predetermined wait time has elapsed, the control unit (1477) sends a signal to the pump (1471) and the valve (1473) to direct fluid to the first and second chambers (1445, 1448) to add fluid until the sensor (1475) reaches a predetermined value for pressure. This predetermined value may be the same as the pressure in the outer chambers of the cushion (1418) before the pressure relief cycle began, or it may be a different pressure value.

With the outer chambers refilled and having sufficient pressure to provide sufficient stabilizing force to the patient's head, next the control unit (1477) initiates a second pressure relief action or process where the fluid is vented or extracted from the third chamber (1451) until the pressure sensor (1476) reaches a predetermined value. The predetermined value may be a percentage reduction in the pressure sensor (1476) reading, or it may be a selected pressure value that may be determined to increase blood flow to the tissue area without compromising the stability of the patient. Once the pressure sensor (1476) reaches the predetermined value, a predetermined wait time ensues where time is provided for restoration or increase of blood flow to the areas of tissue in contact with the middle chamber. After the predetermined wait time has elapsed, the control unit (1477) sends a signal to the pump (1471) and the valve (1474) to direct fluid to the third chambers (1451) to add fluid until the sensor (1476) reaches a predetermined value for pressure. This predetermined value may be the same as the pressure in the middle chamber of the cushion (1418) before the pressure relief cycle began, or it may be a different pressure value. From this point, once alternating cycle would have been completed and subsequent alternating cycles could continue immediately thereafter or after some time has passed.

In view of the teachings herein, other ways to configure and operate the fluid control system (1470) will be apparent to those of ordinary skill in the art. For instance, in some versions, the sensors (1475, 1476), the valves (1473, 1474), the pump (1471), and/or the control unit (1477) may be connected with an output display where the pressure and fluid data within the cushion (1418) may be visually displayed. In other instances, this data could be wirelessly transmitted to a device with a display, e.g. the fluid control system (1470) could be operable via an application installed on a computer or tablet. Still yet, in other versions, the control unit (1477) may be located outside the cushion (1418) and further connected with the pads (1430) using similar sensors and valves such that the control unit (1477) is able to control fluid deliver and extraction from both the chambers of the cushion (1418) as well as one or more of the pads (1430). Still further, in some versions the pump (1471) includes an integrated measurement of the pressure, such that one or both of the sensors (1475, 1476) may be effectively part of or within the pump (1471).

XI. Exemplary Head Fixation Device with Adjustable-Fill Lateral Pads

Figure 38:
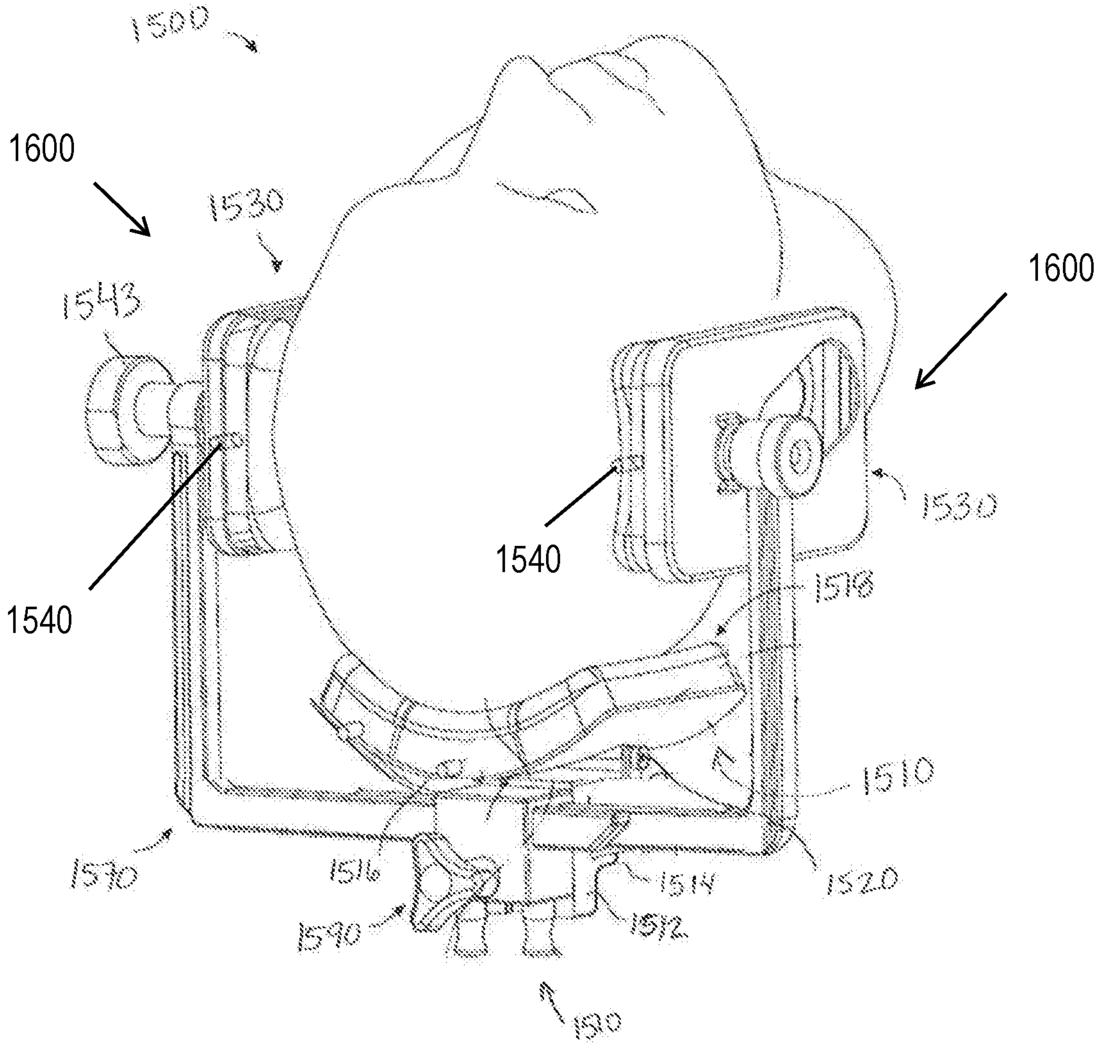
FIG. 38 depicts a perspective view of another exemplary HFD configured as a non-invasive HFD.

In some instances, a non-invasive HFD configuration may be desired where the stabilization assemblies have the form of pads instead of pins, where the pads provide the lateral stabilization. Additionally, the pads may be configured with certain contact pressure control features to help promote blood flow to certain tissue areas to avoid or reduce the risk of tissue injury or trauma. Referring to FIG. 38, an exemplary HFD (1500) is shown that is similar in many respects to the HFD (400), but where HFD (1500) incorporates pads (1530) rather than pads (430) shown with HFD (400), and without arc member (140). HFD (1500) also includes a cushion (1518) similar to the cushion (418) as described with respect to the HFD (400). HFD (1500) further includes features that aid in controlling pressure at the stabilization contact areas where pads (1530) contact the patient's head and at the stabilization contact area where cushion (1518) contacts the patient's head.

HFD (1500) comprises a skull clamp (1570) and an actuator (1590) similar to the skull clamp (170) and the actuator (190) as described above, and without arc member (140) as mentioned. Actuator (1590) may be rotated to adjust the arms of skull clamp (1570), which thereby adjust the position between pads (1530). In this respect, HFD (1500) comprises lateral head supports (1600), and lateral head supports (1600) comprise pads (1530). HFD (1500) also comprises a central head support (1510) that is similar to the central head support (410) as described above with respect to the HFD (400), however, the central head support (1510) includes a cushion (1518) instead of cushion (418) described above. Referring to FIG. 38, central head support (1510) comprises a body (1512) and an attachment feature (1514) on body (1512), where attachment feature (1514) is in the form of a starburst configured to connect with an operating table or other structure directly or indirectly via one or more intermediate structures. For example, in some instances a base unit, such as those available from pro med instruments GmbH, attaches to an operating table and attachment feature (1514) connects with the base unit. In some instances an adapter, such as a swivel adapter or other adapter available from pro med instruments GmbH, may connect with the base unit, and attachment feature (1514) of central head support (1510) connects with the adapter. In view of the teachings herein, various ways to connect central head support (1510) with a stable structure such as an operating table, etc. will be apparent to those of ordinary skill in the art.

Central head support (1510) also comprises a base (1516) that connects with body (1512) and that holds or retains cushion (1518). Cushion (1518) may connect with base (1516) by way of an adhesive, mechanical fasteners such as screws or hook and loop, or other ways that will be apparent to those of ordinary skill in the art. In some versions, cushion (1518) is selectively connected with base (1516) such that cushion (1518) may be disposable or may be removed for cleaning and sterilization after use. Cushion (1518) is configured to contact the head of the patient when HFD (1500) is used to support and stabilize the patient. In the present example, base (1516) connects with body (1512) by way of a pair of arms (1520) that extend from body (1512) outward and upward. In use in some, but not necessarily all, configurations, central head support (1510) is configured to provide subjacent support to the head of the patient.

In the illustrated embodiment, central head support (1510) of HFD (1500) is shown coupled with skull clamp (1570). In some other versions, central head support (1510) is coupled with the skull clamp (1570) via an arc member (140) and/or a cassette carrier (1202) as described above. Still other suitable configurations for coupling central head support (1510) with skull clamp (1570) will be apparent to one with ordinary skill in the art in view of the teachings herein.

Figure 5:
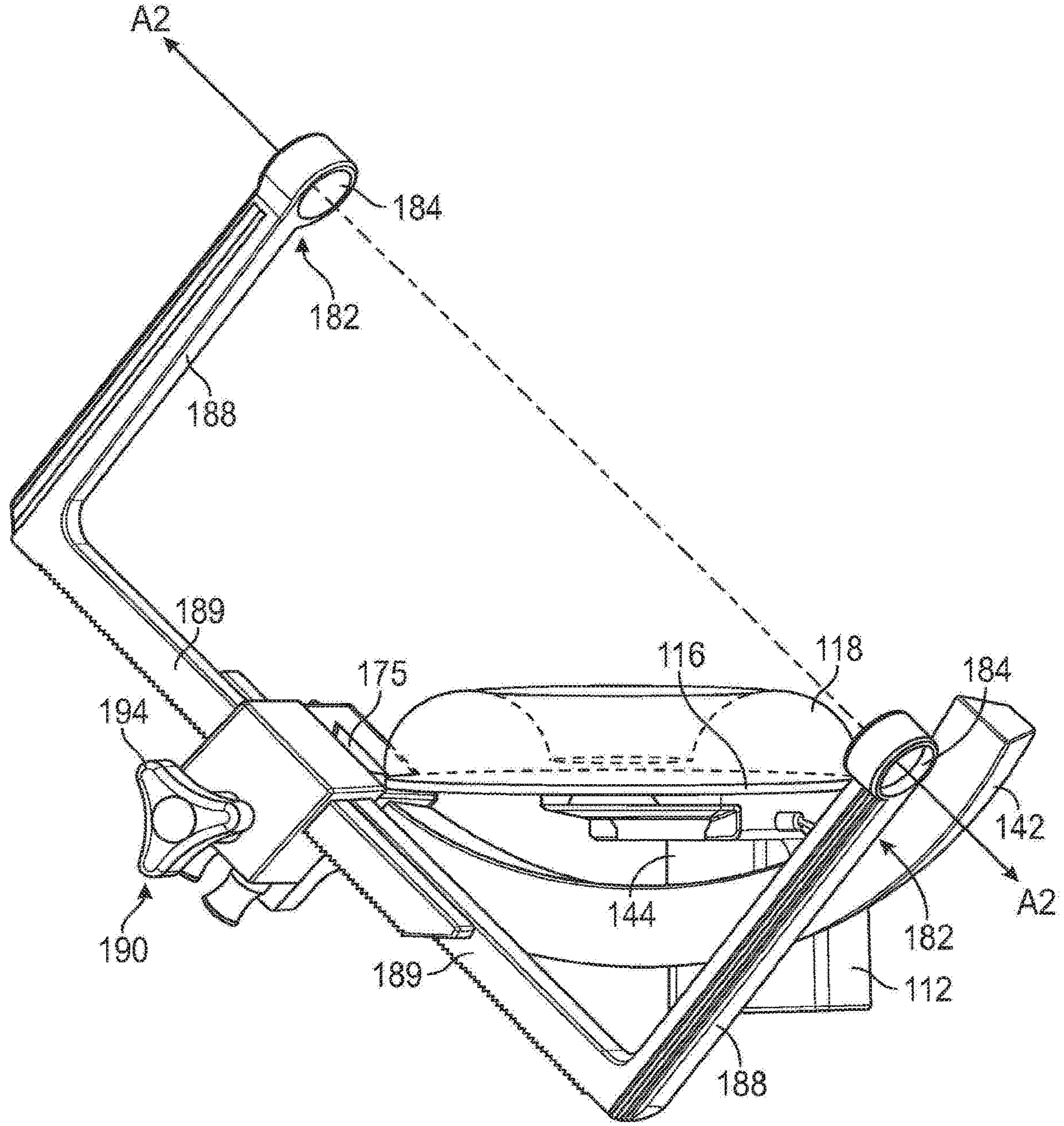
FIG. 5 depicts a perspective view of the HFD of FIG. 1, shown with the stabilizing assemblies removed.

Referring to FIGS. 38-41, HFD (1500) comprises pads (1530) as mentioned above. Pads (1530) comprise a housing (1531) and a chamber (1532). A bore or cut-out (1534) extends through housing (1531) and chamber (1532). Bore (1534) is located such that it is configured to receive a patient's ear during stabilization so as to protect the patient's ear from excessive compression and pressure, and instead direct such pressure and compressive force on the patient's skull. Located on housing (1531) is an annular flange (1535) that defines a slot (1536) configured to connect with the remainder of the stabilizing assembly. In the present example, the stabilizing assembly includes a collar (1537) having a flange (1538) that fits within the slot (1536). With this configuration, pad (1530) can be adjusted about an axis defined by and extending through bore (184) as illustrated in FIG. 5.

Chamber (1532) of pad (1530) defines an internal space (1539) that is configured to be filled with a fill material (1602). In some versions the fill material is a fluid, which may be a liquid or gas or combination. In still other versions the fill material is a solid material, which may be a particle or granular material. Still in some other versions, the fill material is a gel or other viscous material that has both solid and liquid characteristics in some respects. All of these fill materials can be and are considered shape-conforming materials as they are able to conform to the shape of the surface they contact. Chamber (1532) of pad (1530) also includes a port (1540) that can be opened and closed and that connects with and provides access to internal space (1539) of chamber (1532). In this manner, the fill material can be delivered to or vented or extracted from internal space (1539) of chamber (1532) by way of port (1540). In the illustrated embodiment, chamber (1532) comprises a single internal space (1539), and one that can be adjustably filled with a fill material while in use to alter or control applied pressure and stabilization. Still, in other versions, chamber (1532) may comprises more than one internal space so as to form a multi-chamber pad as described above.

Figure 40:
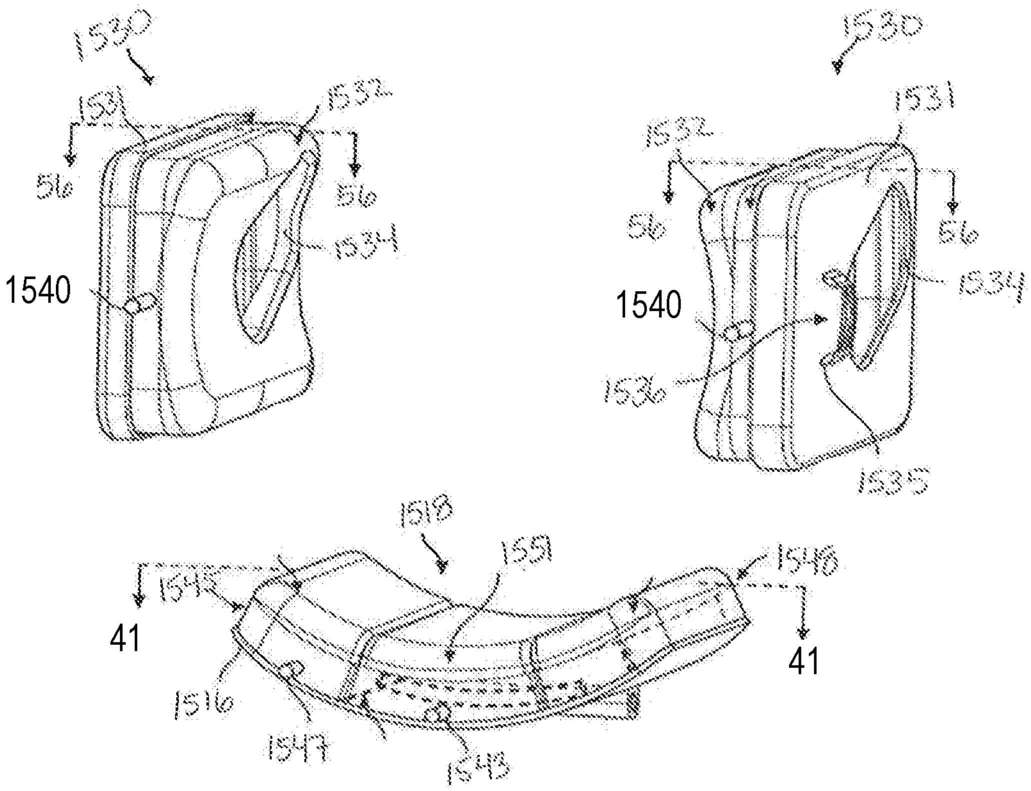
FIG. 40 depicts a rear perspective view of the cushion and pads used with the HFD of FIG. 38, but also useable with the HFDs of FIGS. 1, 9, 12, 16, 22, and 26.

Referring to FIG. 40, when pads (1530) are used with each stabilizing assembly, in some versions ports (1540) are connected by a tube, hose, or conduit. The tube may be connected to a valve and further connected to a fluid reservoir as described above. In this configuration, by connecting chamber (1532) of multiple pads (1530), the pressure within each pad's chamber (1532) is the same, and the pressure changes in the same fashion too as the chambers (1532) may be filled with more fill material to increase the pressure, or fill material removed from chambers (1532) to decrease pressure within.

With the configuration of pads (1530) described above, pads (1530) are configured to provide a uniform distribution of contact pressure with the head of the patient when the head is supported by the stabilization assemblies having pads (1530). Moreover, the contact pressure can be increased by filling the chamber (1532) with more fill material via port (1540). Conversely, the contact pressure can be decreased by venting or removing the fill material from chamber (1532) as mentioned above. By reducing the contact pressure, blood flow can be restored to the area of the patient's head in contact with pads (1530). In some instances, but not required in all versions, substantial removing or venting of the fill material from chamber (1532) may cause pads (1530) to deflate or reduce in size such that pads (1530) no longer apply contact pressure to the head of the patient sufficient for stabilization. In at least some instances, contact pressure sufficient to provide stabilization can be referred to as stabilizing pressure. By reducing the contact pressure to the extent that the stabilizing pressure between pads (1530) and the patient is lacking, blood flow can be restored to this area of the patient's head that was previously in contact with pads (1530) and under stabilizing pressure. By reducing contact pressure and providing for restoration of blood flow, tissue trauma or injury can be avoided or the risk reduced. Additionally, support of the patient's head can be maintained by cushion (1518) of central head support (1510) when reducing contact pressure between pads (1530) and the patient's head so as to not sacrifice support of the patient when restoring blood flow to an area of tissue. In some instances, once sufficient time has elapsed to restore blood flow to the tissue area in contact with pads (1530), the contact pressure can be increased again by filling chambers (1532) with the fill material to provide or restore an enhanced or a greater degree of stabilization. It should be understood, that it is not required in all versions to reduce the pressure within pads (1530) to the degree that all stabilizing pressure between pads (1530) and the patient's head is lacking to restore some or all blood flow to an area where pads (1530) contact the patient's head.

In some versions of HFD (1500), both of lateral pads (1530) are kept at the same pressure at all times. In some other versions, each pad (1530) is controllable independent from the other in terms of its pressure and fill material amount. In other words, in such versions that have independent control of pressure and/or fill material amount within each pad (1530), a connecting tube as mentioned above may be omitted or may include various valves for directing fill material. In view of the teachings herein, other ways to configure pads (1530) and control the pressure within will be apparent to those of ordinary skill in the art.

Figure 39:
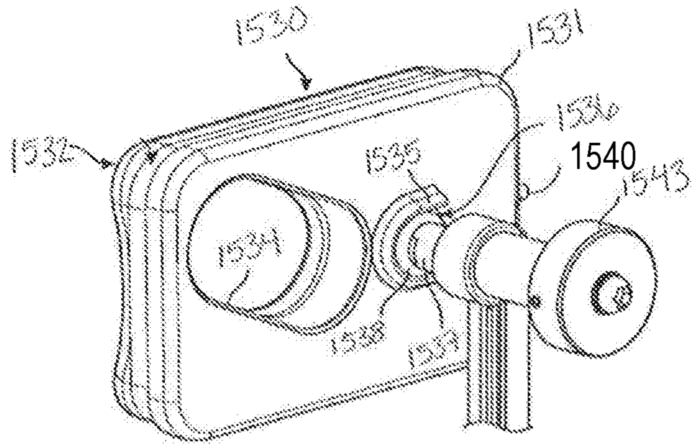
FIG. 39 depicts a partial perspective view of a stabilization assembly of the HFD of FIG. 38.

Referring to FIGS. 38 and 39, in some versions of HFD (1500), the pressure pads (1530) apply to the patient's head is adjustable using a torque screw (1543). Torque screw (1543) may be a component of one of the stabilizing assemblies. Tightening torque screw (1543) increases the pressure applied by pads (1530) to the patient's head. In the one version, a single torque screw (1543) is on one side of HFD (1500), and pads (1530) are connected by a tube such that actuation of torque screw (1543) changes the pressure in both pads (1530). In other versions, multiple torque screws (1543) could be used, one associated with each pad (1530). In some versions using multiple torque screws (1543), pads (1530) are not connected by the tube mentioned above. In some versions using HFD (1500), the initial stabilization may be accomplished using torque screw (1543). After setting torque screw (1543) initially, subsequent pressure adjustments could be made by adjusting the amount of fill material within chambers (1532) of pads (1530), e.g. by directing more fill material to chambers (1532) to increase the pressure, or by removing or venting fill material from chambers (1532) to decrease the pressure. In other words, in some versions, whether or not torque screw (1543) is included, the contact pressure provided by each pad (1530) can be controlled or adjusted separate and independent from torque screw (1543). In some versions, torque screw (1543) can be omitted altogether, and replaced with a conventional skull pin assembly. In view of the teachings herein, other ways to use either torque screw (1543) and/or fill amount to control pressure within pads (1530) will be apparent to those of ordinary skill in the art.

Figure 41:
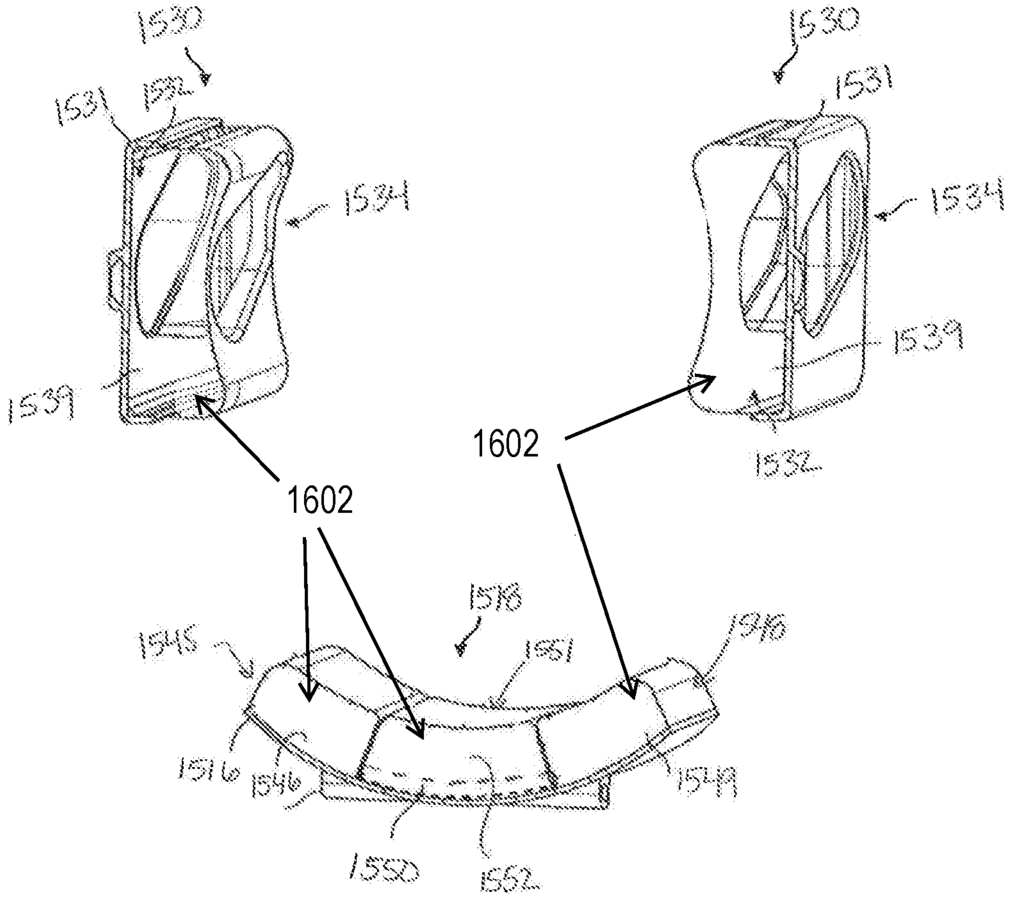
FIG. 41 depicts cross section view of the cushion and pads of FIG. 40.

Referring to FIGS. 40 and 41, HFD (1500) comprises cushion (1518) that connects with base (1516) of central head support (1510) as mentioned above. In the present example, cushion (1518) of HFD (1500) comprises a multi-chamber structure with a first chamber (1545) having an internal space (1546) that is configured to be filled with a fill material. First chamber (1545) includes a port (1547) that is configured to provide access to internal space (1546). The fill material may be directed to the internal space (1546) within first chamber (1545) or extracted from or vented from internal space (1546) of first chamber (1545). When venting or removing fill material from first chamber (1545), all or a portion of the fill material may be released or vented from internal space (1546). Cushion (1518) further comprises a second chamber (1548) having an internal space (1549) that is configured to be filled with the fill material or fill material may be extracted from or vented from internal space (1549) of second chamber (1548). When venting or removing fill material from second chamber (1548), all or a portion of the fill material may be released or vented from internal space (1549). In the present example, internal space (1546) of first chamber (1545) and internal space (1549) of second chamber (1548) are in fluid communication by way of a connection tube (1550) that extends between internal spaces (1546, 1549) of first and second chambers (1545, 1548).

Cushion (1518) further comprises a third chamber (1551) positioned between first and second chambers (1545, 1548). In this configuration, first and second chambers (1545, 1548) collectively define a pair of outer chambers while third chamber (1551) defines a middle chamber. Third chamber (1551) also comprises an internal space (1552), and connection tube (1550) extends through internal space (1552) of third chamber (1551). Internal space (1552) of third chamber (1551) is configured to be filled with the fill material similar to first and second chambers (1545, 1548). The fill material may be added to or removed from internal space (1552), which can change the pressure within this area of cushion (1518). Third chamber (1551) comprises a port (1553) similar to first chamber (1545). Port (1553) provides access to internal space (1552) and is used to direct fill material to internal space (1552) or vent or remove fill material from internal space (1552). While the illustrated embodiment depicts cushion (1518) having three chambers (1545, 1548, 1551), it should be understood that cushion (1518) may have any suitable number of one or more chambers.

With the configuration of cushion (1518) described above, cushion (1518) is configured to provide a various pressure profiles depending on the manner of adjustments with the fill material and each of the respective internal spaces (1546, 1549, 1552). For instance, in some versions, a uniform distribution of contact pressure can be achieved where third chamber (1551) is configured to hold the same amount of fill material per unit of volume within internal space (1552) as in internal spaces (1546, 1549) of first and second chambers (1545, 1548). Still in other versions, the outer chambers may have matching pressures while the middle chamber has a pressure that may be higher or lower than the pressure within the outer chambers. Furthermore, in this configuration with differing pressures between the outer chambers and the middle chamber, the fill material may be removed and/or added in a controlled fashion to provide a way to promote blood flow to an area of the patient's tissue in contact with a portion of cushion (1518) while maintaining secure stabilization of the patient's head.

By way of example only, and not limitation, in one version, a patient is initially stabilized using HFD (1500) with pads (1530) applying the same contact pressure to portions of the patient's head. In the initial stabilization, cushion (1518) is configured such that the outer chambers and middle chamber also apply the same contact pressure to other portions of the patient's head. In this example, HFD (1500) may be used with the patient in a supine position, but this is not necessary in all examples such that HFD (1500) may be used with the patient in other positions. After some time has passed, the pressure within pads (1530) and/or cushion (1518) can be manipulated so that blood flow can be restored or increased to the areas where the tissue of the patient's head contacts portions of HFD (1500). Moreover, this manipulation of pressure comprises a short-term relief or reduction of pressure to promote increased blood flow to the tissue, followed by an increase in pressure after a period of time has passed to provide for enhanced stabilization. Furthermore, this manipulation of pressure can be performed in an alternating fashion among pads (1530) and/or chambers of cushion (1518). By using this alternating fashion, the tissue areas in contact with HFD (1500) are treated with restored or increased blood flow while maintaining an acceptable degree of stabilization.

XII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical device for supporting and stabilizing a head of a patient during a medical procedure, is configured to connect with an operating table directly or indirectly via one or more intermediate structures. The medical device comprises (a) one or more lateral head supports, wherein each of the one or more lateral head supports is configured to provide lateral support to the head of the patient, and (b) one or more pads configured to contact the head of the patient. Each of the one or more pads is connectable with a respective one of the one or more lateral head supports. Each of the one or more pads comprises a chamber configured to selectively retain a fill material, wherein the chamber is further configured to be adjustably fillable with the fill material to change an amount of fill material within the chamber.

Example 2

The device of Example 1, further comprising (c) a central head support configured to provide subjacent support to the head of the patient, and (d) a cushion connectable with the central head support, wherein the cushion is configured to contact the head of the patient.

Example 3

The device of any one or more of Examples 1 through 2, wherein the fill material comprises a select one of a liquid, a solid, a gel, a gas, a fluid, a shape-conforming material, and combinations thereof.

Example 4

The device of any one or more of Examples 1 through 2, wherein the fill material comprises air.

Example 5

The device of any one or more of Examples 1 through 4, comprising two lateral head supports and two pads.

Example 6

The device of any one or more of Examples 1 through 5, wherein the chambers of each of the two pads are configured so that their fill material amount is independently controllable.

Example 7

The device of any one or more of Examples 1 through 5, wherein the chambers of each of the two pads are configured so that their fill material amount is adjustable in unison.

Example 8

The device of any one or more of Examples 1 through 7, wherein the chamber comprises an internal space configured to be filled with the fill material, wherein the chamber comprises a port configured to provide access to the internal space.

Example 9

The device of any one or more of Examples 1 through 8, wherein the chamber is further configured to be vented to release all or a portion of the fill material from the internal space.

Example 10

The device of any one or more of Examples 1 through 9, further comprising a pump connectable with the chambers of the pads to selectively transfer fill material to the pads.

Example 11

A medical device for supporting and stabilizing a head of a patient during a medical procedure is configured to connect with an operating table directly or indirectly via one or more intermediate structures. The medical device comprises (a) two or more lateral head supports, wherein each of the two or more lateral head supports is configured to provide lateral support to the head of the patient, (b) two or more pads configured to contact the head of the patient, wherein each of the two or more pads is connectable with a respective one of the two or more lateral head supports, wherein each of the two or more pads comprises a first chamber configured to receive a first fill material, (c) a central head support configured to provide subjacent support to the head of the patient, and (d) a cushion connectable with the central head support, wherein the cushion is configured to contact the head of the patient, wherein the cushion comprises a second chamber configured to receive a second fill material.

Example 12

The device of Example 11, wherein the first fill material and the second fill material are the same.

Example 13

The device of any one or more of Examples 11 through 12, wherein the cushion comprises multi-chamber configuration.

Example 14

The device of any one or more of Examples 11 through 13, further comprising a connection member that fluidly connects the first chamber of each of the two or more pads.

Example 15

The device of any one or more of Examples 1 through 14, further comprising an arc feature.

Example 16

The device of any one or more of Examples 1 through 14, further comprising a cassette feature.

XIII. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

By way of example only, and not limitation, lateral pads (1530) can be used with any of the HFDs described herein in place of either their respective lateral pads or pins shown. Furthermore, the various lateral pads shown and described with respect to any of the HFDs described herein may be used with any other HFDs described herein. Also, the various central head supports and cushions shown and described with respect to any of the HFDs described herein may be used with any other HFD described herein. Further yet, the central head support and its cushion may be omitted entirely in some versions. Again, various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A medical device for supporting and stabilizing a head of a patient during a medical procedure, wherein the medical device is configured to connect with an operating table directly or indirectly via one or more intermediate structures, wherein the medical device comprises:

(a) a pair of extension bars that each have an upright portion and a base portion, wherein the base portions are translationally movable relative to one another to adjust a width between the upright portions;

(b) two or more lateral head supports, wherein each of the two or more lateral head supports is configured to provide lateral support to a temporal region of the head of the patient, wherein the two or more lateral head supports connect with a respective one of the upright portions;

(c) two or more pads configured to contact opposing temporal regions of the head of the patient, wherein each of the two or more pads is connectable with a respective one of the two or more lateral head supports, wherein each of the two or more pads comprises a chamber configured to selectively retain a fill material, wherein the chamber is further configured to be adjustably fillable with the fill material to change an amount of the fill material within the chamber; and (d) a connection member that fluidly connects the chamber of each of the two or more pads with each other to allow fluid to flow unimpeded between the chamber of each of the two or more pads, wherein the connection member is configured to connect with a pump to transfer the fill material to or from the two or more pads, wherein the fill material amount within each chamber of the two or more pads is adjustable in unison via the connection member.

2. The device of claim 1, further comprising:

(e) a central head support configured to provide subjacent support to the head of the patient; and (f) a cushion connectable with the central head support, wherein the cushion is configured to contact the head of the patient.

3. The device of claim 2, wherein the connection member fluidly connects the chamber of each of the two or more pads, independent from the cushion connectable with the central head support.

4. The device of claim 1, wherein the chamber comprises an internal space configured to be filled with the fill material, wherein the chamber comprises a port configured to provide access to the internal space.

5. The device of claim 4, wherein the chamber is further configured to be vented to release all or a portion of the fill material from the internal space.

6. The device of claim 1, wherein the fill material comprises a select one of a liquid, a solid, a gel, a gas, a fluid, a shape-conforming material, and combinations thereof.

7. The device of claim 1, wherein the fill material comprises air.

8. The device of claim 1, further comprising the pump.

9. A medical device for supporting and stabilizing a head of a patient during a medical procedure, wherein the medical device is configured to connect with an operating table directly or indirectly via one or more intermediate structures, wherein the medical device comprises:

(a) a pair of extension bars that each have an upright portion and a base portion, wherein the base portions are translationally movable relative to one another to adjust a width between the upright portions;

(b) two or more lateral head supports, wherein each of the two or more lateral head supports is configured to provide lateral support to a temporal region of the head of the patient, wherein the two or more lateral head supports connect with a respective one of the upright portions;

(c) two or more pads configured to contact opposing temporal regions of the head of the patient, wherein each of the two or more pads is connectable with a respective one of the two or more lateral head supports, wherein each of the two or more pads comprises a first chamber configured to receive a first fill material;

(d) a central head support configured to provide subjacent support to the head of the patient; and (e) a cushion connectable with the central head support, wherein the cushion is configured to contact the head of the patient, wherein the cushion comprises multiple chambers, wherein each chamber of the multiple chambers is configured to receive a second fill material, wherein the multiple chambers comprise a second and third chamber fluidly connected with each other to allow fluid to flow unimpeded between the second and third chambers such that the amount of respective second fill material within each of the second and third chambers is adjustable in unison, wherein the multiple chambers further comprise a fourth chamber independently adjustable in the amount of respective second fill material relative to the second and third chambers.

10. The device of claim 9, further comprising a connection member that fluidly connects the first chamber of each of the two or more pads.

11. The device of claim 10, wherein the connection member fluidly connects the first chamber of each of the two or more pads independent from the cushion connectable with the central head support.

12. The device of claim 9, wherein the central head support and the cushion are separate from the two or more lateral head supports and the two or more pads such that each of the two or more pads and the cushion are independently positionable when stabilizing the head of the patient.

13. The device of claim 9, wherein the first fill material and the second fill material differ.

14. The device of claim 9, wherein the fourth chamber of the multiple chambers is disposed between and separates the second and third chambers.

15. A medical device for supporting and stabilizing a head of a patient during a medical procedure, wherein the medical device is configured to connect with an operating table directly or indirectly via one or more intermediate structures, wherein the medical device comprises:

(a) a pair of extension bars that each have an upright portion and a base portion, wherein the base portions are translationally movable relative to one another to adjust a width between the upright portions;

(b) two or more lateral head supports, wherein each of the two or more lateral head supports is configured to provide lateral support to a temporal region of the head of the patient, wherein the two or more lateral head supports connect with a respective one of the upright portions;

(c) two or more pads configured to contact opposing temporal regions of the head of the patient, wherein each of the two or more pads is connectable with a respective one of the two or more lateral head supports, wherein each of the two or more pads comprises a first chamber configured to receive a first fill material;

(d) a connection member that fluidly connects the first chamber of each of the two or more pads with each other to allow fluid to flow unimpeded between the first chamber of each of the two or more pads, wherein the first fill material amount within each first chamber of the two or more pads is adjustable in unison via the connection member;

(e) a central head support configured to provide subjacent support to the head of the patient; and (f) a cushion connectable with the central head support, wherein the cushion is configured to contact the head of the patient, wherein the cushion comprises multiple chambers configured to receive a select one or more of the first fill material, a second fill material, and combinations thereof, wherein each of the multiple chambers of the cushion are each independently adjustable in the amount of respective fill material they contain.

16. The device of claim 15, wherein the first fill material and the second fill material differ.

* * * * *